US007615349B2

(12) United States Patent (10) Patent No.: US 7,615,349 B2
Riker et al. (45) Date of Patent: Nov. 10, 2009

(54) MELANOMA GENE SIGNATURE

(75) Inventors: Adam I. Riker, Mobile, AL (US); Steven Alan Enkemann, Lutz, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 0 days.

(21) Appl. No.: 11/852,102

(22) Filed: Sep. 7, 2007

(65) Prior Publication Data

US 2008/0113360 A1 May 15, 2008

Related U.S. Application Data

(60) Provisional application No. 60/824,849, filed on Sep. 7, 2006.

(51) Int. Cl.
*C12Q 1/68* (2006.01)
(52) U.S. Cl. .................................................. 435/6
(58) Field of Classification Search ...................... 435/6
See application file for complete search history.

(56) References Cited

U.S. PATENT DOCUMENTS

| 7,056,674 B2 | 6/2006 | Baker et al. |
| 7,081,340 B2 | 7/2006 | Baker et al. |
| 7,171,311 B2 | 1/2007 | Dai et al. |
| 7,247,426 B2 | 7/2007 | Yakhini et al. |
| 2006/0183141 A1 | 8/2006 | Change et al. |
| 2007/0154889 A1 | 7/2007 | Wang et al. |

OTHER PUBLICATIONS

Tockman et al (Cancer Res., 1992, 52:2711s-2718s).*
Greenbaum et al. (Genome Biology, 2003, vol. 4, Issue 9, pp. 117.1-117.8).*
Glas et al., "Converting a breast cancer microarray signature into a high-throughput diagnostic test," *BMC Genomics*, vol. 7:278-288 (2006).
Ai et al., "Epigenetic Silencing of the Tumor Suppressor Cystatin M Occurs during Breast Cancer Progression," *Cancer Research*, vol. 66:7900-7909 (2006).
An et al., "Deletion of tumor suppressor genes in Chinese non-small cell lung cancer," *Cancer Letters*, vol. 184:189-195 (2002).
Balch et al. "A New American Joint Committee on Cancer Staging System for Cutaneous Melanoma," *Cancer*, vol. 88:1484-1491 (2000).
Balch et al., "Final version of the American Joint Committee on Cancer Staging System for Cutaneous Melanoma," *Journal of Clinical Oncology*, vol 19:3635-3648 (2001).
Balch et al., "Prognostic Factors Analysis of 17,600 Melanoma Patients: Validation of the American Joint Committee on Cancer Melanoma Staging System," *Joint of Clinical Oncology*, vol. 19:3622-3634 (2001).

Barrow et al., "Tumor Antigen Expression in Melanoma Varies According to Antigen and Stage," *Clin. Can. Res.*, vol. 12:764-771 (2006).
Bauskin et al., "Role of Macrophage Inhibitory Cytokine-1 in Tumorigenesis and Diagnosis of Cancer," *Cancer Research*, vol. 66:4983-4986 (2006).
Baylin et al., "Alterations in DNA Methylation: A Fundamental Aspect of Neoplasia," *Adv. in Cancer Res*, vol. 72:141-196 (1998).
Bittner et al., "Molecular classification of cutaneous malignant melanoma by gene expression profiling," *Nature*, vol. 406:536-540 (2000).
Brasseur et al. "Expression of *Mage* Genes in Primary and Metastatic Cutaneous Melanoma,"*Int. J. Cancer*, vol. 63:375-380 (1995).
Cascinelli et al., "Sentinel Lymph Node Biopsy in Cutaneous Melanoma: The WHO Melanoma Program Experience," *Annals of Surgical Oncology*, vol. 7:469-474 (2000).
Chen et al., "Decreased PITX1 homeobox gene expression in human lung cancer," *Lung Cancer*, vol. 55:287-294 (2007).
Coppola et al., "Correlation of Osteopontin Protein Expression and Pathological Stage across a Wide Variety of Tumor Histologies," *Clin. Can. Res.*, vol. 10:184-190 (2004).
DeRisi et al., "Use of a cDNA microarray to analyze gene expression patterns in human cancer," *Nature Genetics*, vol. 14:457-460 (1996).
Dobbin et al, "Interlaboratory Comparability Study of Cancer Gene Expression Analysis Using Oligonucleotide Microarrays," *Clinical Cancer Research*, vol. 11:565-572 (2005).
Eton et al., "Prognostic Factors for Survival of Patients Treated Systemically for Disseminated Melanoma," *Journal of Clinical Oncology*, vol. 16:1103-1111 (1998).
Fujiwara et al., "Isolation of a candidate tumor suppressor gene on chromosome 8p21.3-p22 that is homologous to an extracellular domain of the PDGF receptor beta gene," *Oncogene*, vol. 10:891-895 (1995).
Gallagher et al., "Multiple markers for melanoma progression regulated by DNA methylation: Insights from transcriptomic studies," *Carcinogenesis*, vol. 26:1856-1867 (2005).
Garraway et al., "Integrative genomic anlayses identify *MITF* as a lineage survival oncogene amplified in malignant melanoma," *Nature*, vol. 436:117-122 (2005).
Golub et al., "Molecular Classification of Cancer: Class Discovery and Class Prediction by Gene Expression Monitoring," *Science*, vol. 286:531-537 (1999).
Haddad et al., "The Progression of Melanoma Nodal Metastasis is Dependent on Tumor Thickness of the Primary Lesion," *Annals of Surgical Oncology*, vol. 6:144-149 (1999).
Hanahan et al., "The Hallmarks of Cancer," *Cell*, vol. 100:57-70 (2000).
Haqq et al., "The gene expression signatures of melanoma progression," *Proc. Natl. Acad. Sci. U. S. A.*, vol. 102:6092-6097 (2005).
Harbig et al., "A sequence-based identification of the genes detected by probesets on the Affymetrix U133 plus 2.0 array," *Nucleic Acids Research*, vol. 33:e31 (2005).

(Continued)

*Primary Examiner*—Sean E Aeder
(74) *Attorney, Agent, or Firm*—Fish & Richardson P.C.

(57) ABSTRACT

Methods and compositions for evaluating gene expression in melanoma samples are provided herein.

8 Claims, 6 Drawing Sheets

OTHER PUBLICATIONS

Herman et al., "Gene Silencing in Cancer in Association with Promoter Hypermethylation," *N. Engl. J. Med.*, vol. 349:2042-2054 (2003).

Hodi, "Well-Defined Melanoma Antigens as Progression Markers for Melanoma: Insights into Differential Expression and Host Response Based on Stage," *Clin. Can. Res.*, vol. 12:673-678 (2006).

Jaeger et al., "Gene Expression Signatures for Tumor Progression, Tumor Subtype, and Tumor Thickness in Laser-Microdissected Melanoma Tissues," *Clin. Can. Res.*, vol.13:806-815 (2007).

Jemal et al., "Cancer Statistics, 2007," *C.A. Cancer J. Clin.*, vol. 57:43-66 (2007).

Jensen et al., "Down-Regulation of Pro-Apoptotic Genes is an Early Event in the Progression of Malignant Melanoma," *Annals of Surgical Oncology*, vol. 14:1416-1423 (2007).

Kim et al., "Epigenomic Profiling Reveals Novel and Frequent Targets of Aberrant DNA Methylation-Mediated Silencing in Malignant Glioma," *Cancer Res.*, vol. 66:7490-7501 (2006).

Kolfschoten et al., "A genetic screen identifies PITX1 as a suppressor of RAS activity and tumorigenicity," *Cell*, vol. 121:849-858 (2005).

Lerebours et al., "Fine Deletion Mapping of Chromosome 8p in Non-Small-Cell Lung Carcinoma," *Int. J. Cancer*, vol. 81:854-858 (1999).

Levy et al., "MITF: master regulator of melanocyte development and melanoma oncogene," *Trends Molecular Medicine*, vol. 12:406-414 (2006).

Li et al., "Model-based analysis of oligunucleotide arrays: Expression index computation and outlier detection," *Proc. Natl. Acad. Sci. U.S.A.*, vol. 98:31-36 (2001).

Lord et al.,. "Increased *CDX2* and decreased *PITX1* homeobox gene expression in Barrett's esophagus and Barrett's-associated adenocarcinoma," *Surgery*, vol. 138:924-931 (2005).

McGill et al., "c-Met Expression is Regulated by Mitf in the Melanocyte Lineage," *J. Biol. Chem.*, vol. 281:10365-10373 (2006).

Momparler, "Cancer epigenetics," *Oncogene*, vol. 22:6479-6483 (2003).

Muthusamy et al., "Epigenetic Silencing of Novel Tumor Suppressors in Malignant Melanoma," *Cancer Res.*, vol. 66:11187-11193 (2006).

Riker, "Isolation and Culture of Melanoma Cell Lines," *Cancer Cell Culture: Methods and Protocols*, Totowa: Humana Press, vol. 88:93-100 (2004).

Riker et al., Development and Characterization of Melanoma Cell Lines Established by Fine Needle Aspiration Biopsy: Advances in the Monitoring of Patients with Metastatic Melanoma, *Cancer Detection and Prevention*, vol. 23:387-396 (1999).

Rivenbark et al., "DNA methylation-dependent silencing of CST6 in human breast cancer cell lines," *Laboratory Investigation*, vol. 86:1233-1242 (2006).

Seitz et al., "Genetic Background of Different Cancer Cell Lines Influences the Gene Set Involved in Chromosome 8 Mediated Breast Tumor Suppression," *Genes, Chromosomes & Cancer*, vol. 45:612-627 (2006).

Seykora et al., "Gene Expression Profiling of Melanocytic Lesions," *The American Journal of Dermatopathology*, vol. 25:6-11 (2003).

Smith et al., "Whole-Genome Expression Profiling of the Melanoma Progression Pathway Reveals Marked Molecular Differences Between Nevi/Melanoma in Situ and Advanced-Stage Melanomas," *Cancer Biology & Therapy*, vol. 4:1018-1029 (2005).

Talantov et al., "Novel Genes Associated with Malignant Melanoma but not Benign Melanocytic Lesions," *Clinical Cancer Research*, vol. 11:7234-7242 (2005).

Trent et al., "Tumorigenicity in Human Melanoma Cell Lines Controlled by Introduction of Human Chromosome 6," *Science*, vol. 247:568-571 (1990).

Van Gelder et al., "Amplified RNA synthesized from limited quantities of heterogeneous cDNA," *Proc. Natl. Acad. Sci. U.S.A.*, vol. 87:1663-1667 (1990).

Vogl et al., Gene Expression Profile Changes between Melanoma Metastases and their Daughter Cell Lines: Implication for Vaccination Trials, *J. Invest. Dermatol.*, vol. 124:401-404 (2005).

Warrington et al., "Comparison of human adult and fetal expression and identification of 535 housekeeping/maintenance genes," *Physiol. Genomics*, vol. 2:143-147 (2000).

Weyers et al., "Classification of Cutaneous Malignant Melanoma: A Reassessment of Histopathologic Criteria for the Distinction of Different Types," *Cancer*, vol. 86:288-299 (1999).

Winnepenninckx et al., "Gene Expression Profiling of Primary Cutaneous Melanoma and Clinical Outcome," *J. Natl. Cancer Inst.*, vol. 98:472-482 (2006).

Wollmann et al., "The macrophage inhibitory cytokine integrates AKT/PKB and MAP kinase signaling pathways in breast cancer cells," *Carcinogenesis*, vol. 26:900-907 (2005).

Zhang et al., "Aberrant promoter methylation and silencing of the *POU2F3* gene in cervical cancer," *Oncogene*, vol. 25:5436-5445 (2006).

Zhou et al., "Osteopontin Expression Correlates with Melanoma Invasion," *J. Invest. Dermatol.*, vol. 124:1044-1052 (2005).

Alonso et al., "A High-Throughput Study in Melanoma Identifies Epithelial-Mesenchymal Transition as a Major Determinant of Metastasis," *Cancer Research*, vol. 67:3450-3460 (2007).

Baldi et al., "Identification of genes down-regulated during melanoma progression: a cDNA array study," *Experimental Dermatology*, vol. 12:213-218 (2003).

Becker et al., "Discrimination of Melanocytic Tumors by cDNA Array Hybridization of Tissues Prepared by Laser Pressure Catapulting," *The Journal of Investigative Dermatology*, vol. 122:361-368 (2004).

De Wit et al., "Analysis of differential gene expression in human melanocytic tumour lesions by custom made oligonucleotide arrays," *British Journal of Cancer*, vol. 92:2249-2261 (2005).

Dooley et al., "DNA Microarrays and Likelihood Ratio Bioinformatic Methods: Discovery of Human Melanocyte Biomarkers," *Pigment Cell Res.*, vol. 16:245-253 (2003).

Eisen et al., "Cluster analysis and display of genome-wide expression patters," *Proc. Nat. Acad. Sci. USA*, vol. 95:14863-14868 (1998).

Felicetti et al., "Role of PLZF in melanoma progression," *Oncogene*, vol. 23:4567-4576 (2004).

Ghosh et al., "Three-Dimensional Culture of Melanoma Cells Profoundly Affects Gene Expression Profile: A High Density Oligonucleotide Array Study," *Journal of Cellular Physiology*, vol. 204:522-531 (2005).

Heyer et al., "Exploring Expression Data: Identification and Analysis of Coexpressed Genes" *Genome Research*, vol. 9:1106-1115 (1999).

Hoek et al., "Expression Profiling Reveals Novel Pathways in the Transformation of Melanocytes to Melanomas," *Cancer Research*, vol. 64:5270-5282 (2004).

Hoek et al., "Metastatic potential of melanomas defined by specific gene expresson profiles with no BRAF signature," *Pigment Cell Res.*, vol. 19:290-302 (2006).

Jean et al., "The expression of genes induced in melanocytes by exposure to 365-nm UVA: study by cDNA arrays and real-time quantitative RT-PCR," *Biochimica et Biophysica Acta*, vol. 1522:89-96 (2001).

Mandruzzato et al., "A gene expression signature associated with survival in metastatic melanoma," *Journal of Translational Medicine*, vol. 4:50 (2006).

Mirmohammadsadegh et al., Rapid Identification of Dysregulated Genes in Cutaneous Malignant Melanoma Metastases, *Cells Tissues Organs*, vol. 177:119-123 (2004).

Mischiati et al., "cDNA-Array Profiling of Melanomas and Paired Melanocyte Cultures," *Journal of Cellular Physiology*, vol. 207:697-705 (2006).

Moretti et al., "In situ expression of transforming growth factor β is associated with melanoma progression and correlates with Ki67, HLA-DR and β3 integrin expression," *Melanoma Research*, vol. 7:313-321 (1997).

Niezabitowski et al., Prognostic Evaluation of Cutaneous Malignant Melanoma: A Clinicopathologic and Immunohistochemical Study, *Journal of Surgical Oncology*, vol. 70:150-160 (1999).

Onken et al., "Gene Expression Profiling in Uveal Melanoma Reveals Two Molecular Classes and Predicts Metastatic Death," *Cancer Research*, vol. 64:7205-7209 (2004).

Onken et al. "Association Between Microarray Gene Expression Signature and Extravascular Matrix Patterns in Primary Uveal Melanomas," *American Journal of Opthalmology*, vol. 140:748-749 (2005).

Onken et al., "Functional Gene Expression Analysis Uncovers Phenotypic Switch in Aggressive Uveal Melanomas," *Cancer Research*, vol. 66:4602-4609 (2006).

Pavey et al., "Microarray expression profiling in melanoma reveals a *BRAF* mutation signature," *Oncogene*, vol. 23:4060-4067 (2004).

Seftor et al., "Molecular determinants of human uveal melanoma invasion and metastasis," *Clinical & Experimental Metastasis*, vol. 19:233-246 (2002).

Seykora et al., "Gene Expression Profiling of Melanocytic Lesions," *The American Journal of Dermatopathology*, vol. 25:6-11 (2003).

Soikkeli et al., "Systematic search for the best gene expression markers for melanoma micrometastasis detection," *Journal of Pathology*, vol. 213:180-189 (2007).

Tschentscher et al., "Tumor Classification Based on Gene Expression Profiling Shows That Uveal Melanomas with and without Monosomey 3 Represent Two Distinct Entities," *Cancer Research*, vol. 63:2578-2584 (2003).

Tusher et al., "Significance analysis of microarrays applied to the ionizing radiation response," *PNAS*, vol. 98:5116-5121 (2001).

Väisänen et al., "Prognostic Value of MMP-2 Immunoreactive Protein (72 kD Type IV Collagenase) in Primary Skin Melanoma," *Journal of Pathology*, vol. 186:51-58 (1998).

Wang et al., "Prospective Molecular Profiling of Melanoma Metastases Suggests Classifiers of Immune Responsiveness," *Cancer Research*, vol. 62:3581-3586 (2002).

Wang et al., "Iterative Normalization of cDNA Microarray Data," *IEEE Transactions on Information Technology in Biomedicine*, vol. 6:29-37 (2002).

Zuidervaart et al, "Gene expression profiling identifies tumour markers potentially playing a role in uveal melanoma development," *British Journal of Cancer*, vol. 89:1914-1919 (2003).

Dressman et al., "Gene expression profiles of multiple breast cancer phenotypes and response to neoadjuvant chemotherapy," *Clin. Cancer Res.*, 12(3):819-826 (2006).

de Wit et al., "Analysis of differential gene expression in human melanocytic tumour lesions by custom made oligonucleotide arrays," *British Journal of Cancer*, 92:2249-2261 (2005).

Riker et al., "The Gene Expression Profiles of primary and metastatic melanoma yields a transition point of tumor progression and metastasis,"*BMC Medical Genomics*, 1:13 (2008).

* cited by examiner

MELANOMA GENE SIGNATURE

RELATED APPLICATIONS

This application claims the benefit of U.S. Provisional Application No. 60/824,849, filed Sep. 7, 2006, which is incorporated herein by reference in its entirety.

GOVERNMENT SUPPORT

The methods and compositions described herein were made with government support awarded by the ARMY Medical Research and Material Command (MRMC) under Grant No. DAMD17-02-2-0051. The government has certain rights in the invention.

TECHNICAL FIELD

Methods and compositions for evaluating tissues, e.g., tumors, are provided herein.

BACKGROUND

In the United States, the overall incidence of melanoma is increasing at a rate faster than any other cancer, with recent estimates for lifetime risk of developing invasive melanoma at 1/49 (Jemal et al., C. A. Cancer J. Clin. 57:43-66, 2007). The development of melanoma begins with the malignant transformation of normal human epithelial melanocytes (NHEM) located within the basement membrane of the skin, but the genetic changes associated with the progression of NHEM to melanoma are not well characterized (Bittner et al., Nature. 406:536-540, 2000; DeRisi et al., Nat. Genet. 14:457-460, 1996; Golub et al., Science. 286:531-37, 1999; Hanahan et al., Cell. 100-57-70, 2000; Seykora et al., Am. J. Dermatopathol. 25:6-11, 2003; Su et al., Nature. 406:536-540, 2000; Trent et al., Science. 247:568-571, 1990; Weyers et al., Cancer. 86:288-299, 1999). Similarly, the molecular mechanisms underlying further progression from a primary tumor to a metastatic melanoma are also inadequately defined.

There is a correlation between the thickness of the primary melanoma and its capacity to metastasize to the draining lymph node basin(s) and hematogenously (Haddad et al., Ann. Surg. Oncol. 6:144-149, 1999; Cascinelli et al., Ann. Surg. Oncol. 7:469-474, 2000). Once melanoma has metastasized by either route, the overall survival for patients greatly diminishes (Balch et al., Cancer. 88:3635-3648; 2001; Balch et al., J. Clin. Oncol. 19:3622-3634, 2001). Whereas patients with thin primary tumors are cured by surgery, patients diagnosed with metastatic melanoma (AJCC stage IV) have an overall poor prognosis, with 6 out of every 7 skin cancer deaths due to metastatic melanoma (Balch et al., Cancer. 88:1484-1491, 2000; Eton et al., J. Clin. Oncol. 16:1103-1111, 1998; Jemal et al., C. A. Cancer J. Clin. 57:43-66, 2007).

SUMMARY

The compositions and related methods provided herein are based, in part, on the discovery of unique gene expression profiles characteristic of primary basal cell, squamous cell, non-metastatic, and metastatic melanoma skin cancer samples. A consistent "transition zone" of gene expression change within primary melanoma samples was observed and has allowed identification of gene expression profiles capable of distinguishing a primary tumor from metastatic melanoma. This transition in gene expression involves both increased expression levels of genes such as MAGE genes, GPR19, BCL2A1, SOX5, BUB1, and RGS20, and an even greater reduction in the expression of genes such as SPRR1A/B, KRT16/17, CD24, LOR, GATA3, MUC15, and TMPRSS4. The transition in gene expression also involves other genes described herein. For example, the transition involves a reduction in expression of a plurality of (including all of) the following genes: GJB6, SPRR1A, SERPINB5, CALML5 (CLSP), DSC1, PKP1, CLCA2, DSG1, CDSN, LY6D, LCE2B, FLG; RP1-14N1.3, KRT16, SBSN, SERPINB3, SERPINB7, KRT17, KLK7, LOR, SLURP1, LOC63928, KRT15, LGALS7, CST6, SPRR1B, CNFN, TRIM29, EPPK1, SFN, KRT6B, DSG3, SPRR2B, DMKN, ASAH3, SERPINB13, KLK11, AADACL2, DAPL1, ABCA12, DSC3, POF1B, GATA3, LYPD3, KRT6A, EHF, PCDH21, CBLC, FGFR2, SCEL, and FGFR3. For example, the transition involves an increase in expression of a plurality of (including all of) the following genes: MAGEA3, MAGEA6, CSAG2 (TRAG3), MAGEA12, MAGEA2, TRIM51, NRP2, MAGEA1, MSI2, GYPC, SPP1, SOX5, KIFC1, HILS1, RGS20, BUB1, IGF2BP3, FRMD5, C1orf90, EYA4, BCL2A1, SLC16A4, AKT3, CDC45L, SEC22L3, PEG10, POPDC3, MAGEA5, GLUD2, ST6GALNAC3, SEZ6L2, DUSP4, ABCB5, RASGRF1, DUSP4, FLJ40142, BRRN1, PHLDA1, MMP14, DUSP6, DPY19L1, GLUD1, LOC346615, CALU, RNF157, PRDM13, PBK, KIAA1618, NEDD4L, BICD1, and RRM2. The transition may further involve an increase in expression of one or more of the foregoing genes in conjunction with a decrease in expression of one or more of the previous set of genes. Additionally, a correlation between primary melanoma tumor thickness, as measured by Breslow's depth, and the accumulation of individual gene expression changes has also been discovered. The genes identified as changing expression in primary cutaneous melanoma along the spectrum of increasing Breslow's thickness, are useful markers for the existence of cells characteristic of metastatic melanoma. As further described herein, expression of the genes (e.g., five or more of the genes listed above, and/or five or more of the genes described in Tables. A-D, herein) can be examined in various combinations.

Accordingly, in one aspect, the technology herein features a method of evaluating a melanoma from a patient. The method includes determining expression of five or more genes in a test sample from a melanoma, relative to a control, wherein the five or more genes are selected from the genes listed in Table A and Table B, thereby evaluating the melanoma.

In various embodiments, expression of at least 10 genes from Tables A and B is determined, e.g., expression of at least 25, 50, 100, 250, 500, 750, 1000, 1250, or 1500 genes is determined. In various embodiments, expression of no more than 1500, 1250, 1000, 750, 500, 250, 100, 50, or 25 genes is determined. The at least 10 genes may be chosen in any combination from Tables A and B. Thus, in some embodiments, the at least 10 genes includes five genes from Table A and five genes from Table B. Other combinations may be examined, such as one gene from Table A and nine genes from Table B, and so forth. In some embodiments, expression of genes from Table A or Table B is determined (e.g., expression of at least 10 genes from Table A is determined to the exclusion of genes from Table B, or, alternatively, expression of at least 10 genes from Table B is determined, to the exclusion of genes from Table A).

In various embodiments, expression of the five or more genes is determined relative to expression of the five or more genes in a reference set of non-metastatic cutaneous tissue samples, wherein a decrease in expression of one or more of a gene of Table A, and an increase in expression of one or more of a gene of Table B, relative to expression of the five or more genes in the reference set, indicates an increased likelihood that the test sample is from a metastatic melanoma and/or indicates a poor prognosis. The method can further include determining that the patient should undergo a treatment protocol. For example, patients for which the melanoma sample expression is indicative of a metastatic melanoma may elect to undergo a more aggressive treatment, e.g., with interferon alpha 2b, or interleukin2, surgery to remove additional tissue (e.g., addition melanoma tissue at the site from which the original sample was obtained, or at another site, e.g., in a lymph node), or an experimental treatment. Patients in which expression is not indicative of a metastatic melanoma may elect to forgo a treatment.

The non-metastatic cutaneous tissue samples (e.g., the reference samples to which expression in the test sample is compared) can include one or more of the following: normal human epithelial melanocytes, primary cutaneous melanoma, basal cell carcinoma, squamous cell carcinoma, melanoma in situ, and/or thin melanoma (<1.5 mm Breslow's thickness).

In various embodiments, expression of the five or more genes is compared to: (a) expression in a first reference set of non-metastatic cutaneous tissue samples, and (b) expression in a second reference set of metastatic melanoma tissue samples; wherein a greater similarity in expression of the five or more genes in the test sample to the second reference set than to the first reference set indicates an increased likelihood that the test sample is a metastatic melanoma.

The determining expression of five or more genes in the test sample can include isolating RNA from the test sample, and detecting expression of the RNA. RNA expression can be detected directly or indirectly, e.g., using microarray or PCR analysis. The sample can be a fixed, paraffin-embedded biopsy sample, or a frozen sample.

In various embodiments, the determining expression of five or more genes in the test sample includes reverse transcriptase polymerase chain reaction (RT-PCR), e.g., quantitative PCR, e.g., real time quantitative PCR.

In various embodiments, the determining expression of five or more genes in the test sample includes microarray analysis.

In other embodiments, the determining expression of five or more genes in the test sample includes analysis of protein expression, e.g., immunohistochemical analysis of proteins encoded by on or more of the genes, or proteomic analysis.

The test sample can be a test sample from a melanoma having an intermediate thickness (e.g., a Breslow's thickness of 1-4 mm). The test sample can be from a thin or thick melanoma.

In another aspect, the technology features a method of evaluating a melanoma from a patient, which method includes, for example, determining expression of five or more genes in a test sample from the melanoma, relative to a control, wherein the five or more genes are selected from the genes listed in Table C and Table D, thereby evaluating the melanoma. The method can include other features described herein. For example, expression of at least 10, 25, 50, 75, or 100 genes from Tables C and D can determined. Expression of no more than 100, 75, 50, 25, or 10 genes can be determined. The at least 5 genes from Table C and Table D may be examined in any combination, such as one gene from Table C and four genes from Table D; or four genes from Table C and one gene from Table D. In some embodiments, expression of genes solely from just one of Table C or Table D is determined (e.g., expression of at least five genes from Table C is determined, or expression of at least five genes from Table D is determined).

Expression of the five or more genes can be determined relative to expression of the five or more genes in a reference set of non-metastatic cutaneous tissue samples, wherein a decrease in expression of one or more of a gene of Table C, and an increase in expression of one or more of a gene of Table D, relative to expression of the five or more genes in the reference set, indicates an increased likelihood that the test sample is a metastatic melanoma and/or indicates a poor prognosis. The method can further include determining that the patient should undergo a treatment protocol, based on the determination of gene expression.

In some embodiments expression of the five or more genes is compared to: (a) expression in a first reference set of non-metastatic cutaneous tissue samples, and (b) expression in a second reference set of metastatic melanoma tissue samples; wherein a greater similarity in expression of the five or more genes in the test sample to the second reference set than to the first reference set indicates an increased likelihood that the test sample is a metastatic melanoma.

The determining expression of five or more genes in the test sample can include isolating RNA from the test sample, and detecting expression of the RNA, or detecting protein expression.

In another aspect, the technology also features kits for evaluating a melanoma sample. The kits include polynucleotides (e.g., primers or probes) for analysis of at least 5, 10, 25, 50, 75, or 100 genes from Tables C and D, wherein each oligonucleotide specifically hybridizes to one of the genes from Tables C and D. The kits can include polynucleotides for analysis of up to 25, 50, 75, or 100 genes from Tables C and D.

For example, a kit includes pairs of polynucleotides for amplification of the genes from Tables C and D by PCR.

The technology also features kits for evaluating a melanoma sample that include polynucleotides (e.g., primers or probes) for analysis of at least 250, 500, 750, 1000, 1250, or 1500 genes from Tables A and B, wherein each oligonucleotide specifically hybridizes to one of the genes from Tables A and B. The kits can include polynucleotides for analysis of up to 250, 500, 270, 1000, 1250, or 1500 genes from Tables A and B. In some embodiments, the polynucleotides are immobilized on a solid support, e.g., as in a microarray.

The technology also features kits for evaluating protein expression in a melanoma sample. The kit includes, for example, reagents (e.g., antibodies) for detection of proteins encoded by at least 5, 10, 25, or 50 genes from Tables C and D.

A "sample" is any biological material obtained from an individual. A "melanoma sample" or "melanoma tissue sample" is a sample that includes primarily melanoma cells.

"Gene" refers to a polynucleotide sequence that comprises sequences that are expressed in a cell as RNA and control sequences necessary for the production of a transcript or precursor. A gene expression product analyzed according to a method described herein can be encoded by a full length coding sequence or by any portion of the coding sequence.

"Polynucleotide" refers to a polymeric form of nucleotides of any length, either ribonucleotides or deoxyribonucleotides. Thus, the term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases, as well as polynucleotides that have been modified in order to introduce a means for attachment (e.g., to a support for use as a microarray).

The descriptions herein are phrased in terms of "five or more" or "ten or more" genes, but the choices of five and ten would be understood to be for the purposes of illustration and are non-limiting. One may also examine expression of other numbers such as 3, 4, 6, 7, 8, 9, 11, 12, 13, 14, 15, 16, 17, 18, 19, 20, 25, and 30 genes, and so forth. In some embodiments, the combination of genes from Tables A, B, C, and/or D which is examined includes one or more genes implicated in one or more (e.g., 2, 3, 4, 5, 6, 7, 8, or 9) of the following biological processes, as understood by one skilled in the art: keratinocyte differentiation, epidermis development, melanocyte differentiation, cell differentiation, morphogenesis, muscle development, nervous system development, cell adhesion, the Wnt receptor signaling pathway, cell-cell signaling, cytoskeleton organization and biogenesis, inflammatory or immune response, cell motility and chemotaxis, electron transport, carbohydrate metabolism, lipid metabolism, proteolysis, signal transduction, protein transport, protein biosynthesis, transcription, DNA repair, cell cycle regulation or proliferation, or apoptosis. In some embodiments, at least one gene implicated in each of the above processes is examined.

The details of one or more embodiments of the technology are set forth in the accompanying drawings and the description below. Other features, objects, and advantages of the technology will be apparent from the description and drawings, and from the claims. All cited patents, and patent applications and references (including references to public sequence database entries) are incorporated by reference in their entireties for all purposes.

DESCRIPTION OF DRAWINGS

FIG. 3A is a table listing results of semi-quantitative. RT-PCR analysis of oncogene and tumor suppressor gene (TSG) mRNA expression in normal human skin, NHEM, PCM and MM cell lines. A panel of 12 putative oncogenes and 6 TSG were analyzed, with the relative levels of mRNA expression as follows: negative band (−), faintly visible band (+/−), visible band (+), strongly visible band (++), N=Not Done. β-actin served as the internal comparative control. The grey values of PCR products of each gene were analyzed by the AlphaEase 3 software and standardized according to β-actin in every sample.

DETAILED DESCRIPTION

Figure 1A:
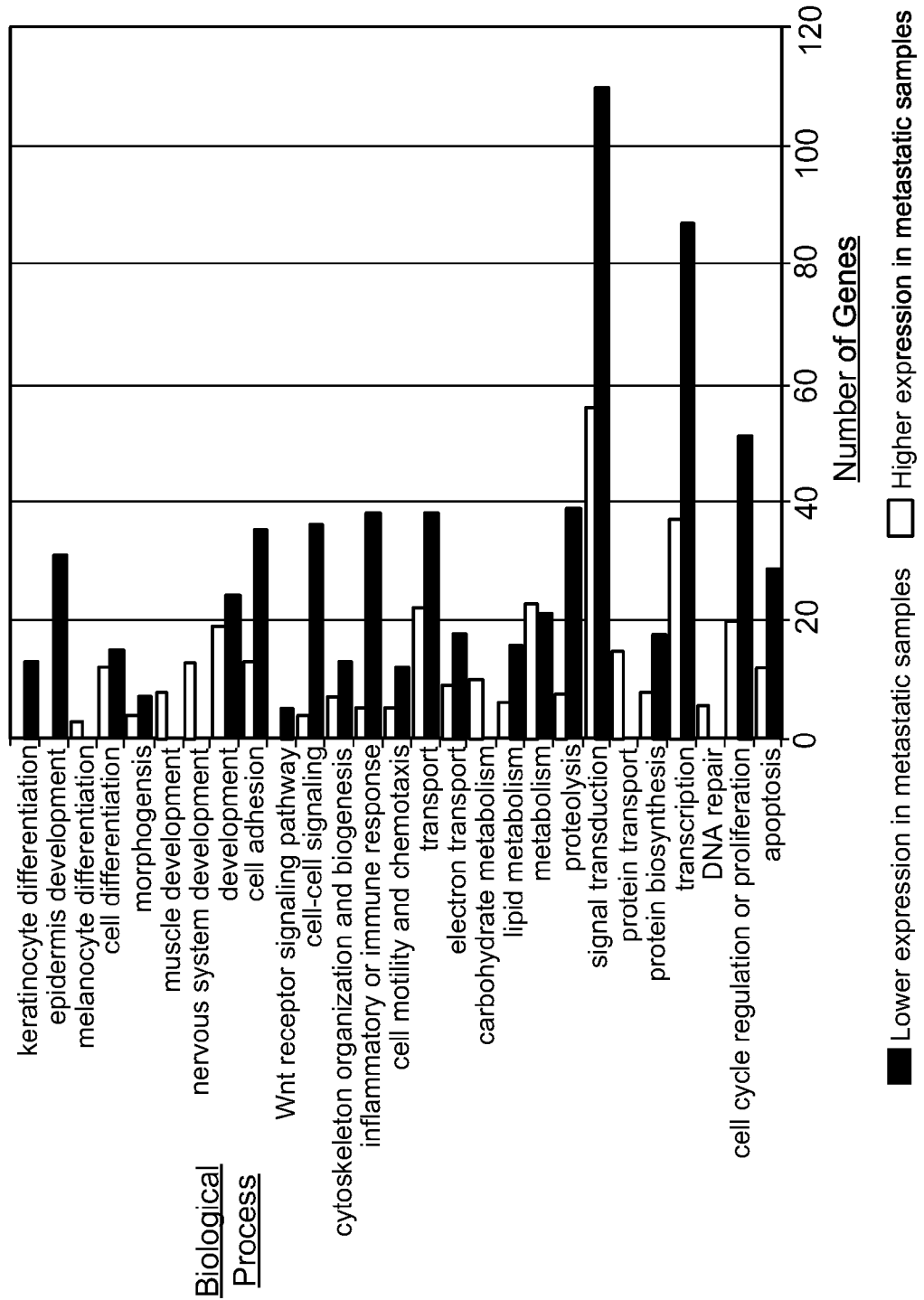
FIG. 1A is a graph depicting the number and functional classifications of genes, lower expression (upper bar for each classification) and higher expression (lower bar for each classification) of which is associated with metastatic melanoma.

Methods and compositions for evaluating tissue samples (e.g., cutaneous tissue samples, e.g., samples from primary melanomas) are provided herein to determine whether the samples exhibit a gene expression profile characteristic of aggressive, metastatic melanomas, or a profile characteristic of non-metastatic melanomas. The ability to classify samples with a high degree of accuracy and sensitivity facilitates prognosis and subsequent clinical decisions (e.g., whether or not to undergo further surgery or other treatment modalities). Accordingly, the technology provides, inter alia, sets of genes whose expression can be examined to determine whether a cutaneous tissue sample is non-metastatic, or metastatic, as well as methods of analyzing expression of the gene sets, and compositions for performing the analysis.

The technology herein features combinations of genes, e.g., combinations of genes listed in Tables A and B below, combinations of genes listed in Tables C and D below. Analysis of the expression of these genes can be performed to identify metastatic melanoma tumors (e.g., in primary cutaneous melanoma samples, or in samples from compound nevi). The technology also features methods of analyzing the expression of combinations of genes. Various techniques are suitable for analyzing gene expression, including those that measure RNA or protein expression. For example, a sample from a melanoma (e.g., a primary cutaneous melanoma) is collected and processed to obtain RNA, protein, or tissue sections, to produce a test sample for analysis. The relative expression of several, dozens, 50, 100, or hundreds of genes in the test sample is determined. The gene expression values are compared to a reference set of values derived from selected non-metastatic melanoma samples and metastatic melanoma samples measured by the same assay as used to determine expression in the test sample. The values obtained for the test sample characterize the sample as metastatic or non-metastatic.

In some methods, a small number of genes (e.g., a subset of genes from Tables C and D, e.g., 5, 10, 15, 25 genes) is selected for analysis, and expression levels are determined by a quantitative or semi-quantitative PCR method or by immunohistochemistry. The combination of measured values for the respective genes are compared to control values to determine the degree to which the test sample contains gene expression values indicative of a metastatic tumor sample. The test samples are, for example, surgically collected tumors collected in a manner that preserves RNA, or alternatively fixed (e.g., formalin fixed) and embedded in paraffin prior to analysis, preserved by flash freezing or fixation, and/or treated with an RNA Stabilization Reagent.

In some methods, expression of a larger number of genes is analyzed, e.g., using microarrays. Nucleic acids from the test sample are hybridized to arrays under appropriate conditions, arrays are scanned, and the data processed by standard methods for feature extraction and normalization in order to obtain individual gene expression values. In these methods, a few hundred to more than a thousand genes can be used to determine the character of the test sample. One of several methods might be employed to identify the metastatic potential of the sample under investigation, based on the microarray-determined gene expression values. Typically, reference samples for metastatic melanoma and non-metastatic melanoma are analyzed in advance. The test sample is compared to the reference samples by classification schemes such as clustering, weighted voting, principle components analysis, self organizing maps, and/or neural networks. Each of these schemes is essentially a mathematical system for maximizing the geometric separation of classes (metastatic and non-metastatic) in multidimensional space using the individual gene expression values as coordinates to plot an individual sample relative to reference samples in multidimensional space.

Whether a method suitable for analysis of smaller or larger numbers of genes is employed, the reference samples define the combination of measures that identify a metastatic sample and a non-metastatic sample. The specific mathematical process depends on the method used for measuring gene expression, the number of genes, and the nature of the genes chosen to participate in the assay. Based on this unique combination and the reference sample values a threshold value will be determined (or mathematical formula) that will identify the unknown sample as more like the metastatic samples or more like the non-metastatic samples. One of skill would understand that genes that are not differentially expressed can be examined in methods described herein, e.g., as a control.

Tables A-D set forth sets of genes, the expression of which has been shown to correlate with metastatic melanoma. Tables A and C list genes whose expression is decreased in metastatic melanoma samples, relative to non-metastatic samples. Tables B and D list genes whose expression is increased in metastatic melanoma samples, relative to non-metastatic samples. Thus, the genes provided in these tables, and subsets thereof, are useful markers for metastatic melanoma.

In various embodiments, the technology provides a subset of genes from Tables A and B for evaluating a cutaneous tissue sample, sets of oligonucleotides (e.g., for use as probes and primers) for analyzing expression of the subsets, and methods for analyzing their expression, as described in more detail below. The set includes, for example, at least 5, 10, 50, 100, 250, 500, 750, or 1000 genes from Tables A and B, in any proportion (e.g., 800 genes from Table A and 200 genes from Table B).

For example, the subset includes the genes listed in Tables C and D. The genes in Tables C and D, and subsets thereof, are useful for evaluating a cutaneous-tissue sample, and in methods for analyzing expression of the subsets, as described in more detail below. An exemplary set includes, for example, at least 5, 10, 25, 35, or 51 genes from each of Tables C and D.

The lists shown in Tables C and D were generated from the lists shown in Tables A and B by selecting the genes that exhibit the greatest difference in gene expression between the metastatic samples and the non-metastatic samples based on microarray analysis. The genes on these lists also represent genes, the expression or expression products of which have been the subject of biological investigations.

Tables A-D include full length gene names (Gene description), gene symbols, GenBank accession numbers (GenBank ID), Entrez gene accession numbers (Entrez Gene ID), and UniGene accession numbers (UniGene ID). GenBank, Entrez, and UniGene records can be accessed on the World Wide Web at the following address: ncbi.nlm.nih.gov. These records provide sequences and additional information for each gene.

The genes listed in Tables A-D are generally referred to elsewhere herein by gene symbol. Gene symbols shown in parentheses are aliases or former designations.

TABLE A

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 1. | 24-dehydrocholesterol reductase | DHCR24 | NM_014762.2 | 1718 | Hs.498727 |
| 2. | 26 serine protease | P11 | NM_006025.2 | 8909 | Hs.997 |
| 3. | abhydrolase domain containing 9 | ABHD9 | NM_024794.1 | 79852 | Hs.156457 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 4. | ABI gene family, member 3 (NESH) binding protein | ABI3BP | NM_015429.2 | 25890 | Hs.477015 |
| 5. | absent in melanoma 1 | AIM1 | NM_001624.1 | 202 | Hs.486074 |
| 6. | absent in melanoma 1-like | AIM1L | NM_017977 | 55057 | Hs.128738 |
| 7. | acid phosphatase, prostate | ACPP | NM_001099.2 | 55 | Hs.433060 |
| 8. | Acrg embryonic lethality (mouse) minimal region ortholog | AK000009 | AA425275 | 170622 | Hs.356605 |
| 9. | actin binding LIM protein 1 | ABLIM1 | NM_001003407.1 | 3983 | Hs.438236 |
| 10. | activin A receptor, type IIA | ACVR2A | NM_001616.3 | 92 | Hs.470174 |
| 11. | adaptor-related protein complex 1, mu 2 subunit | AP1M2 | NM_005498.3 | 10053 | Hs.18894 |
| 12. | adenosine kinase | ADK | NM_001123.2 | 132 | Hs.500118 |
| 13. | ADMP | ADMP | NM_145035 | 165679 | Hs.369104 |
| 14. | AFG3 ATPase family gene 3-like 2 (yeast) | AFG3L2 | NM_006796 | 10939 | Hs.436683 |
| 15. | AHNAK nucleoprotein (desmoyokin) | AHNAK | NM_024060 | 79026 | Hs.378738 |
| 16. | aldehyde dehydrogenase 2 family (mitochondrial) | ALDH2 | NM_000690.2 | 217 | Hs.436437 |
| 17. | aldehyde dehydrogenase 3 family, member A2 | ALDH3A2 | NM_000382.2 | 224 | Hs.499886 |
| 18. | aldehyde dehydrogenase 3 family, member B2 | ALDH3B2 | NM_000695.3 | 222 | Hs.87539 |
| 19. | aldehyde dehydrogenase 3 family, memberA1 | ALDH3A1 | NM_000691.3 | 218 | Hs.531682 |
| 20. | aldo-keto reductase family 1, member B10 (aldose reductase) | AKR1B10 | NM_020299.3 | 57016 | Hs.116724 |
| 21. | aldo-keto reductase family 1, member C1 (dihydrodiol dehydrogenase 1; 20-alpha (3-alpha)-hydroxysteroid dehydrogenase) | AKR1C1 | NM_001353 | 1645 | Hs.295131 |
| 22. | aldo-keto reductase family 1, member C2 (dihydrodiol dehydrogenase 2; bile acid binding protein; 3-alpha hydroxysteroid dehydrogenase, type III) | AKR1C2 | NM_001354.4 | 1646 | Hs.558319 |
| 23. | alkaline ceramidase | ACER1 | NM_133492 | 125981 | Hs.352609 |
| 24. | alpha-2-glycoprotein 1, zinc | AZGP1 | NM_001185 | 563 | Hs.407861 |
| 25. | alpha-2-macroglobulin-like 1 | A2ML1 | AK057908.1 | 144568 | Hs.334306 |
| 26. | ALS2 C-terminal like | ALS2CL | NM_147129.2 | 259173 | Hs.517937 |
| 27. | androgen receptor (dihydrotestosterone receptor; testicular feminization; spinal and bulbar muscular atrophy; Kennedy disease) | AR | NM_001011645.1 | 367 | Hs.496240 |
| 28. | ankyrin 3, node of Ranvier (ankyrin G) | ANK3 | NM_001149.2 | 288 | Hs.499725 |
| 29. | ankyrin repeat domain 22 | ANKRD22 | NM_144590.1 | 118932 | Hs.217484 |
| 30. | ankyrin repeat domain 35 | ANKRD35 | NM_144698.2 | 148741 | Hs.133081 |
| 31. | annexin A3 | ANXA3 | NM_005139 | 306 | Hs.480042 |
| 32. | annexin A8 | ANXA8 | NM_001630 | 244 | Hs.87268 |
| 33. | annexin A9 | ANXA9 | NM_003568.1 | 8416 | Hs.430324 |
| 34. | aquaporin 3 | AQP3 | NM_004925 | 360 | Hs.234642 |
| 35. | arachidonate 12-lipoxygenase | ALOX12 | NM_000697.1 | 239 | Hs.422967 |
| 36. | arachidonate 12-lipoxygenase, 12R type | ALOX12B | NM_001139.1 | 242 | Hs.136574 |
| 37. | arachidonate lipoxygenase 3 | ALOXE3 | NM_021628.1 | 59344 | Hs.232770 |
| 38. | arginase, liver | ARG1 | NM_000045.2 | 383 | Hs.440934 |
| 39. | argininosuccinate synthetase | ASS | NM_054012.2 | 445 | Hs.558301 |
| 40. | arrestin domain containing 4 | ARRDC4 | NM_183376.1 | 91947 | Hs.6093 |
| 41. | aryl hydrocarbon receptor nuclear translocator-like 2 | ARNTL2 | NM_020183 | 56938 | Hs.434269 |
| 42. | arylacetamide deacetylase(esterase) | AADAC | NM_001086.2 | 13 | Hs.506908 |
| 43. | arylacetamide deacetylase-like 2 | AADACL2 | NM_207365.1 | 344752 | Hs.100206 |
| 44. | ataxin 3 | ATXN3 | NM_001024631.1 | 4287 | Hs.526425 |
| 45. | ATPase type 13A4 | ATP13A4 | NM_032279.2 | 84239 | Hs.561100 |
| 46. | ATPase type 13A5 | ATP13A5 | AY358667.1 | 344905 | Hs.531335 |
| 47. | ATPase, Ca++ transporting, type 2C, member 2 | ATP2C2 | NM_014861.1 | 9914 | Hs.6168 |
| 48. | ATPase, Class 1, type 8B, member 1 | ATP8B1 | NM_005603 | 5205 | Hs.418426 |
| 49. | ATPase, H+ transporting, lysosomal 42 kDa, V1 subunit C isoform 2 | ATP6V1C2 | NM_001039362.1 | 245973 | Hs.372429 |
| 50. | ATPase, H+/K+ transporting, nongastric, alpha polypeptide | ATP12A | NM_001676.4 | 479 | Hs.147111 |
| 51. | ATP-binding cassette, sub-family A (ABC), member 12 | ABCA12 | NM_173076.2 | 26154 | Hs.134585 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 52. | autism susceptibility candidate 2 | AUTS2 | NM_015570.1 | 26053 | Hs.21631 |
| 53. | bactericidal/permeability-increasing protein-like 2 | BPIL2 | NM_174932 | 254240 | Hs.372939 |
| 54. | basonuclin 1 | BNC1 | NM_001717.2 | 646 | Hs.459153 |
| 55. | B-box and SPRY domain containing | BSPRY | NM_017688.1 | 54836 | Hs.494870 |
| 56. | B-cell CLL/lymphoma 11A (zinc finger protein) | BCL11A | NM_138559.1 | 53335 | Hs.370549 |
| 57. | B-cell CLL/lymphoma 11B (zinc finger protein) | BCL11B | NM_022898.1 | 64919 | Hs.510396 |
| 58. | BCL2/adenovirus E1B 19 kD interacting protein like | BNIPL | AY033000.1 | 149428 | Hs.553613 |
| 59. | BCL2-associated athanogene | BAG1 | NM_004323.3 | 573 | Hs.377484 |
| 60. | BCL2-like 10 (apoptosis facilitator) | BCL2L10 | NM_020396.2 | 10017 | Hs.283672 |
| 61. | betacellulin | BTC | NM_001729.1 | 685 | Hs.558302 |
| 62. | bleomycin hydrolase | BLMH | NM_000386.2 | 642 | Hs.371914 |
| 63. | Boc homolog (mouse) | BOC | NM_033254.2 | 91653 | Hs.556004 |
| 64. | bradykinin receptor B2 | BDKRB2 | NM_000623.2 | 624 | Hs.525572 |
| 65. | BRG1-binding protein ELD/OSA1 | ELD/OSA1 | NM_020732 | 57492 | Hs.436008 |
| 66. | BTB (POZ) domain containing 11 | BTBD11 | NM_001017523.1 | 121551 | Hs.271272 |
| 67. | BTG family, member 3 | BTG3 | NM_006806 | 10950 | Hs.473420 |
| 68. | butyrobetaine (gamma), 2-oxoglutarate dioxygenase (gamma-butyrobetaine hydroxylase) 1 | BBOX1 | NM_003986 | 8424 | Hs.144845 |
| 69. | cadherin-like 22 | CDH22 | NM_021248 | 64405 | Hs.382126 |
| 70. | cadherin-like 26 | CDH26 | NM_021810.3 | 60437 | Hs.54973 |
| 71. | calcium channel, voltage-dependent, alpha 2/delta 3 subunit | CACNA2D3 | NM_018398.2 | 55799 | Hs.128594 |
| 72. | calcium channel, voltage-dependent, beta 4 subunit | CACNB4 | NM_001005746.1 | 785 | Hs.284800 |
| 73. | calcium/calmodulin-dependent protein kinase ID | CAMK1D | NM_020397.2 | 57118 | Hs.156723 |
| 74. | calmodulin-like 3 | CALML3 | NM_005185 | 810 | Hs.239600 |
| 75. | calmodulin-like 5 | CALML5 | NM_017422.3 | 51806 | Hs.180142 |
| 76. | calpain small subunit 2 | CAPNS2 | NM_032330 | 84290 | Hs.13359 |
| 77. | carbonic anhydrase II | CA2 | NM_000067.1 | 760 | Hs.155097 |
| 78. | carbonic anhydrase XII | CA12 | NM_001218.3 | 771 | Hs.210995 |
| 79. | carbonic anhydrase XIII | CA13 | NM_198584.1 | 377677 | Hs.127189 |
| 80. | carboxypeptidase A4 | CPA4 | NM_016352 | 51200 | Hs.93764 |
| 81. | carboxypeptidase Z | CPZ | NM_001014447.1 | 8532 | Hs.78068 |
| 82. | carcinoembryonic antigen-related cell adhesion molecule 19 | CEACAM19 | BC083499.1 | 56971 | Hs.416925 |
| 83. | carcinoembryonic antigen-related cell adhesion molecule 6 (non-specific cross reacting antigen) | CEACAM6 | NM_002483.3 | 4680 | Hs.466814 |
| 84. | Cas-Br-M (murine) ecotropic retroviral transforming sequence c | CBLC | NM_012116.2 | 23624 | Hs.466907 |
| 85. | casein kinase 1, alpha 1 | CSNK1A1 | NM_001892 | 1452 | Hs.442592 |
| 86. | caspase 14, apoptosis-related cysteine protease | CASP14 | NM_012114 | 23581 | Hs.248226 |
| 87. | caspase recruitment domain family, member 14 | CARD14 | NM_024110 | 79092 | Hs.550529 |
| 88. | castor homolog 1, zinc finger (Drosophila) | CASZ1 | NM_017766.2 | 54897 | Hs.439894 |
| 89. | catenin, beta interacting protein 1 | CTNNBIP1 | NM_020248.2 | 56998 | Hs.463759 |
| 90. | cathepsin L2 | CTSL2 | NM_001333.2 | 1515 | Hs.87417 |
| 91. | CCAAT/enhancer binding protein (C/EBP), alpha | CEBPA | NM_004364.2 | 1050 | Hs.76171 |
| 92. | CD1a antigen | CD1A | NM_001763.1 | 909 | Hs.1309 |
| 93. | CD1E antigen, e polypeptide | CD1E | NM_030893.1 | 913 | Hs.249217 |
| 94. | CD207 antigen, langerin | CD207 | NM_015717.2 | 50489 | Hs.199731 |
| 95. | CD24 antigen (small cell lung carcinoma cluster 4 antigen) | CD24 | NM_013230.2 | 934 | Hs.375108 |
| 96. | CDC-like kinase 4 | CLK4 | NM_020666 | 57396 | Hs.406557 |
| 97. | CDP-diacylglycerol synthase (phosphatidate cytidylyltransferase) 1 | CDS1 | NM_001263.2 | 1040 | Hs.444924 |
| 98. | cellular retinoic acid binding protein 2 | CRABP2 | NM_001878.2 | 1382 | Hs.405662 |
| 99. | centaurin, delta 1 | CENTD1 | NM_015230 | 116984 | Hs.427719 |
| 100. | checkpoint suppressor 1 | CHES1 | NM_005197 | 1112 | Hs.434286 |
| 101. | chemokine (C-C motif) ligand 22 | CCL22 | NM_002990.3 | 6367 | Hs.534347 |
| 102. | chemokine (C-X3-C motif) receptor 1 | CX3CR1 | NM_001337 | 1524 | Hs.78913 |
| 103. | chemokine (C-X-C motif) ligand 14 | CXCL14 | NM_004887.3 | 9547 | Hs.483444 |
| 104. | chitinase 3-like 2 | CHI3L2 | NM_001025197.1 | 1117 | Hs.514840 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 105. | chloride channel, calcium activated, family member 2 | CLCA2 | NM_006536 | 9635 | Hs.241551 |
| 106. | chloride channel, calcium activated, family member 4 | CLCA4 | NM_012128.2 | 22802 | Hs.555012 |
| 107. | chloride intracellular channel 3 | CLIC3 | NM_004669.2 | 9022 | Hs.64746 |
| 108. | cholinergic receptor, nicotinic, alpha polypeptide 9 | CHRNA9 | NM_017581.2 | 55584 | Hs.272278 |
| 109. | chromatin modifying protein 4C | CHMP4C | NM_152284.3 | 92421 | Hs.183861 |
| 110. | chromosome 1 open reading frame 106 | C1orf106 | NM_018265.1 | 55765 | Hs.518997 |
| 111. | chromosome 1 open reading frame 116 | C1orf116 | NM_023938.4 | 79098 | Hs.32417 |
| 112. | chromosome 1 open reading frame 161 | C1orf161 | NM_152367.1 | 126868 | Hs.376194 |
| 113. | chromosome 1 open reading frame 172 | C1orf172 | NM_152365.1 | 126695 | Hs.188881 |
| 114. | Chromosome 1 open reading frame 21 | C1orf21 | NM_030806.3 | 81563 | Hs.497159 |
| 115. | chromosome 1 open reading frame 210 | C1orf210 | NM_182517.1 | 149466 | Hs.158963 |
| 116. | chromosome 1 open reading frame 42 | C1orf42 | NM_019060.1 | 54544 | Hs.110196 |
| 117. | chromosome 1 open reading frame 46 | C1orf46 | AF005082 | 388699 | Hs.516420 |
| 118. | chromosome 1 open reading frame 68 | C1orf68 | AF005081.1 | 553168 | Hs.547272 |
| 119. | chromosome 10 open reading frame 118 | C10orf118 | NM_018017.2 | 55088 | Hs.159066 |
| 120. | chromosome 10 open reading frame 57 | C10orf57 | NM_025125.2 | 80195 | Hs.169982 |
| 121. | chromosome 10 open reading frame 72 | C10orf72 | NM_144984.1 | 196740 | Hs.522928 |
| 122. | chromosome 10 open reading frame 99 | C10orf99 | NM_207373.1 | 387695 | Hs.298713 |
| 123. | chromosome 11 open reading frame 52 | C11orf52 | NM_080659.1 | 91894 | Hs.97013 |
| 124. | chromosome 14 open reading frame 116 | C14orf116 | NM_018589 | 55453 | Hs.60548 |
| 125. | chromosome 14 open reading frame 29 | C14orf29 | NM_181533 | 145447 | Hs.271896 |
| 126. | chromosome 14 open reading frame 47 | C14orf47 | NM_152332 | 123036 | Hs.57787 |
| 127. | chromosome 14 open reading frame 78 | C14orf78 | AK094143.1 | 113146 | Hs.441783 |
| 128. | chromosome 19 open reading frame 33 | C19orf33 (IMUP) | NM_033520.1 | 64073 | Hs.348553 |
| 129. | chromosome 2 open reading frame 54 | C2orf54 | NM_024861.1 | 79919 | Hs.193745 |
| 130. | chromosome 2 open reading frame 55 | C2orf55 | NM_207362.1 | 343990 | Hs.469398 |
| 131. | chromosome 20 open reading frame 128 | C20orf128 | NM_178468.2 | 128876 | Hs.554917 |
| 132. | chromosome 20 open reading frame 38 | C20orf38 | NM_018327.1 | 55304 | Hs.272242 |
| 133. | chromosome 20 open reading frame 42 | C20orf42 | NM_017671.3 | 55612 | Hs.472054 |
| 134. | chromosome 20 open reading frame 55 | C20orf55 | NM_031424 | 83541 | Hs.534072 |
| 135. | chromosome 20 open reading frame 74 | C20orf74 | AK002211.1 | 57186 | Hs.472285 |
| 136. | chromosome 21 open reading frame 34 | C21orf34 | NM_001005733.1 | 388815 | Hs.473394 |
| 137. | chromosome 4 open reading frame 32 | C4orf32 | NM_152400.1 | 132720 | Hs.23439 |
| 138. | chromosome 5 open reading frame 27 | C5orf27 | NM_175616.2 | 202299 | Hs.8373 |
| 139. | Chromosome 5 open reading frame 4 | C5orf4 | NM_016348.1 | 10826 | Hs.519694 |
| 140. | chromosome 6 open reading 132 | C6orf132 | XM_371820 | 647024 | Hs.444277 |
| 141. | chromosome 6 open reading frame 143 | C6orf143 | NM_001010872.1 | 222584 | Hs.258095 |
| 142. | chromosome 6 open reading frame 162 | C6orf162 | NM_020425 | 57150 | Hs.70769 |
| 143. | chromosome 8 open reading frame 47 | C8orf47 | NM_173549.1 | 203111 | Hs.171455 |
| 144. | chromosome 8 open reading frame 61 | C8orf61 | NM_001034061.1 | 619435 | Hs.127675 |
| 145. | chromosome 9 open reading frame 111 | C9orf111 | NM_152286.2 | 375775 | Hs.294147 |
| 146. | chromosome 9 open reading frame 3 | C9orf3 | NM_032823.3 | 84909 | Hs.434253 |
| 147. | clathrin, light polypeptide (Lcb) | CLTB | NM_007097.2 | 1212 | Hs.484241 |
| 148. | claudin 1 | CLDN1 | NM_021101.3 | 9076 | Hs.439060 |
| 149. | claudin 4 | CLDN4 | NM_001305.3 | 1364 | Hs.520942 |
| 150. | claudin 8 | CLDN8 | NM_199328.1 | 9073 | Hs.162209 |
| 151. | coagulation factor II (thrombin) receptor-like 1 | F2RL1 | NM_005242.3 | 2150 | Hs.154299 |
| 152. | coagulation factor III (thromboplastin, tissue factor) | F3 | NM_001993.2 | 2152 | Hs.62192 |
| 153. | COBL-like 1 | COBLL1 | NM_014900.3 | 22837 | Hs.470457 |
| 154. | coiled-coil domain containing 3 | CCDC3 | NM_031455.2 | 83643 | Hs.498720 |
| 155. | collagen, type VII, alpha 1 (epidermolysis bullosa, dystrophic, dominant and recessive) | COL7A1 | NM_000094.2 | 1294 | Hs.476218 |
| 156. | collagen, type XVII, alpha 1 | COL17A1 | NM_130778.1 | 1308 | Hs.117938 |
| 157. | collagen, type XXI, alpha 1 | COL21A1 | NM_030820.3 | 81578 | Hs.47629 |
| 158. | contactin 1 | CNTN1 | NM_001843 | 1272 | Hs.143434 |
| 159. | cordon-bleu homolog (mouse) | COBL | NM_015198.2 | 23242 | Hs.99141 |
| 160. | corneodesmosin | CDSN | NM_001264.3 | 1041 | Hs.310958 |
| 161. | cornifelin | CNFN | NM_032488.2 | 84518 | Hs.148590 |
| 162. | coxsackie virus and adenovirus receptor | CXADR | NM_001338.3 | 1525 | Hs.473417 |
| 163. | creatine kinase, mitochondrial 1A | CKMT1A | NM_001015001.1 | 548596 | Hs.425633 |
| 164. | crumbs homolog 3 (*Drosophila*) | CRB3 | NM_174881.2 | 92359 | Hs.150319 |
| 165. | cryptochrome 2 (photolyase-like) | CRY2 | NM_021117.1 | 1408 | Hs.532491 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 166. | C type lectin domain family 2, member B | CLEC2B | NM_005127.2 | 9976 | Hs.85201 |
| 167. | cyclic nucleotide gated channel beta 1 | CNGB1 | NM_001297.1 | 1258 | Hs.147062 |
| 168. | cylindromatosis (turban tumor syndrome) | CYLD | NM_015247 | 1540 | Hs.432993 |
| 169. | cystatin A (stefin A) | CSTA | NM_005213.3 | 1475 | Hs.518198 |
| 170. | cystatin E/M | CST6 | NM_001323.2 | 1474 | Hs.139389 |
| 171. | cysteine rich transmembrane BMP regulator 1 (chordin-like) | CRIM1 | NM_016441.1 | 51232 | Hs.332847 |
| 172. | cysteine/tyrosine-rich 1 | CYYR1 | NM_052954.2 | 116159 | Hs.37445 |
| 173. | cysteine-rich protein 1 (intestinal) | CRIP1 | NM_001311.3 | 1396 | Hs.70327 |
| 174. | cysteine-rich secretory protein 3 | CRISP3 | NM_006061.1 | 10321 | Hs.404466 |
| 175. | cytidine deaminase | CDA | NM_001785.2 | 978 | Hs.466910 |
| 176. | cytochrome b5 type A (microsomal) | CYB5A | NM_001914.2 | 1528 | Hs.465413 |
| 177. | cytochrome P450, family 2, subfamily C, polypeptide 18 | CYP2C18 | NM_000772.1 | 1562 | Hs.511872 |
| 178. | cytochrome P450, family 2, subfamily E, polypeptide 1 | CYP2E1 | NM_000773.3 | 1571 | Hs.12907 |
| 179. | cytochrome P450, family 26, subfamily B, polypeptide 1 | CYP26B1 | NM_019885.2 | 56603 | Hs.91546 |
| 180. | cytochrome P450, family 3, subfamily A, polypeptide 5 | CYP3A5 | NM_000777.2 | 1577 | Hs.150276 |
| 181. | cytochrome P450, family 3, subfamily A, polypeptide 7 | CYP3A7 | NM_000765.2 | 1551 | Hs.111944 |
| 182. | cytochrome P450, family 39, subfamily A, polypeptide 1 | CYP39A1 | NM_016593.3 | 51302 | Hs.387367 |
| 183. | cytochrome P450, family 4, subfamily F, polypeptide 12 | CYP4F12 | NM_023944.1 | 66002 | Hs.131459 |
| 184. | cytochrome P450, family 4, subfamily F, polypeptide 2 | CYP4F2 | NM_001082.3 | 8529 | Hs.558423 |
| 185. | cytochrome P450, family 4, subfamily F, polypeptide 22 | CYP4F22 | NM_173483.1 | 126410 | Hs.156452 |
| 186. | cytochrome P450, family 4, subfamily F, polypeptide 3 | CYP4F3 | NM_000896.1 | 4051 | Hs.106242 |
| 187. | cytochrome P450, family 4, subfamily X, polypeptide 1 | CYP4X1 | NM_178033.1 | 260293 | Hs.439760 |
| 188. | cytokine receptor-like factor 1 | CRLF1 | NM_004750.2 | 9244 | Hs.114948 |
| 189. | cytoplasmic polyadenylation element binding protein 3 | CPEB3 | NM_014912.3 | 22849 | Hs.131683 |
| 190. | death associated protein-like 1 | DAPL1 | NM_001017920.1 | 92196 | Hs.59761 |
| 191. | death-associated protein kinase 2 | DAPK2 | NM_014326.3 | 23604 | Hs.237886 |
| 192. | decorin | DCN | NM_133505.2 | 1634 | Hs.156316 |
| 193. | dedicator of cytokinesis 9 | DOCK9 | NM_015296.1 | 23348 | Hs.314413 |
| 194. | defensin, beta 1 | DEFB1 | NM_005218.1 | 1672 | Hs.32949 |
| 195. | defensin, beta 103A | DEFB103A | NM_018661.2 | 55894 | Hs.283082 |
| 196. | deiodinase, iodothyronine, type II | DIO2 | NM_001007023.1 | 1734 | Hs.202354 |
| 197. | DENN/MADD domain containing 2C | DENND2C | NM_198459.2 | 163259 | Hs.127350 |
| 198. | dermcidin | DCD | NM_053283.2 | 117159 | Hs.350570 |
| 199. | dermokine | DMKN | NM_033317.2 | 93099 | Hs.417795 |
| 200. | desmocollin 1 | DSC1 | NM_004948 | 1823 | Hs.348436 |
| 201. | desmocollin 2 | DSC2 | NM_004949.2 | 1824 | Hs.95612 |
| 202. | desmocollin 3 | DSC3 | NM_001941 | 1825 | Hs.41690 |
| 203. | desmoglein 1 | DSG1 | NM_001942.1 | 1828 | Hs.2633 |
| 204. | desmoglein 3 (pemphigus vulgaris antigen) | DSG3 | NM_001944.1 | 1830 | Hs.1925 |
| 205. | desmoplakin | DSP | NM_001008844.1 | 1832 | Hs.519873 |
| 206. | DIRAS family, GTP-binding RAS-like 3 | DIRAS3 | NM_004675.2 | 9077 | Hs.194695 |
| 207. | Discs, large homolog 2, chapsyn-110 (Drosophila) | DLG2 | NM_001364.2 | 1740 | Hs.503453 |
| 208. | distal-less homeo box 3 | DLX3 | NM_005220.2 | 1747 | Hs.134194 |
| 209. | DKFZP564O0823 protein | DKFZP564O0823 | NM_015393.2 | 25849 | Hs.105460 |
| 210. | dual adaptor of phosphotyrosine and 3-phosphoinositides | DAPP1 | NM_014395.1 | 27071 | Hs.436271 |
| 211. | dual oxidase 1 | DUOX1 | NM_017434 | 53905 | Hs.272813 |
| 212. | dual oxidase 2 | DUOX2 | NM_014080.3 | 50506 | Hs.71377 |
| 213. | dual oxidase maturation factor 1 | DUOXA1 | NM_144565 | 90527 | Hs.356664 |
| 214. | dynein, light chain, roadblock-type 2 | DYNLRB2 | NM_130897.1 | 83657 | Hs.98849 |
| 215. | dystonin | DST | NM_020388.2 | 667 | Hs.485616 |
| 216. | E74-like factor 5 (ets domain transcription factor) | ELF5 | NM_001422.2 | 2001 | Hs.11713 |
| 217. | Early endosome antigen 1, 162 kD | EEA1 | NM_003566 | 8411 | Hs.403150 |
| 218. | echinoderm microtubule associated protein like 1 | EML1 | NM_001008707.1 | 2009 | Hs.12451 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 219. | ectonucleoside triphosphate diphosphohydrolase 3 | ENTPD3 | NM_001248 | 956 | Hs.441145 |
| 220. | EF-hand calcium binding domain 6 | EFCAB6 | NM_198856.1 | 64800 | Hs.368507 |
| 221. | EGF-like-domain, multiple 3 | EGFL3 | AL134303 | 1953 | Hs.56186 |
| 222. | egl nine homolog 3 (*C. elegans*) | EGLN3 | NM_022073.2 | 112399 | Hs.135507 |
| 223. | EH-domain containing 2 | EHD2 | NM_014601.2 | 30846 | Hs.325650 |
| 224. | electron-transferring-flavoprotein dehydrogenase | ETFDH | NM_004453.1 | 2110 | Hs.155729 |
| 225. | ELL-related RNA polymerase II, elongation factor | ELL2 | NM_012081 | 22936 | Hs.192221 |
| 226. | ELMO domain containing 1 | ELMOD1 | NM_018712.2 | 55531 | Hs.495779 |
| 227. | elongation factor RNA polymerase II-like 3 | ELL3 | NM_025165.2 | 80237 | Hs.424126 |
| 228. | elongation of very long chain fatty acids (FEN1/Elo2, SUR4/Elo3, yeast)-like 4 | ELOVL4 | NM_022726.2 | 6785 | Hs.101915 |
| 229. | ELOVL family member 7, elongation of long chain fatty acids (yeast) | ELOVL7 | NM_024930.1 | 79993 | Hs.274256 |
| 230. | embryonal Fyn-associated substrate | EFS | NM_005864.2 | 10278 | Hs.24587 |
| 231. | empty spiracles homolog 2 (*Drosophila*) | EMX2 | NM_004098.2 | 2018 | Hs.202095 |
| 232. | endothelial differentiation, sphingolipid G-protein-coupled receptor, 8 | EDG8 | NM_030760.3 | 53637 | Hs.501561 |
| 233. | endothelin 1 | EDN1 | NM_001955 | 1906 | Hs.511899 |
| 234. | engulfment and cell motility 3 (ced-12 homolog, *C. elegans*) | ELMO3 | NM_024712.3 | 79767 | Hs.377416 |
| 235. | enoyl Coenzyme A hydratase domain containing 2 | ECHDC2 | NM_018281.1 | 55268 | Hs.476319 |
| 236. | envoplakin | EVPL | NM_001988.1 | 2125 | Hs.500635 |
| 237. | EPH receptor B6 | EPHB6 | NM_004445.2 | 2051 | Hs.380089 |
| 238. | ephrin-A3 | EFNA3 | NM_004952.3 | 1944 | Hs.516656 |
| 239. | epidermal growth factor receptor (erythroblastic leukemia viral (v-erb-b) oncogene homolog, avian) | EGFR | NM_201282.1 | 1956 | Hs.488293 |
| 240. | epidermal retinal dehydrogenase 2 | RDHE2 | NM_138969.2 | 195814 | Hs.170673 |
| 241. | epiplakin 1 | EPPK1 | NM_031308.1 | 83481 | Hs.200412 |
| 242. | epiregulin | EREG | NM_001432 | 2069 | Hs.115263 |
| 243. | epithelial membrane protein 2 | EMP2 | NM_001424.3 | 2013 | Hs.531561 |
| 244. | epithelial V-like antigen 1 | EVA1 | NM_005797.2 | 10205 | Hs.116651 |
| 245. | EPS8-like 1 | EPS8L1 | NM_133180.1 | 54869 | Hs.438862 |
| 246. | EPS8-like 2 | EPS8L2 | NM_022772.2 | 64787 | Hs.55016 |
| 247. | epsin 3 | EPN3 | NM_017957.1 | 55040 | Hs.165904 |
| 248. | erythrocyte membrane protein band 4.1 like 4A | EPB41L4A | NM_022140 | 64097 | Hs.553542 |
| 249. | erythrocyte membrane protein band 4.1 like 4B | EPB41L4B | NM_018424.1 | 54566 | Hs.269180 |
| 250. | erythrocyte membrane protein band 4.1 like 5 | EPB41L5 | NM_020909.2 | 57669 | Hs.369232 |
| 251. | ets homologous factor | EHF | NM_012153.3 | 26298 | Hs.502306 |
| 252. | ets variant gene 7 (TEL2 oncogene) | ETV7 | NM_016135.2 | 51513 | Hs.272398 |
| 253. | eukaryotic elongation factor-2 kinase | EEF2K | NM_013302.3 | 29904 | Hs.498892 |
| 254. | exophilin 5 | EXPH5 | NM_015065.1 | 23086 | Hs.269591 |
| 255. | family with sequence similarity 107, member A | FAM107A | NM_007177.1 | 11170 | Hs.8022 |
| 256. | family with sequence similarity 13, member C1 | FAM13C1 | NM_001001971.1 | 220965 | Hs.499704 |
| 257. | family with sequence similarity 46, member B | FAM46B | NM_052943.2 | 115572 | Hs.59771 |
| 258. | family with sequence similarity 62 (C2 domain containing), member C | FAM62C | BC037292.1 | 83850 | Hs.477711 |
| 259. | family with sequence similarity 79, member B | FAM79B | NM_198485.1 | 285386 | Hs.338851 |
| 260. | family with sequence similarity 83, member A | FAM83A | NM_032899.4 | 84985 | Hs.379821 |
| 261. | family with sequence similarity 83, member F | FAM83F | NM_138435.1 | 113828 | Hs.197680 |
| 262. | FAT tumor suppressor homolog 2 (*Drosophila*) | FAT2 | NM_001447.1 | 2196 | Hs.132158 |
| 263. | fatty acid amide hydrolase 2 | FAAH2 | NM_174912.2 | 158584 | Hs.496205 |
| 264. | fatty acid binding protein 5 (psoriasis-associated) | FABP5 | NM_001444.1 | 2171 | Hs.558327 |
| 265. | F-box and WD-40 domain protein 7 (archipelago homolog, *Drosophila*) | FBXW7 | NM_001013415.1 | 55294 | Hs.519029 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 266. | F-box protein 42 | FBXO42 | NM_018994.1 | 54455 | Hs.522384 |
| 267. | Fc fragment of IgE, high affinity I, receptor for; alpha polypeptide | FCER1A | NM_002001 | 2205 | Hs.897 |
| 268. | Fc fragment of IgG binding protein | FCGBP | NM_003890.1 | 8857 | Hs.111732 |
| 269. | fer-1-like 3, myoferlin (*C. elegans*) | FER1L3 | NM_013451.2 | 26509 | Hs.500572 |
| 270. | FERM and PDZ domain containing 1 | FRMPD1 | NM_014907.1 | 22844 | Hs.163990 |
| 271. | fetuin B | FETUB | NM_014375.2 | 26998 | Hs.81073 |
| 272. | fibroblast growth factor binding protein 1 | FGFBP1 | NM_005130.3 | 9982 | Hs.1690 |
| 273. | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | FGFR2 | NM_022972.1 | 2263 | Hs.533683 |
| 274. | fibroblast growth factor receptor 3 (achondroplasia, thanatophoric dwarfism) | FGFR3 | NM_000142.2 | 2261 | Hs.1420 |
| 275. | fibronectin type III domain containing 6 | FNDC6 | NM_144717.2 | 152028 | Hs.61232 |
| 276. | fibulin 2 | FBLN2 | NM_001998.2 | 2199 | Hs.198862 |
| 277. | filaggrin | FLG | NM_002016.1 | 2312 | Hs.23783 |
| 278. | filaggrin 2 | RP1-14N1.3 | NM_001014342.1 | 388698 | Hs.156124 |
| 279. | FLJ41603 protein | FLJ41603 | NM_001001669.2 | 389337 | Hs.256206 |
| 280. | forkhead box N1 | FOXN1 | NM_003593.2 | 8456 | Hs.198313 |
| 281. | forkhead box Q1 | FOXQ1 | NM_033260.2 | 94234 | Hs.297452 |
| 282. | frizzled homolog 10 (*Drosophila*) | FZD10 | NM_007197.2 | 11211 | Hs.31664 |
| 283. | furry homolog (*Drosophila*) | FRY | NM_023037 | 10129 | Hs.390874 |
| 284. | FYVE, RhoGEF and PH domain containing 6 | FGD6 | BC013319.1 | 55785 | Hs.506381 |
| 285. | G protein-coupled receptor 1 | GPR1 | NM_005279.2 | 2825 | Hs.184907 |
| 286. | G protein-coupled receptor 115 | GPR115 | NM_153838.2 | 221393 | Hs.150131 |
| 287. | G protein-coupled receptor 172B | GPR172B | NM_017986.2 | 55065 | Hs.110128 |
| 288. | G protein-coupled receptor 87 | GPR87 | NM_023915.2 | 53836 | Hs.58561 |
| 289. | G protein-coupled receptor, family C, group 5, member C | GPRC5C | NM_022036.2 | 55890 | Hs.446438 |
| 290. | galectin-related protein | HSPC159 | NM_014181.1 | 29094 | Hs.372208 |
| 291. | gamma-aminobutyric acid (GABA) A receptor, epsilon | GABRE | NM_021984.2 | 2564 | Hs.22785 |
| 292. | gamma-glutamyltransferase 6 homolog (rat) | GGT6 | NM_153338.1 | 124975 | Hs.130749 |
| 293. | gap junction protein, alpha 1, 43 kDa (connexin 43) | GJA1 | NM_000165.2 | 2697 | Hs.74471 |
| 294. | gap junction protein, beta 2, 26 kDa (connexin 26) | GJB2 | NM_004004.3 | 2706 | Hs.524894 |
| 295. | gap junction protein, beta 3, 31 kDa (connexin 31) | GJB3 | NM_024009.2 | 2707 | Hs.522561 |
| 296. | gap junction protein, beta 5 (connexin 31.1) | GJB5 | NM_005268.2 | 2709 | Hs.198249 |
| 297. | gap junction protein, beta 6 (connexin 30) | GJB6 | NM_006783.2 | 10804 | Hs.511757 |
| 298. | GATA binding protein 3 | GATA3 | NM_001002295.1 | 2625 | Hs.524134 |
| 299. | giant axonal neuropathy (gigaxonin) | GAN | NM_022041.2 | 8139 | Hs.112569 |
| 300. | GIPC PDZ domain containing family, member 2 | GIPC2 | NM_017655.4 | 54810 | Hs.13852 |
| 301. | gliomedin | GLDN | BX538105.1 | 342035 | Hs.526441 |
| 302. | GLIS family zinc finger 1 | GLIS1 | NM_147193.1 | 148979 | Hs.306691 |
| 303. | glutamic pyruvate transaminase (alanine aminotransferase) 2 | GPT2 | NM_133443.1 | 84706 | Hs.460693 |
| 304. | glutathione peroxidase 2 (gastrointestinal) | GPX2 | NM_002083.2 | 2877 | Hs.2704 |
| 305. | glutathione peroxidase 3 (plasma) | GPX3 | NM_002084.3 | 2878 | Hs.386793 |
| 306. | glutathione S-transferase A3 | GSTA3 | NM_000847.3 | 2940 | Hs.102484 |
| 307. | glutathione S-transferase A4 | GSTA4 | NM_001512.2 | 2941 | Hs.485557 |
| 308. | glutathione S-transferase omega 2 | GSTO2 | NM_183239.1 | 119391 | Hs.203634 |
| 309. | glycerophosphodiester phosphodiesterase domain containing 2 | GDPD2 | NM_017711.2 | 54857 | Hs.438712 |
| 310. | glycerophosphodiester phosphodiesterase domain containing 3 | GDPD3 | NM_001031718.1 | 79153 | Hs.289015 |
| 311. | glycolipid transfer protein | GLTP | NM_016433.3 | 51228 | Hs.381256 |
| 312. | glycoprotein Ib (platelet), beta polypeptide | GP1BB | NM_000407.4 | 2812 | Hs.517410 |
| 313. | glycosylphosphatidylinositol specific phospholipase D1 | GPLD1 | NM_001503.2 | 2822 | Hs.512001 |
| 314. | GM2 ganglioside activator | GM2A | NM_000405.3 | 2760 | Hs.483873 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 315. | GPI-gamma 4 | GPIG4 | NM_152545 | 153020 | Hs.352552 |
| 316. | grainyhead-like 1 (*Drosophila*) | GRHL1 | NM_198182.1 | 29841 | Hs.418493 |
| 317. | grainyhead-like 2 (*Drosophila*) | GRHL2 | NM_024915.1 | 79977 | Hs.161160 |
| 318. | grainyhead-like 3 (*Drosophila*) | GRHL3 | NM_021180.2 | 57822 | Hs.369825 |
| 319. | GRAM domain containing 1C | GRAMD1C | NM_017577.2 | 54762 | Hs.24583 |
| 320. | GRINL1A combined protein | Gcom1 | NM_001018090.1 | 145781 | Hs.50841 |
| 321. | growth arrest-specific 6 | GAS6 | NM_000820.1 | 2621 | Hs.369201 |
| 322. | growth hormone regulated TBC protein 1 | GRTP1 | NM_024719.1 | 79774 | Hs.170904 |
| 323. | guanine deaminase | GDA | NM_004293 | 9615 | Hs.494163 |
| 324. | guanylate binding protein family, member 6 | GBP6 | AL703282 | 163351 | Hs.254338 |
| 325. | H3 histone, family 3B (H3.3B) | H3F3B | NM_005324.3 | 3021 | Hs.180877 |
| 326. | hairless homolog (mouse) | HR | NM_005144.3 | 55806 | Hs.272367 |
| 327. | heparan sulfate (glucosamine) 3-O-sulfotransferase 6 | HS3ST6 | NM_001009606.1 | 64711 | Hs.200735 |
| 328. | hepatic leukemia factor | HLF | NM_002126.4 | 3131 | Hs.196952 |
| 329. | hepatocellular carcinoma antigen gene 520 | LOC63928 | NM_022097.1 | 63928 | Hs.178589 |
| 330. | hephaestin | HEPH | NM_014799 | 9843 | Hs.31720 |
| 331. | histidine ammonia-lyase | HAL | NM_002108.2 | 3034 | Hs.190783 |
| 332. | homeo box A9 | HOXA9 | NM_152739.3 | 3205 | Hs.127428 |
| 333. | homeodomain-only protein | HOP | NM_032495 | 84525 | Hs.13775 |
| 334. | homer homolog 2 (*Drosophila*) | HOMER2 | NM_004839.2 | 9455 | Hs.93564 |
| 335. | hook homolog 1 (*Drosophila*) | HOOK1 | NM_015888.4 | 51361 | Hs.378836 |
| 336. | HtrA serine peptidase 1 | HTRA1 | NM_002775.3 | 5654 | Hs.501280 |
| 337. | huntingtin interacting protein 1 related | HIP1R | NM_003959.1 | 9026 | Hs.524815 |
| 338. | hyaluronan synthase 3 | HAS3 | NM_138612.1 | 3038 | Hs.85962 |
| 339. | hyaluronoglucosaminidase 1 | HYAL1 | NM_153282.1 | 3373 | Hs.75619 |
| 340. | hyaluronoglucosaminidase 4 | HYAL4 | NM_012269.1 | 23553 | Hs.28673 |
| 341. | hydatidiform mole associated and imprinted | HYMAI | NR_002768.1 | 57061 | Hs.698009 |
| 342. | hydroxysteroid (11-beta) dehydrogenase 2 | HSD11B2 | NM_000196.2 | 3291 | Hs.1376 |
| 343. | hypothetical gene supported by BC030123 | LOC441461 | XM_499157.2 | 441461 | Hs.163155 |
| 344. | hypothetical LOC653602 | LOC653602 | XM_939526.1 | 653602 | Hs.433956 |
| 345. | hypothetical protein DJ667H12.2 | DJ667H12.2 | NM_019605 | 56256 | Hs.445835 |
| 346. | hypothetical protein DKFZP761M1511 | DKFZP761M1511 | AK096661.1 | 54492 | Hs.91521 |
| 347. | hypothetical protein FLJ10156 | FLJ10156 | NM_019103 | 54478 | Hs.404323 |
| 348. | hypothetical protein FLJ10634 | FLJ10634 | XM_938980.1 | 643338 | Hs.334475 |
| 349. | hypothetical protein FLJ10706 | FLJ10706 | NM_018186 | 55732 | Hs.443551 |
| 350. | hypothetical protein FLJ11183 | FLJ11183 | AK026881 | 55785 | Hs.170623 |
| 351. | hypothetical protein FLJ11235 | FLJ11235 | NM_019033 | 54508 | Hs.555952 |
| 352. | hypothetical protein FLJ20003 | FLJ20003 | NM_017615 | 54780 | Hs.258798 |
| 353. | hypothetical protein FLJ21511 | FLJ21511 | NM_025087.1 | 80157 | Hs.479703 |
| 354. | hypothetical protein FLJ22757 | FLJ22757 | NM_024898 | 79958 | Hs.236449 |
| 355. | hypothetical protein FLJ23306 | FLJ23306 | NM_024530 | 79579 | Hs.5890 |
| 356. | hypothetical protein FLJ25217 | FLJ25217 | XM_939893.1 | 650803 | Hs.153450 |
| 357. | hypothetical protein FLJ30532 | FLJ30532 | NM_144724 | 153562 | Hs.390601 |
| 358. | hypothetical protein FLJ32798 | FLJ32798 | NM_173496 | 143098 | Hs.350684 |
| 359. | hypothetical protein FLJ33868 | FLJ33868 | NM_152574 | 158219 | Hs.49605 |
| 360. | hypothetical protein FLJ35880 | FLJ35880 | NM_153264.2 | 256076 | Hs.205403 |
| 361. | hypothetical protein FLJ37464 | FLJ37464 | NM_173815.3 | 283848 | Hs.346947 |
| 362. | hypothetical protein FLJ39005 | FLJ39005 | NM_178521 | 284313 | Hs.130286 |
| 363. | hypothetical protein FLJ90492 | FLJ90492 | NM_181783 | 160418 | Hs.331268 |
| 364. | hypothetical protein from clone 643 | LOC57228 | NM_020467 | 57228 | Hs.206501 |
| 365. | hypothetical protein LOC126917 | LOC126917 | XM_928886.1 | 126917 | Hs.466625 |
| 366. | hypothetical protein LOC130576 | LOC130576 | NM_177964.3 | 130576 | Hs.357567 |
| 367. | hypothetical protein LOC131873 | LOC131873 | XM_940071.1 | 131873 | Hs.477571 |
| 368. | hypothetical protein LOC144501 | LOC144501 | NM_182507 | 144501 | Hs.140978 |
| 369. | hypothetical protein LOC147645 | LOC147645 | XM_085831.10 | 147645 | Hs.293236 |
| 370. | hypothetical protein LOC151878 | LOC151878 | BC014063.1 | 151878 | Hs.680377 |
| 371. | hypothetical protein LOC196264 | LOC196264 | BG037101 | 196264 | Hs.15396 |
| 372. | hypothetical protein LOC283070 | LOC283070 | AK097377.1 | 283070 | Hs.376041 |
| 373. | hypothetical protein LOC283404 | LOC283404 | BC039104.1 | 283404 | Hs.556299 |
| 374. | hypothetical protein LOC283666 | LOC283666 | BC035094.2 | 283666 | Hs.560343 |
| 375. | hypothetical protein LOC283874 | LOC283874 | AK097909.1 | 283874 | Hs.459699 |
| 376. | hypothetical protein LOC284023 | LOC284023 | XM_933967.1 | 284023 | Hs.354493 |
| 377. | hypothetical protein LOC285535 | LOC285535 | AK021540.1 | 285535 | Hs.400256 |
| 378. | hypothetical protein LOC286440 | LOC286440 | AK123807.1 | 286440 | Hs.348844 |
| 379. | hypothetical protein LOC338667 | LOC338667 | BC043578.1 | 338667 | Hs.558217 |
| 380. | hypothetical protein LOC348938 | LOC348938 | XM_371777.4 | 348938 | Hs.4285 |
| 381. | hypothetical protein LOC646014 | LOC646014 | XM_928978.1 | 646014 | Hs.117853 |

TABLE A-continued

Genes differentially expressed in metastatic melanoma. Expression
of the genes listed in this table is decreased relative to non-metastatic samples.

| | Gene description | Gene Symbol | GenBank ID | Entrez Gene ID | UniGene ID |
|---|---|---|---|---|---|
| 382. | hypothetical protein MGC14128 | MGC14128 | NM_032899 | 84985 | Hs.290881 |
| 383. | hypothetical protein MGC14376 | MGC14376 | NM_001001870.1 | 84981 | Hs.417157 |
| 384. | hypothetical protein MGC2655 | MGC2655 | XM_085463.6 | 146439 | Hs.513285 |
| 385. | hypothetical protein MGC4248 | MGC4248 | NM_032333 | 84293 | Hs.301519 |
| 386. | ICEBERG caspase-1 inhibitor | ICEBERG | NM_021571 | 59082 | Hs.56279 |
| 387. | IGF-like family member 1 | IGFL1 | NM_198541.1 | 374918 | Hs.546554 |
| 388. | IGF-like family member 2 | IGFL2 | NM_001002915.1 | 147920 | Hs.99376 |
| 389. | InaD-like (*Drosophila*) | INADL | NM_170605.2 | 10207 | Hs.478125 |
| 390. | inhibitor of DNA binding 1, dominant negative helix-loop-helix protein | ID1 | NM_002165.2 | 3397 | Hs.504609 |
| 391. | inositol 1,3,4,5,6-pentakisphosphate 2-kinase | IPPK | NM_022755.4 | 64768 | Hs.459896 |
| 392. | inositol(myo)-1(or 4)-monophosphatase 2 | IMPA2 | NM_014214.1 | 3613 | Hs.367992 |
| 393. | insulin-degrading enzyme | IDE | NM_004969 | 3416 | Hs.500546 |
| 394. | integrin, beta 4 | ITGB4 | NM_000213.3 | 3691 | Hs.370255 |
| 395. | integrin, beta 6 | ITGB6 | NM_000888.3 | 3694 | Hs.470399 |
| 396. | interferon regulatory factor 6 | IRF6 | NM_006147.2 | 3664 | Hs.355827 |
| 397. | interleukin 1 family, member 10 (theta) | IL1F10 | NM_173161.1 | 84639 | Hs.306974 |
| 398. | interleukin 1 family, member 5 (delta) | IL1F5 | NM_012275.2 | 26525 | Hs.516301 |
| 399. | interleukin 1 family, member 7 (zeta) | IL1F7 | NM_014439.3 | 27178 | Hs.166371 |
| 400. | interleukin 1 family, member 8 (eta) | IL1F8 | NM_014438.3 | 27177 | Hs.278909 |
| 401. | interleukin 1 family, member 9 | IL1F9 | NM_019618.2 | 56300 | Hs.211238 |
| 402. | interleukin 1 receptor antagonist | IL1RN | NM_173843.1 | 3557 | Hs.81134 |
| 403. | interleukin 1 receptor, type I | IL1R1 | NM_000877.2 | 3554 | Hs.557403 |
| 404. | interleukin 18 (interferon-gamma-inducing factor) | IL18 | NM_001562.2 | 3606 | Hs.83077 |
| 405. | interleukin 20 receptor, alpha | IL20RA | NM_014432.2 | 53832 | Hs.445868 |
| 406. | interleukin 22 receptor, alpha 1 | IL22RA1 | NM_021258.2 | 58985 | Hs.110915 |
| 407. | involucrin | IVL | NM_005547 | 3713 | Hs.157091 |
| 408. | iroquois homeobox protein 1 | IRX1 | NM_024337.3 | 79192 | Hs.424156 |
| 409. | iroquois homeobox protein 3 | IRX3 | NM_024336.1 | 79191 | Hs.499205 |
| 410. | iroquois homeobox protein 4 | IRX4 | NM_016358.1 | 50805 | Hs.196927 |
| 411. | iroquois homeobox protein 5 | IRX5 | NM_005853.4 | 10265 | Hs.435730 |
| 412. | jagged 1 (Alagille syndrome) | JAG1 | NM_000214.1 | 182 | Hs.224012 |
| 413. | junction plakoglobin | JUP | NM_002230.1 | 3728 | Hs.514174 |
| 414. | kallikrein 10 | KLK10 | NM_002776.3 | 5655 | Hs.275464 |
| 415. | kallikrein 11 | KLK11 | NM_006853.2 | 11012 | Hs.57771 |
| 416. | kallikrein 12 | KLK12 | NM_019598.2 | 43849 | Hs.411572 |
| 417. | kallikrein 13 | KLK13 | NM_015596.1 | 26085 | Hs.165296 |
| 418. | kallikrein 5 | KLK5 | NM_012427.3 | 25818 | Hs.50915 |
| 419. | kallikrein 6 (neurosin, zyme) | KLK6 | NM_001012964.1 | 5653 | Hs.79361 |
| 420. | kallikrein 7 (chymotryptic, stratum corneum) | KLK7 | NM_005046.2 | 5650 | Hs.151254 |
| 421. | kallikrein 8 (neuropsin/ovasin) | KLK8 | NM_007196.2 | 11202 | Hs.104570 |
| 422. | kallikrein 9 | KLK9 | NM_012315.1 | 284366 | Hs.448942 |
| 423. | keratin 1 (epidermolytic hyperkeratosis) | KRT1 | NM_006121 | 3848 | Hs.80828 |
| 424. | keratin 10 (epidermolytic hyperkeratosis; keratosis palmaris et plantaris) | KRT10 | NM_000421.2 | 3858 | Hs.99936 |
| 425. | keratin 14 (epidermolysis bullosa simplex, Dowling-Meara, Koebner) | KRT14 | NM_000526.3 | 3861 | Hs.355214 |
| 426. | keratin 15 | KRT15 | NM_002275.2 | 3866 | Hs.80342 |
| 427. | keratin 16 (focal non-epidermolytic palmoplantar keratoderma) | KRT16 | NM_005557.2 | 3868 | Hs.432448 |
| 428. | keratin 17 | KRT17 | NM_000422.1 | 3872 | Hs.2785 |
| 429. | keratin 1B | KRT1B | BC033366.1 | 374454 | Hs.334989 |
| 430. | keratin 23 (histone deacetylase inducible) | KRT23 | NM_015515.3 | 25984 | Hs.9029 |
| 431. | keratin 2A (epidermal ichthyosis bullosa of Siemens) | KRT2A | NM_000423.2 | 3849 | Hs.707 |
| 432. | keratin 5 (epidermolysis bullosa simplex, Dowling-Meara/Kobner/Weber-Cockayne types) | KRT5 | NM_000424.2 | 3852 | Hs.433845 |
| 433. | keratin 5b | K5B | NM_173352 | 196374 | Hs.121824 |
| 434. | keratin 6A | KRT6A | NM_005554 | 3853 | Hs.367762 |
| 435. | keratin 6B | KRT6B | NM_005555.2 | 3854 | Hs.524438 |
| 436. | keratin 7 | KRT7 | NM_005556 | 3855 | Hs.411501 |
| 437. | keratin 74 | KRT74 | NM_175053.2 | 121391 | Hs.56255 |
| 438. | keratin, hair, acidic, 1 | KRTHA1 | NM_002277.2 | 3881 | Hs.41696 |
| 439. | keratin, hair, acidic, 2 | KRTHA2 | NM_002278.2 | 3882 | Hs.41752 |

TABLE A-continued

Genes differentially expressed in metastatic melanoma. Expression
of the genes listed in this table is decreased relative to non-metastatic samples.

| | Gene description | Gene Symbol | GenBank ID | Entrez Gene ID | UniGene ID |
|---|---|---|---|---|---|
| 440. | keratinocyte differentiation-associated protein | KRTDAP | NM_207392.1 | 388533 | Hs.112457 |
| 441. | KIAA0513 | KIAA0513 | NM_014732 | 9764 | Hs.301658 |
| 442. | KIAA0514 | KIAA0514 | NM_014696.2 | 9721 | Hs.523375 |
| 443. | KIAA0874 protein | KIAA0874 | NM_015208 | 23253 | Hs.388877 |
| 444. | KIAA1117 | KIAA1117 | AK094766.1 | 23033 | Hs.520246 |
| 445. | KIAA1145 protein | KIAA1145 | NM_020698 | 57458 | Hs.173392 |
| 446. | KIAA1217 | KIAA1217 | BX648451.1 | 56243 | Hs.445885 |
| 447. | KIAA1411 | KIAA1411 | NM_020819 | 57579 | Hs.211700 |
| 448. | KIAA1543 | KIAA1543 | BC020431 | 57662 | Hs.17686 |
| 449. | KIAA1671 protein | KIAA1671 | AL832019.1 | 85379 | Hs.419171 |
| 450. | KIAA1912 protein | KIAA1912 | XM_055636.4 | 114800 | Hs.117136 |
| 451. | KIAA2022 | KIAA2022 | NM_001008537.1 | 340533 | Hs.124128 |
| 452. | kinesin family member 1C | KIF1C | NM_006612.3 | 10749 | Hs.435120 |
| 453. | kinesin light chain 3 | KLC3 | BC025318.1 | 147700 | Hs.298079 |
| 454. | KIT ligand | KITLG | NM_000899.3 | 4254 | Hs.1048 |
| 455. | kringle containing transmembrane protein 1 | KREMEN1 | NM_001039571.1 | 83999 | Hs.229335 |
| 456. | Kruppel-like factor 4 (gut) | KLF4 | NM_004235.3 | 9314 | Hs.376206 |
| 457. | Kruppel-like factor 5 (intestinal) | KLF5 | NM_001730.3 | 688 | Hs.508234 |
| 458. | Kruppel-like factor 8 | KLF8 | NM_007250 | 11279 | Hs.411296 |
| 459. | ladinin 1 | LAD1 | NM_005558.3 | 3898 | Hs.519035 |
| 460. | LAG1 longevity assurance homolog 3 (*S. cerevisiae*) | LASS3 | NM_178842.2 | 204219 | Hs.416099 |
| 461. | LAG1 longevity assurance homolog 4 (*S. cerevisiae*) | LASS4 | NM_024552.1 | 79603 | Hs.515111 |
| 462. | laminin, alpha 2 (merosin, congenital muscular dystrophy) | LAMA2 | NM_000426.2 | 3908 | Hs.200841 |
| 463. | laminin, alpha 3 | LAMA3 | NM_198129.1 | 3909 | Hs.436367 |
| 464. | laminin, beta 3 | LAMB3 | NM_000228 | 3914 | Hs.497636 |
| 465. | laminin, beta 4 | LAMB4 | NM_007356.1 | 22798 | Hs.62022 |
| 466. | laminin, gamma 2 | LAMC2 | NM_005562.1 | 3918 | Hs.530509 |
| 467. | late cornified envelope 1B | LCE1B | NM_178349.1 | 353132 | Hs.375103 |
| 468. | late cornified envelope 2B | LCE2B | NM_014357.3 | 26239 | Hs.234766 |
| 469. | late cornified envelope 3D | LCE3D | NM_032563.1 | 84648 | Hs.244349 |
| 470. | latrophilin 3 | LPHN3 | NM_015236.3 | 23284 | Hs.28391 |
| 471. | lectin, galactoside-binding, soluble, 7 (galectin 7) | LGALS7 | NM_002307.1 | 3963 | Hs.558355 |
| 472. | leucine rich repeat containing 8 family, member E | LRRC8E | NM_025061.3 | 80131 | Hs.501511 |
| 473. | leucine rich repeat neuronal 1 | LRRN1 | NM_020873.3 | 57633 | Hs.163244 |
| 474. | leucine-rich repeat-containing G protein-coupled receptor 4 | LGR4 | NM_018490.1 | 55366 | Hs.502176 |
| 475. | leucine-rich repeat-containing G protein-coupled receptor 6 | LGR6 | NM_021636.2 | 59352 | Hs.497402 |
| 476. | leucine-rich repeats and immunoglobulin-like domains 3 | LRIG3 | NM_153377.3 | 121227 | Hs.253736 |
| 477. | leukotriene B4 receptor | LTB4R | NM_181657.1 | 1241 | Hs.525256 |
| 478. | leukotriene C4 synthase | LTC4S | NM_145867.1 | 4056 | Hs.456 |
| 479. | ligand of numb-protein X 1 | LNX1 | NM_032622.1 | 84708 | Hs.407755 |
| 480. | likely ortholog of mouse Sh3 domain YSC-like 1 | SH3YL1 | NM_015677 | 26751 | Hs.147365 |
| 481. | LIM domain kinase 2 | LIMK2 | NM_005569.3 | 3985 | Hs.474596 |
| 482. | lines homolog 1 (*Drosophila*) | LINS1 | BC010363.1 | 55180 | Hs.105633 |
| 483. | lipocalin 2 (oncogene 24p3) | LCN2 | NM_005564 | 3934 | Hs.204238 |
| 484. | LOC153470 | LOC153470 | BC021680.1 | 389336 | Hs.173059 |
| 485. | LOC284752 | LOC284752 | AI056877 | 284752 | Hs.38207 |
| 486. | LOC340813 | LOC340813 | AL117475 | 340813 | Hs.306344 |
| 487. | LOC345926 | LOC345926 | XM_933651.1 | 644241 | Hs.62929 |
| 488. | LOC346876 | LOC346876 | AI224578 | 346876 | Hs.147678 |
| 489. | LOC349496 | LOC349496 | BF064181 | 349496 | Hs.147964 |
| 490. | LOC349889 | LOC349889 | AW589793 | 349889 | Hs.224713 |
| 491. | loricrin | LOR | NM_000427 | 4014 | Hs.251680 |
| 492. | lunatic fringe homolog (*Drosophila*) | LFNG | NM_001040168.1 | 3955 | Hs.159142 |
| 493. | Ly-6 neurotoxin-like protein 1 | LYNX1 | NM_023946 | 66004 | Hs.158665 |
| 494. | LY6/PLAUR domain containing 3 | LYPD3 | NM_014400.2 | 27076 | Hs.377028 |
| 495. | LY6/PLAUR domain containing 5 | LYPD5 | NM_182573.1 | 284348 | Hs.44289 |
| 496. | lymphocyte antigen 6 complex, locus D | LY6D (E48) | NM_003695.2 | 8581 | Hs.415762 |
| 497. | lymphocyte antigen 6 complex, locus G6C | LY6G6C | NM_025261.1 | 80740 | Hs.241586 |
| 498. | lymphocyte antigen 75 | LY75 | NM_002349.1 | 4065 | Hs.153563 |
| 499. | lysosomal-associated membrane protein 3 | LAMP3 | NM_014398.2 | 27074 | Hs.518448 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 500. | macrophage stimulating 1 receptor (c-met-related tyrosine kinase) | MST1R | NM_002447.1 | 4486 | Hs.517973 |
| 501. | major histocompatibility complex, class II, DQ beta 2 | HLA-DQB2 | NM_182549.1 | 3120 | Hs.554753 |
| 502. | mal, T-cell differentiation protein 2 | MAL2 | NM_052886 | 114569 | Hs.201083 |
| 503. | mal, T-cell differentiation protein-like | MALL | NM_005434.3 | 7851 | Hs.185055 |
| 504. | malic enzyme 1, NADP(+)-dependent, cytosolic | ME1 | NM_002395 | 4199 | Hs.14732 |
| 505. | MAM domain containing 2 | MAMDC2 | NM_153267.3 | 256691 | Hs.127386 |
| 506. | mannan-binding lectin serine peptidase 1 (C4/C2 activating component of Ra-reactive factor) | MASP1 | NM_001879.4 | 5648 | Hs.89983 |
| 507. | MAS-related GPR, member F | MRGPRF | NM_145015.2 | 219928 | Hs.118513 |
| 508. | matrix metallopeptidase 28 | MMP28 | NM_024302.3 | 79148 | Hs.380710 |
| 509. | melanoma-derived leucine zipper, extra-nuclear factor | MLZE | NM_031415.2 | 56169 | Hs.133244 |
| 510. | membrane associated guanylate kinase, WW and PDZ domain containing 1 | MAGI1 | NM_004742.2 | 9223 | Hs.651939 |
| 511. | membrane protein, palmitoylated 7 (MAGUK p55 subfamily member 7) | MPP7 | NM_173496.2 | 143098 | Hs.499159 |
| 512. | membrane-associated ring finger (C3HC4) 3 | MAR3 | NM_178450.2 | 115123 | Hs.132441 |
| 513. | membrane-spanning 4-domains, subfamily A, member 2 (Fc fragment of IgE, high affinity 1, receptor for; beta polypeptide) | MS4A2 | NM_000139.2 | 2206 | Hs.386748 |
| 514. | meningioma (disrupted in balanced translocation) 1 | MN1 | NM_002430.2 | 4330 | Hs.268515 |
| 515. | metallo phosphoesterase | MPPE1 | NM_023075 | 65258 | Hs.154145 |
| 516. | metastasis associated lung adenocarcinoma transcript 1 (non-coding RNA) | MALAT1 | AK130345.1 | 378938 | Hs.187199 |
| 517. | methyltransferase like 7A | METTL7A | NM_014033.3 | 25840 | Hs.288771 |
| 518. | MICAL C-terminal like | MICALCL | NM_032867.1 | 84953 | Hs.128196 |
| 519. | microfibrillar-associated protein 3-like | MFAP3L | AB014526.1 | 9848 | Hs.178121 |
| 520. | microseminoprotein, beta- | MSMB | NM_002443.2 | 4477 | Hs.255462 |
| 521. | microsomal glutathione S-transferase 1 | MGST1 | NM_020300.3 | 4257 | Hs.389700 |
| 522. | microtubule associated serine/threonine kinase family member 4 | MAST4 | NM_198828.1 | 375449 | Hs.482329 |
| 523. | microtubule-associated protein 7 | MAP7 | NM_003980.3 | 9053 | Hs.486548 |
| 524. | mitogen-activated protein kinase kinase kinase 9 | MAP3K9 | NM_033141.2 | 4293 | Hs.437214 |
| 525. | monoamine oxidase A | MAOA | NM_000240.2 | 4128 | Hs.183109 |
| 526. | MRS2-like, magnesium homeostasis factor (S. cerevisiae) | MRS2L | NM_020662.2 | 57380 | Hs.533291 |
| 527. | mucin 15 | MUC15 | NM_145650.2 | 143662 | Hs.407152 |
| 528. | muscleblind-like (Drosophila) | MBNL1 | NM_021038.3 | 4154 | Hs.478000 |
| 529. | myosin VB | MYO5B | XM_371116.4 | 4645 | Hs.550481 |
| 530. | myosin VI | MYO6 | NM_004999.3 | 4646 | Hs.149387 |
| 531. | NACHT, leucine rich repeat and PYD (pyrin domain) containing 1 | NALP1 | AK057464.1 | 22861 | Hs.104305 |
| 532. | NAD(P) dependent steroid dehydrogenase-like | HSPC105 | NM_145168 | 93517 | Hs.87779 |
| 533. | NADH dehydrogenase (ubiquinone) 1 alpha subcomplex, 4-like 2 | NDUFA4L2 | NM_020142.3 | 56901 | Hs.221447 |
| 534. | Nance-Horan syndrome (congenital cataracts and dental anomalies) | NHS | NM_198270.2 | 4810 | Hs.201623 |
| 535. | Nanog homeobox | NANOG | NM_024865.1 | 79923 | Hs.329296 |
| 536. | NDRG family member 4 | NDRG4 | NM_020465.2 | 65009 | Hs.322430 |
| 537. | nebulette | NEBL | NM_006393 | 10529 | Hs.5025 |
| 538. | nephronectin | NPNT | NM_001033047.1 | 255743 | Hs.518921 |
| 539. | netrin 4 | NTN4 | NM_021229.3 | 59277 | Hs.201034 |
| 540. | neuroepithelial cell transforming gene 1 | NET1 | NM_005863.2 | 10276 | Hs.25155 |
| 541. | neuromedin U | NMU | NM_006681.1 | 10874 | Hs.418367 |
| 542. | neuronal guanine nucleotide exchange factor | NGEF | NM_019850.1 | 25791 | Hs.97316 |
| 543. | neurotrophin 5 (neurotrophin 4/5) | NTF5 | NM_006179 | 4909 | Hs.266902 |
| 544. | NGNL6975 | UNQ6975 | AK095550.1 | 400952 | Hs.468368 |
| 545. | nicotinamide nucleotide adenylyltransferase 3 | NMNAT3 | NM_178177.2 | 349565 | Hs.208673 |
| 546. | NIPA-like domain containing 1 | NPAL1 | CR749484.1 | 152519 | Hs.134190 |
| 547. | NIPA-like domain containing 2 | NPAL2 | NM_024759.1 | 79815 | Hs.309489 |
| 548. | NSE1 | NSE1 | NM_145175 | 151354 | Hs.260855 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 549. | NUAK family, SNF1-like kinase, 1 | NUAK1 | NM_014840.2 | 9891 | Hs.524692 |
| 550. | nuclear factor I/B | NFIB | NM_005596.2 | 4781 | Hs.370359 |
| 551. | nuclear factor of activated T-cells, cytoplasmic, calcineurin-dependent 3 | NFATC3 | NM_004555.2 | 4775 | Hs.341716 |
| 552. | nucleosome assembly protein 1-like 2 | NAP1L2 | NM_021963.2 | 4674 | Hs.66180 |
| 553. | O-acyltransferase (membrane bound) domain containing 2 | OACT2 | NM_138799.2 | 129642 | Hs.467634 |
| 554. | odz, odd Oz/ten-m homolog 2 (*Drosophila*) | ODZ2 | AB032953 | 57451 | Hs.155915 |
| 555. | odz, odd Oz/ten-m homolog 4 (*Drosophila*) | ODZ4 | BF112171 | 26011 | Hs.213087 |
| 556. | olfactomedin-like 2A | OLFML2A | NM_182487.1 | 169611 | Hs.357004 |
| 557. | orphan short-chain dehydrogenase/reductase | SDR-O | NM_148897.1 | 121214 | Hs.380178 |
| 558. | OTU domain, ubiquitin aldehyde binding 2 | OTUB2 | BC009615.1 | 78990 | Hs.278815 |
| 559. | ovo-like 1 (*Drosophila*) | OVOL1 | NM_004561.2 | 5017 | Hs.134434 |
| 560. | oxoglutarate (alpha-ketoglutarate) receptor 1 | OXGR1 | NM_080818.3 | 27199 | Hs.352218 |
| 561. | p21(CDKN1A)-activated kinase 6 | PAK6 | NM_020168.3 | 56924 | Hs.513645 |
| 562. | p53-regulated apoptosis-inducing protein 1 | P53AIP1 | NM_022112.1 | 63970 | Hs.160953 |
| 563. | paired-like homeodomain transcription factor 1 | PITX1 | NM_002653 | 5307 | Hs.84136 |
| 564. | palladin, cytoskeletal associated protein | PALLD | NM_016081 | 23022 | Hs.194431 |
| 565. | palmdelphin | PALMD | NM_017734.2 | 54873 | Hs.483993 |
| 566. | par-6 partitioning defective 6 homolog gamma (*C. elegans*) | PARD6G | NM_032510 | 84552 | Hs.223584 |
| 567. | patatin-like phospholipase domain containing 1 | PNPLA1 | NM_173676.1 | 285848 | Hs.407002 |
| 568. | PDZ domain containing 3 | PDZK3 | NM_178140.2 | 23037 | Hs.481819 |
| 569. | PDZK1 interacting protein 1 | PDZK1IP1 | NM_005764.3 | 10158 | Hs.431099 |
| 570. | peptidase inhibitor 3, skin-derived (SKALP) | PI3 | NM_002638.2 | 5266 | Hs.112341 |
| 571. | peptidyl arginine deiminase, type 1 | PADI1 | NM_013358.1 | 29943 | Hs.412941 |
| 572. | peptidylprolyl isomerase C (cyclophilin C) | PPIC | NM_000943.4 | 5480 | Hs.110364 |
| 573. | peptidylprolyl isomerase D (cyclophilin D) | PPID | NM_005038.2 | 5481 | Hs.183958 |
| 574. | periplakin | PPL | NM_002705.3 | 5493 | Hs.192233 |
| 575. | peroxisomal biogenesis factor 3 | PEX3 | AK023593.1 | 153914 | Hs.7277 |
| 576. | PERP, TP53 apoptosis effector | PERP | NM_022121.2 | 64065 | Hs.520421 |
| 577. | PET112-like (yeast) | PET112L | NM_004564.1 | 5188 | Hs.119316 |
| 578. | Phosphatidylinositol glycan anchor biosynthesis, class L | PIGL | NM_004278 | 9487 | Hs.433422 |
| 579. | phosphoinositide-3-kinase, class 2, gamma polypeptide | PIK3C2G | NM_004570.2 | 5288 | Hs.22500 |
| 580. | phospholipase A2 receptor 1, 180 kDa | PLA2R1 | NM_001007267.1 | 22925 | Hs.410477 |
| 581. | phospholipase A2, group III | PLA2G3 | NM_015715.2 | 50487 | Hs.149623 |
| 582. | phospholipase A2, group IVB (cytosolic) | PLA2G4B | NM_005090.2 | 8681 | Hs.567254 |
| 583. | phosphorylase kinase, alpha 1 (muscle) | PHKA1 | NM_002637.1 | 5255 | Hs.201379 |
| 584. | phosphotyrosine interaction domain containing 1 | PID1 | NM_017933.3 | 55022 | Hs.409352 |
| 585. | phytanoyl-CoA dioxygenase domain containing 1 | PHYHD1 | NM_174933.2 | 254295 | Hs.326391 |
| 586. | placenta-specific 2 | PLAC2 | NM_153375.1 | 257000 | Hs.515575 |
| 587. | plakophilin 1 (ectodermal dysplasia/skin fragility syndrome) | PKP1 | NM_001005337.1 | 5317 | Hs.497350 |
| 588. | plakophilin 2 | PKP2 | NM_001005242.1 | 5318 | Hs.164384 |
| 589. | plakophilin 3 | PKP3 | NM_007183.2 | 11187 | Hs.534395 |
| 590. | plasma membrane proteolipid (plasmolipin) | PLLP | NM_015993.1 | 51090 | Hs.200821 |
| 591. | pleckstrin homology domain containing, family A (phosphoinositide binding specific) member 1 | PLEKHA1 | NM_001001974.1 | 59338 | Hs.287830 |
| 592. | pleiomorphic adenoma gene-like 1 | PLAGL1 | NM_002656.2 | 5325 | Hs.444975 |
| 593. | poliovirus receptor-related 4 | PVRL4 | NM_030916.1 | 81607 | Hs.492490 |
| 594. | potassium channel, subfamily K, member 1 | KCNK1 | NM_002245 | 3775 | Hs.376874 |
| 595. | potassium channel, subfamily K, member 6 | KCNK6 | NM_004823.1 | 9424 | Hs.240395 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 596. | potassium channel, subfamily K, member 7 | KCNK7 | NM_033455.1 | 10089 | Hs.175218 |
| 597. | potassium inwardly-rectifying channel, subfamily J, member 12 | KCNJ12 | NM_021012.3 | 3768 | Hs.2363 |
| 598. | potassium voltage-gated channel, Shal-related subfamily, member 3 | KCND3 | NM_004980.3 | 3752 | Hs.535274 |
| 599. | POU domain, class 2, transcription factor 3 | POU2F3 | NM_014352.1 | 25833 | Hs.227115 |
| 600. | POU domain, class 3, transcription factor 3 | POU3F3 | NM_006236.1 | 5455 | Hs.248158 |
| 601. | PP12104 mRNA | PP12104 | XM_928053.1 | 643008 | |
| 602. | pre-B-cell leukemia transcription factor 1 | PBX1 | NM_002585.1 | 5087 | Hs.493096 |
| 603. | premature ovarian failure, 1B | POF1B | NM_024921 | 79983 | Hs.267038 |
| 604. | PRKC, apoptosis, WT1, regulator | PAWR | NM_002583 | 5074 | Hs.406074 |
| 605. | progastricsin (pepsinogen C) | PGC | NM_002630.1 | 5225 | Hs.1867 |
| 606. | progesterone receptor membrane component 2 | PGRMC2 | NM_006320.1 | 10424 | Hs.507910 |
| 607. | programmed cell death 4 (neoplastic transformation inhibitor) | PDCD4 | NM_014456 | 27250 | Hs.232543 |
| 608. | prolactin-induced protein | PIP | NM_002652.2 | 5304 | Hs.99949 |
| 609. | proline rich Gla (G-carboxyglutamic acid) 4 (transmembrane) | PRRG4 | NM_024081.4 | 79056 | Hs.471695 |
| 610. | prominin 2 | PROM2 | NM_144707.1 | 150696 | Hs.469313 |
| 611. | proprotein convertase subtilisin/kexin type 5 | PCSK5 | NM_006200.2 | 5125 | Hs.368542 |
| 612. | prostaglandin E receptor 3 (subtype EP3) | PTGER3 | NM_198712.2 | 5733 | Hs.445000 |
| 613. | prostaglandin-endoperoxide synthase 1 (prostaglandin G/H synthase and cyclooxygenase) | PTGS1 | NM_080591.1 | 5742 | Hs.201978 |
| 614. | protease, serine 27 | PRSS27 | NM_031948.3 | 83886 | Hs.332878 |
| 615. | protease, serine, 12 (neurotrypsin, motopsin) | PRSS12 | NM_003619.2 | 8492 | Hs.445857 |
| 616. | protease, serine, 2 (trypsin 2) | PRSS2 | NM_002770.2 | 5645 | Hs.367767 |
| 617. | protease, serine, 3 (mesotrypsin) | PRSS3 | NM_002771.2 | 5646 | Hs.435699 |
| 618. | protease, serine, 8 (prostasin) | PRSS8 | NM_002773.2 | 5652 | Hs.75799 |
| 619. | protein kinase (cAMP-dependent, catalytic) inhibitor alpha | PKIA | NM_181839.1 | 5569 | Hs.433700 |
| 620. | protein phosphatase 1, regulatory (inhibitor) subunit 13 like | PPP1R13L | NM_006663.2 | 10848 | Hs.560721 |
| 621. | protein phosphatase 1, regulatory (inhibitor) subunit 14C | PPP1R14C (1R14C) | NM_030949.1 | 81706 | Hs.486798 |
| 622. | protein phosphatase 2 (formerly 2A), regulatory subunit B (PR 52), gamma isoform | PPP2R2C | NM_020416 | 5522 | Hs.479069 |
| 623. | protein phosphatase 2 (formerly 2A), regulatory subunit B", alpha | PPP2R3A | NM_002718.3 | 5523 | Hs.518155 |
| 624. | protein tyrosine phosphatase, non-receptor type 21 | PTPN21 | NM_007039.2 | 11099 | Hs.437040 |
| 625. | protein tyrosine phosphatase, non-receptor type 3 | PTPN3 | NM_002829.2 | 5774 | Hs.436429 |
| 626. | protein tyrosine phosphatase, receptor type, F | PTPRF | NM_002840 | 5792 | Hs.272062 |
| 627. | protein tyrosine phosphatase, receptor type, K | PTPRK | NM_002844.2 | 5796 | Hs.155919 |
| 628. | protocadherin 21 | PCDH21 (KIAA1775) | BC038799.1 | 92211 | Hs.137556 |
| 629. | protocadherin gamma subfamily B, 7 | PCDHGB7 | NM_032101.1 | 56099 | Hs.368160 |
| 630. | psoriasis susceptibility 1 candidate 2 | PSORS1C2 | NM_014069.1 | 170680 | Hs.146824 |
| 631. | PTK6 protein tyrosine kinase 6 | PTK6 | NM_005975.2 | 5753 | Hs.51133 |
| 632. | Purkinje cell protein 4 like 1 | PCP4L1 | XM_938798.1 | 654790 | Hs.433150 |
| 633. | pyrin-domain containing protein 1 | PYC1 | NM_152901 | 260434 | Hs.58314 |
| 634. | RAB11 family interacting protein 1 (class I) | RAB11FIP1 | NM_001002233.1 | 80223 | Hs.191179 |
| 635. | RAB25, member RAS oncogene family | RAB25 | NM_020387.1 | 57111 | Hs.491308 |
| 636. | RAB27B, member RAS oncogene family | RAB27B | NM_004163.3 | 5874 | Hs.514875 |
| 637. | RAB3D, member RAS oncogene family | RAB3D | NM_004283.2 | 9545 | Hs.567257 |
| 638. | RAB7B, member RAS oncogene family | RAB7B | NM_177403.3 | 338382 | Hs.534612 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 639. | Rap guanine nucleotide exchange factor (GEF)-like 1 | RAPGEFL1 | NM_016339.1 | 51195 | Hs.158530 |
| 640. | Rap2 binding protein 9 | RPIB9 | NM_138290 | 154661 | Hs.411488 |
| 641. | RAR-related orphan receptor A | RORA | NM_002943.2 | 6095 | Hs.511626 |
| 642. | ras homolog gene family, member D | RHOD | NM_014578.2 | 29984 | Hs.15114 |
| 643. | ras homolog gene family, member V | RHOV | NM_133639 | 171177 | Hs.447901 |
| 644. | RAS p21 protein activator 4 | RASA4 | NM_006989.3 | 10156 | Hs.558443 |
| 645. | RAS-like, estrogen-regulated, growth inhibitor | RERG | NM_032918.1 | 85004 | Hs.199487 |
| 646. | regulating synaptic membrane exocytosis 3 | RIMS3 | NM_014747.2 | 9783 | Hs.434924 |
| 647. | repetin | RPTN | XM_937200.1 | 126638 | Hs.376144 |
| 648. | restin (Reed-Steinberg cell-expressed intermediate filament-associated protein) | RSN | NM_002956.2 | 6249 | Hs.524809 |
| 649. | retinoic acid early transcript 1E | RAET1E | NM_139165.1 | 135250 | Hs.511818 |
| 650. | retinol dehydrogenase 12 (all-trans and 9-cis) | RDH12 | NM_152443.1 | 145226 | Hs.415322 |
| 651. | retinol dehydrogenase 16 (all-trans and 13-cis) | RDH16 | NM_003708.2 | 8608 | Hs.134958 |
| 652. | Rhesus blood group, B glycoprotein | RHBG | NM_020407.1 | 57127 | Hs.131835 |
| 653. | Rho guanine nucleotide exchange factor (GEF) 4 | ARHGEF4 | NM_015320.2 | 50649 | Hs.469935 |
| 654. | Rho-guanine nucleotide exchange factor | RGNEF | XM_932952.1 | 643607 | Hs.33254 |
| 655. | rhomboid, veinlet-like 2 (Drosophila) | RHBDL2 | NM_017821.3 | 54933 | Hs.524626 |
| 656. | ribonuclease, RNase A family, 7 | RNASE7 | NM_032572.2 | 84659 | Hs.525206 |
| 657. | ring finger protein 180 | RNF180 | NM_178532 | 285671 | Hs.98890 |
| 658. | ring finger protein 39 | RNF39 | NM_170769.1 | 80352 | Hs.121178 |
| 659. | RNA binding motif protein 35A | RBM35A | NM_001034915.1 | 54845 | Hs.487471 |
| 660. | RNA binding motif protein 35B | RBM35B | NM_024939.2 | 80004 | Hs.436585 |
| 661. | S100 calcium binding protein A12 (calgranulin C) | S100A12 | NM_005621.1 | 6283 | Hs.19413 |
| 662. | S100 calcium binding protein A14 | S100A14 | NM_020672.1 | 57402 | Hs.288998 |
| 663. | S100 calcium binding protein A2 | S100A2 | NM_005978.3 | 6273 | Hs.516484 |
| 664. | S100 calcium binding protein A7 (psoriasin 1) | S100A7 | NM_002963.2 | 6278 | Hs.112408 |
| 665. | S100 calcium binding protein A7-like 1 | S100A7L1 | NM_176823.2 | 338324 | Hs.442337 |
| 666. | S100 calcium binding protein A8 (calgranulin A) | S100A8 | NM_002964.3 | 6279 | Hs.416073 |
| 667. | S100 calcium binding protein A9 (calgranulin B) | S100A9 | NM_002965.2 | 6280 | Hs.112405 |
| 668. | S100 calcium binding protein P | S100P | NM_005980.2 | 6286 | Hs.2962 |
| 669. | sciellin | SCEL | NM_003843 | 8796 | Hs.492938 |
| 670. | sclerostin domain containing 1 | SOSTDC1 | NM_015464 | 25928 | Hs.25956 |
| 671. | secreted LY6/PLAUR domain containing 1 | SLURP1 | NM_020427.2 | 57152 | Hs.103505 |
| 672. | secretoglobin, family 2A, member 2 | SCGB2A2 | NM_002411.1 | 4250 | Hs.46452 |
| 673. | secretory leukocyte peptidase inhibitor | SLPI | NM_003064.2 | 6590 | Hs.517070 |
| 674. | selenoprotein P, plasma, 1 | SEPP1 | NM_005410.2 | 6414 | Hs.275775 |
| 675. | sema domain, immunoglobulin domain (Ig), short basic domain, secreted, (semaphorin) 3F | SEMA3F | NM_004186.2 | 6405 | Hs.32981 |
| 676. | serine (or cysteine) proteinase inhibitor, clade B (ovalbumin), member 13 | SERPINB13 | NM_012397 | 5275 | Hs.241407 |
| 677. | serine palmitoyltransferase, long chain base subunit 2-like (aminotransferase 2) | SPTLC2L | AK075271.1 | 140911 | Hs.425023 |
| 678. | serine peptidase inhibitor, Kazal type 5 | SPINK5 | NM_006846.2 | 11005 | Hs.331555 |
| 679. | serine peptidase inhibitor, Kunitz type 1 | SPINT1 | NM_003710.3 | 6692 | Hs.233950 |
| 680. | serine peptidase inhibitor, Kunitz type, 2 | SPINT2 | NM_021102.2 | 10653 | Hs.31439 |
| 681. | serine/threonine/tyrosine kinase 1 | STYK1 | NM_018423.1 | 55359 | Hs.24979 |
| 682. | serpin peptidase inhibitor, clade A (alpha-1 antiproteinase, antitrypsin), member 12 | SERPINA12 | NM_173850.2 | 145264 | Hs.99476 |
| 683. | serpin peptidase inhibitor, clade B (ovalbumin), member 12 | SERPINB12 | NM_080474.1 | 89777 | Hs.348541 |
| 684. | serpin peptidase inhibitor, clade B (ovalbumin), member 2 | SERPINB2 | NM_002575.1 | 5055 | Hs.514913 |
| 685. | serpin peptidase inhibitor, clade B (ovalbumin), member 3 | SERPINB3 | NM_006919.1 | 6317 | Hs.227948 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 686. | serpin peptidase inhibitor, clade B (ovalbumin), member 4 | SERPINB4 | NM_002974.1 | 6318 | Hs.123035 |
| 687. | serpin peptidase inhibitor, clade B (ovalbumin), member 5 | SERPINB5 | NM_002639 | 5268 | Hs.55279 |
| 688. | serpin peptidase inhibitor, clade B (ovalbumin), member 7 | SERPINB7 | NM_001040147.1 | 8710 | Hs.138202 |
| 689. | serpin peptidase inhibitor, clade B (ovalbumin), member 8 | SERPINB8 | NM_001031848.1 | 5271 | Hs.368077 |
| 690. | SH2 domain containing 3A | SH2D3A | NM_005490.1 | 10045 | Hs.439645 |
| 691. | SH3 domain containing ring finger 2 | SH3RF2 | NM_152550.2 | 153769 | Hs.443728 |
| 692. | SH3 domain protein D19 | SH3D19 | NM_001009555.2 | 152503 | Hs.519018 |
| 693. | SH3-domain binding protein 2 | SH3BP2 | NM_003023.2 | 6452 | Hs.167679 |
| 694. | SH3-domain GRB2-like endophilin B2 | SH3GLB2 | NM_020145.2 | 56904 | Hs.460238 |
| 695. | sidekick homolog 1 (chicken) | SDK1 | NM_152744 | 221935 | Hs.155959 |
| 696. | signal transducing adaptor family member 2 | STAP2 | NM_001013841.1 | 55620 | Hs.194385 |
| 697. | similar to alpha-2-glycoprotein 1, zinc | LOC646282 | AC004522 | 646282 | Hs.568109 |
| 698. | similar to common salivary protein 1 | LOC124220 | NM_145252.2 | 124220 | Hs.105887 |
| 699. | similar to RIKEN cDNA 1810006A16 gene | LOC91862 | NM_052858 | 91862 | Hs.435764 |
| 700. | Similar to RIKEN cDNA 2310002J15 gene | MGC59937 | NM_199001.1 | 375791 | Hs.512469 |
| 701. | similar to WDNM1-like protein | LOC645638 | AA149250 | 645638 | Hs.56105 |
| 702. | skin aspartic protease | SASP | NM_152792.1 | 151516 | Hs.556025 |
| 703. | slit homolog 3 (*Drosophila*) | SLIT3 | NM_003062 | 6586 | Hs.129229 |
| 704. | SMAD in the antisense orientation | DAMS | NM_022001 | 9597 | Hs.167700 |
| 705. | SMAD, mothers against DPP homolog 1 (*Drosophila*) | SMAD1 | NM_005900 | 4086 | Hs.388294 |
| 706. | small breast epithelial mucin | LOC118430 | NM_058173 | 118430 | Hs.348419 |
| 707. | small proline-rich protein 1A | SPRR1A | NM_005987.2 | 6698 | Hs.46320 |
| 708. | small proline-rich protein 1B (cornifin) | SPRR1B | NM_003125.2 | 6699 | Hs.1076 |
| 709. | small proline-rich protein 2A | SPRR2A | NM_005988.2 | 6700 | Hs.355542 |
| 710. | small proline-rich protein 2G | SPRR2G | NM_001014291.2 | 6706 | Hs.490253 |
| 711. | sodium channel, nonvoltage-gated 1 alpha | SCNN1A | NM_001038.4 | 6337 | Hs.130989 |
| 712. | sodium channel, nonvoltage-gated 1, beta (Liddle syndrome) | SCNN1B | NM_000336.1 | 6338 | Hs.414614 |
| 713. | sodium channel, nonvoltage-gated 1, gamma | SCNN1G | NM_001039 | 6340 | Hs.371727 |
| 714. | sodium channel, voltage-gated, type IV, beta | SCN4B | NM_174934.1 | 6330 | Hs.65239 |
| 715. | solute carrier family 1 (high affinity aspartate/glutamate transporter), member 6 | SLC1A6 | NM_005071 | 6511 | Hs.515217 |
| 716. | solute carrier family 15 (oligopeptide transporter), member 1 | SLC15A1 | NM_005073.1 | 6564 | Hs.436893 |
| 717. | solute carrier family 16 (monocarboxylic acid transporters), member 10 | SLC16A10 | NM_018593.3 | 117247 | Hs.520321 |
| 718. | solute carrier family 16 (monocarboxylic acid transporters), member 14 | SLC16A14 | NM_152527.3 | 151473 | Hs.504317 |
| 719. | solute carrier family 18 (vesicular monoamine), member 2 | SLC18A2 | NM_003054.2 | 6571 | Hs.369009 |
| 720. | solute carrier family 2 (facilitated glucose transporter), member 12 | SLC2A12 | NM_145176.2 | 154091 | Hs.486508 |
| 721. | Solute carrier family 22 (extraneuronal monoamine transporter), member 3 | SLC22A3 | NM_021977 | 6581 | Hs.242721 |
| 722. | Solute carrier family 24 (sodium/potassium/calcium exchanger), member 3 | SLC24A3 | NM_020689.3 | 57419 | Hs.211252 |
| 723. | solute carrier family 26, member 9 | SLC26A9 | NM_134325.1 | 115019 | Hs.164073 |
| 724. | solute carrier family 28 (sodium-coupled nucleoside transporter), member 3 | SLC28A3 | NM_022127.1 | 64078 | Hs.535966 |
| 725. | solute carrier family 39 (zinc transporter), member 2 | SLC39A2 | NM_014579.1 | 29986 | Hs.175783 |
| 726. | solute carrier family 4, sodium bicarbonate transporter-like, member 11 | SLC4A11 | NM_032034.1 | 83959 | Hs.105607 |
| 727. | solute carrier family 47, member 2 | SLC47A2 | NM_152908.2 | 146802 | Hs.126830 |
| 728. | solute carrier family 5 (sodium/glucose cotransporter), member 1 | SLC5A1 | NM_000343.1 | 6523 | Hs.1964 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 729. | solute carrier family 6 (amino acid transporter), member 14 | SLC6A14 | NM_007231.1 | 11254 | Hs.522109 |
| 730. | solute carrier family 6 (neurotransmitter transporter, noradrenalin), member 2 | SLC6A2 | NM_001043.2 | 6530 | Hs.78036 |
| 731. | spectrin SH3 domain binding protein 1 | SSH3BP1 | NM_005470 | 10006 | Hs.42710 |
| 732. | spectrin, beta, non-erythrocytic 2 | SPTBN2 | NM_006946.1 | 6712 | Hs.26915 |
| 733. | spermatogenesis associated 18 homolog (rat) | SPATA18 | NM_145263.1 | 132671 | Hs.527090 |
| 734. | sphingomyelin phosphodiesterase 3, neutral membrane (neutral sphingomyelinase II) | SMPD3 | NM_018667.2 | 55512 | Hs.368421 |
| 735. | sphingosine-1-phosphate phosphotase 2 | SGPP2 | NM_152386.2 | 130367 | Hs.210043 |
| 736. | SRY (sex determining region Y)-box 15 | SOX15 | NM_006942.1 | 6665 | Hs.95582 |
| 737. | SRY (sex determining region Y)-box 7 | SOX7 | NM_031439.2 | 83595 | Hs.213194 |
| 738. | START domain containing 5 | STARD5 | NM_030574.2 | 80765 | Hs.513075 |
| 739. | STEAP family member 4 | STEAP4 | AK026806.1 | 79689 | Hs.521008 |
| 740. | steroid-5-alpha-reductase, alpha polypeptide 1 (3-oxo-5 alpha-steroid delta 4-dehydrogenase alpha 1) | SRD5A1 | NM_001047.2 | 6715 | Hs.552 |
| 741. | steroidogenic acute regulator | STAR | NM_000349.2 | 6770 | Hs.521535 |
| 742. | stonin 2 | STN2 | NM_033104 | 85439 | Hs.14248 |
| 743. | stratifin | SFN | NM_006142.3 | 2810 | Hs.523718 |
| 744. | sulfotransferase family 1E, estrogen-preferring, member 1 | SULT1E1 | NM_005420.2 | 6783 | Hs.479898 |
| 745. | sulfotransferase family, cytosolic, 2B, member 1 | SULT2B1 | NM_004605.2 | 6820 | Hs.369331 |
| 746. | suppression of tumorigenicity 14 (colon carcinoma) | ST14 | NM_021978.3 | 6768 | Hs.504315 |
| 747. | suprabasin | SBSN | NM_198538.1 | 374897 | Hs.433484 |
| 748. | surfactant, pulmonary-associated protein D | SFTPD | NM_003019.4 | 6441 | Hs.253495 |
| 749. | sushi domain containing 4 | SUSD4 | NM_017982.2 | 55061 | Hs.558826 |
| 750. | synaptotagmin-like 1 | SYTL1 | NM_032872.1 | 84958 | Hs.469175 |
| 751. | syndecan 1 | SDC1 | NM_001006946.1 | 6382 | Hs.224607 |
| 752. | syndecan binding protein (syntenin) 2 | SDCBP2 | NM_015685.3 | 27111 | Hs.516836 |
| 753. | syntaxin 19 | STX19 | NM_001001850.1 | 415117 | Hs.533086 |
| 754. | synuclein, alpha interacting protein (synphilin) | SNCAIP | NM_005460.2 | 9627 | Hs.426463 |
| 755. | T-box 1 | TBX1 | NM_005992.1 | 6899 | Hs.173984 |
| 756. | T-cell lymphoma invasion and metastasis 1 | TIAM1 | NM_003253.1 | 7074 | Hs.517228 |
| 757. | t-complex 11 (mouse) like 2 | TCP11L2 | NM_152772.1 | 255394 | Hs.132050 |
| 758. | tensin 4 | TNS4 | NM_032865.3 | 84951 | Hs.438292 |
| 759. | tetra-peptide repeat homeobox-like | TPRXL | NM_182629 | 348825 | Hs.529180 |
| 760. | tetraspanin similiar to uroplakin 1 | LOC90139 | NM_130783 | 90139 | Hs.385634 |
| 761. | tetratricopeptide repeat domain 12 | TTC12 | BC032355.1 | 54970 | Hs.288772 |
| 762. | tetratricopeptide repeat domain 18 | TTC18 | NM_145170.2 | 118491 | Hs.549236 |
| 763. | tetratricopeptide repeat domain 22 | TTC22 | NM_017904.1 | 55001 | Hs.16230 |
| 764. | tetratricopeptide repeat domain 9 | TTC9 | XM_938197.1 | 23508 | Hs.79170 |
| 765. | three prime repair exonuclease 2 | TREX2 | NM_080701.3 | 11219 | Hs.170835 |
| 766. | thymic stromal co-transporter | TSCOT | NM_033051.2 | 57864 | Hs.512668 |
| 767. | thyroid hormone receptor, beta (erythroblastic leukemia viral (v-erb-a) oncogene homolog 2, avian) | THRB | NM_000461.3 | 7068 | Hs.187861 |
| 768. | TIGA1 | TIGA1 | NM_053000 | 114915 | Hs.12082 |
| 769. | Tight junction protein 2 (zona occludens 2) | TJP2 | NM_201629.1 | 9414 | Hs.50382 |
| 770. | transcription elongation factor A (SII), 3 | TCEA3 | NM_003196.1 | 6920 | Hs.148105 |
| 771. | transcription factor 4 | TCF4 | NM_003199.1 | 6925 | Hs.200285 |
| 772. | transcription factor AP-2 beta (activating enhancer binding protein 2 beta) | TFAP2B | NM_003221.2 | 7021 | Hs.33102 |
| 773. | transforming growth factor, alpha | TGFA | NM_003236.1 | 7039 | Hs.170009 |
| 774. | transforming, acidic coiled-coil containing protein 2 | TACC2 | NM_006997 | 10579 | Hs.501252 |
| 775. | transglutaminase 1 (K polypeptide epidermal type I, protein-glutamine-gamma-glutamyltransferase) | TGM1 | NM_000359.1 | 7051 | Hs.508950 |
| 776. | transglutaminase 3 (E polypeptide, protein-glutamine-gamma-glutamyltransferase) | TGM3 | NM_003245.2 | 7053 | Hs.2022 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 777. | transglutaminase 5 | TGM5 | NM_004245.2 | 9333 | Hs.129719 |
| 778. | transient receptor potential cation channel, subfamily V, member 1 | TRPV1 | NM_018727.4 | 7442 | Hs.558415 |
| 779. | transmembrane protease, serine 11D | TMPRSS11D | NM_004262.2 | 9407 | Hs.132195 |
| 780. | transmembrane protease, serine 13 | TMPRSS13 | NM_032046.1 | 84000 | Hs.266308 |
| 781. | transmembrane protease, serine 4 | TMPRSS4 | NM_019894.2 | 56649 | Hs.161985 |
| 782. | transmembrane protein 125 | TMEM125 | NM_144626.1 | 128218 | Hs.104476 |
| 783. | transmembrane protein 154 | TMEM154 | NM_152680.1 | 201799 | Hs.518900 |
| 784. | transmembrane protein 16A | TMEM16A | NM_018043.4 | 55107 | Hs.503074 |
| 785. | transmembrane protein 16J | TMEM16J | NM_001012302.1 | 338440 | Hs.501622 |
| 786. | transmembrane protein 184A | TMEM184A | NM_152689.2 | 202915 | Hs.556755 |
| 787. | transmembrane protein 23 | TMEM23 | NM_147156.3 | 259230 | Hs.386215 |
| 788. | transmembrane protein 30B | TMEM30B | NM_001017970.1 | 161291 | Hs.146180 |
| 789. | transmembrane protein 40 | TMEM40 | NM_018306.2 | 55287 | Hs.475502 |
| 790. | transmembrane protein 45A | TMEM45A | NM_018004.1 | 55076 | Hs.126598 |
| 791. | transmembrane protein 45B | TMEM45B | NM_138788.2 | 120224 | Hs.504301 |
| 792. | transmembrane protein 79 | TMEM79 | NM_032323.1 | 84283 | Hs.347408 |
| 793. | tripartite motif-containing 29 | TRIM29 | NM_012101 | 23650 | Hs.504115 |
| 794. | tripartite motif-containing 31 | TRIM31 | NM_007028 | 11074 | Hs.91096 |
| 795. | tripartite motif-containing 7 | TRIM7 | NM_203294.1 | 81786 | Hs.487412 |
| 796. | trypsinogen C | TRY6 | NR_001296.2 | 154754 | Hs.697092 |
| 797. | tryptase alpha/beta 1 | TPSAB1 | NM_003294.3 | 7177 | Hs.405479 |
| 798. | tryptase beta 2 | TPSB2 | NM_024164.5 | 64499 | Hs.592982 |
| 799. | tubulin, alpha 1 (testis specific) | TUBA1 | NM_006000.1 | 7277 | Hs.75318 |
| 800. | tuftelin 1 | TUFT1 | NM_020127.1 | 7286 | Hs.489922 |
| 801. | tumor necrosis factor (ligand) superfamily, member 10 | TNFSF10 | NM_003810.2 | 8743 | Hs.478275 |
| 802. | tumor necrosis factor receptor superfamily, member 25 | TNFRSF25 | NM_003790.2 | 8718 | Hs.462529 |
| 803. | tumor protein D52-like 1 | TPD52L1 | NM_001003395.1 | 7164 | Hs.201482 |
| 804. | tumor protein p73-like | TP73L | NM_003722 | 8626 | Hs.137569 |
| 805. | tumor-associated calcium signal transducer 1 | TACSTD1 | NM_002354.1 | 4072 | Hs.692 |
| 806. | tumor-associated calcium signal transducer 2 | TACSTD2 | NM_002353.1 | 4070 | Hs.23582 |
| 807. | twist homolog 2 (*Drosophila*) | TWIST2 | NM_057179 | 117581 | Hs.422585 |
| 808. | ubiquitin protein ligase E3A (human papilloma virus E6-associated protein, Angelman syndrome) | UBE3A | NM_000462.2 | 7337 | Hs.22543 |
| 809. | Ubiquitin specific peptidase 2 | USP2 | NM_004205.3 | 9099 | Hs.524085 |
| 810. | UDP glucuronosyltransferase 1 familly, polypeptide A1 | UGT1A1 | NM_000463.2 | 54658 | Hs.554822 |
| 811. | UDP-N-acetyl-alpha-D-galactosamine:polypeptide N-acetylgalactosaminyltransferase 6 (GalNAc-T6) | GALNT6 | NM_007210.2 | 11226 | Hs.505575 |
| 812. | unc-93 homolog A (*C. elegans*) | UNC93A | NM_018974.2 | 54346 | Hs.145911 |
| 813. | vasoactive intestinal peptide receptor 1 | VIPR1 | NM_004624.2 | 7433 | Hs.348500 |
| 814. | vav 3 oncogene | VAV3 | NM_006113.3 | 10451 | Hs.267659 |
| 815. | vestigial like 3 (*Drosophila*) | VGLL3 | NM_016206.2 | 389136 | Hs.435013 |
| 816. | v-ets erythroblastosis virus E26 oncogene homolog 2 (avian) | ETS2 | NM_005239.4 | 2114 | Hs.517296 |
| 817. | visinin-like 1 | VSNL1 | NM_003385.4 | 7447 | Hs.444212 |
| 818. | v-maf musculoaponeurotic fibrosarcoma oncogene homolog (avian) | MAF | NM_005360 | 4094 | Hs.134859 |
| 819. | WAP four-disulfide core domain 12 | WFDC12 | NM_080869.1 | 128488 | Hs.352180 |
| 820. | WAP four-disulfide core domain 5 | WFDC5 | NM_145652.2 | 149708 | Hs.375031 |
| 821. | WD repeat domain 66 | WDR66 | BC036233.1 | 144406 | Hs.507125 |
| 822. | wingless-type MMTV integration site family, member 11 | WNT11 | NM_004626.2 | 7481 | Hs.108219 |
| 823. | wingless-type MMTV integration site family, member 3 | WNT3 | NM_030753.3 | 7473 | Hs.445884 |
| 824. | wingless-type MMTV integration site family, member 4 | WNT4 | NM_030761.3 | 54361 | Hs.25766 |
| 825. | wingless-type MMTV integration site family, member 5B | WNT5B | NM_030775.2 | 81029 | Hs.306051 |
| 826. | X Kell blood group precursor-related, X-linked | XKRX | NM_212559.1 | 402415 | Hs.364911 |
| 827. | X102 protein | X102 | NM_030879 | 63969 | Hs.248065 |
| 828. | Xg blood group (pseudoautosomal boundary-divided on the X chromosome) | XG | NM_175569.1 | 7499 | Hs.179675 |

TABLE A-continued

Genes differentially expressed in metastatic melanoma. Expression of the genes listed in this table is decreased relative to non-metastatic samples.

| | Gene description | Gene Symbol | GenBank ID | Entrez Gene ID | UniGene ID |
|---|---|---|---|---|---|
| 829. | YOD1 OTU deubiquinating enzyme 1 homolog (yeast) | YOD1 | NM_018566.3 | 55432 | Hs.391944 |
| 830. | zinc and ring finger 1 | ZNRF1 | NM_032268.3 | 84937 | Hs.427284 |
| 831. | zinc finger and BTB domain containing 3 | ZBTB3 | NM_024784.2 | 79842 | Hs.558545 |
| 832. | zinc finger and BTB domain containing 7C | ZBTB7C | NM_001039360.1 | 201501 | Hs.515388 |
| 833. | zinc finger protein 165 | ZNF165 | NM_003447.2 | 7718 | Hs.55481 |
| 834. | zinc finger protein 185 (LIM domain) | ZNF185 | NM_007150.1 | 7739 | Hs.16622 |
| 835. | zinc finger protein 273 | ZNF273 | AU132789 | 10793 | Hs.386264 |
| 836. | zinc finger protein 42 | ZFP42 | NM_174900.3 | 132625 | Hs.335787 |
| 837. | zinc finger protein 662 | ZNF662 | NM_207404.2 | 389114 | Hs.293388 |
| 838. | zinc finger protein 67 homolog (mouse) | ZFP67 | NM_015872 | 51043 | Hs.159265 |
| 839. | zinc finger protein 682 | ZNF682 | NM_033196.1 | 91120 | Hs.306298 |
| 840. | zinc finger protein 750 | ZNF750 | NM_024702.1 | 79755 | Hs.558544 |
| 841. | zinc finger, DHHC-type containing 21 | ZDHHC21 | NM_178566.2 | 340481 | Hs.561951 |
| 842. | similar to cystin 1 | LOC649824 | XM_938892 | 649824 | Hs.27092 |
| 843. | NPC-A-5 | LOC642587 | AK091113 | 91170 | Hs.301885 |
| 844. | hypothetical gene supported by BC035064 | LOC285259 | AI703273 | 285259 | Hs.146159 |
| 845. | hypothetical gene supported by BC020554 | LOC284974 | AI928242 | 284974 | Hs.119903 |
| 846. | hypothetical gene supported by BC007386 | LOC284668 | BE672487 | 284668 | Hs.25766 |
| 847. | hypothetical gene supported by AL137325 | LOC284456 | AL137325 | 284456 | Hs.406781 |
| 848. | hypothetical gene supported by BC034640 | LOC284224 | BC034640 | 284224 | Hs.382000 |
| 849. | similar to seven transmembrane helix receptor | LOC283929 | BG109230 | 283929 | Hs.374278 |
| 850. | similar to zinc finger protein 366 | LOC254647 | BE858194 | 254647 | Hs.323053 |
| 851. | hypothetical gene supported by AL117529 | LOC221495 | AL117529 | 221495 | Hs.406762 |
| 852. | hypothetical gene supported by AL137430 | LOC221042 | AL137430 | 221042 | Hs.380965 |
| 853. | similar to p53-induced protein PIGPC1 | LOC204288 | AI049608 | 204288 | Hs.355517 |
| 854. | hypothetical gene supported by AL117570 | LOC145739 | AL117570 | 145739 | Hs.375657 |
| 855. | Uncharacterized transcript supported by AW195351 found within the Catenin delta 1 locus | — | AW195351 | — | Hs.250520 |
| 856. | Uncharacterized transcript supported by AA418074 | — | AA418074 | — | Hs.110286 |
| 857. | Gene supported by sequence info. | — | AI888057 | — | — |
| 858. | Gene supported by sequence info. | — | BG484769 | 342289 | Hs.115838 |
| 859. | Gene supported by sequence info. | — | XM_933918 | 646769 | Hs.115838 |
| 860. | Gene supported by sequence info. | — | AK000090 | — | — |
| 861. | Gene supported by sequence info. | — | AA863389 | — | — |
| 862. | Gene supported by sequence info. | — | AW135306 | — | Hs.444277 |
| 863. | Gene supported by sequence info. | — | AF005082 | — | Hs.516420 |
| 864. | Gene supported by sequence info. | — | R81445 | — | — |
| 865. | Gene supported by sequence info. | — | AL050153 | — | — |
| 866. | Gene supported by sequence info. | — | AI934364 | — | Hs.145761 |
| 867. | Gene supported by sequence info. | — | AW131450 | — | Hs.121070 |
| 868. | Gene supported by sequence info. | — | AI832594 | — | Hs.471433 |
| 869. | Gene supported by sequence info. | — | N73742 | — | Hs.36288 |
| 870. | Gene supported by sequence info. | — | BE674309 | — | Hs.418279 |
| 871. | Gene supported by sequence info. | — | AU158573 | — | Hs.288926 |
| 872. | Gene supported by sequence info. | — | AW022607 | — | Hs.379253 |
| 873. | Gene supported by sequence info. | — | R77414 | — | Hs.33355 |
| 874. | Gene supported by sequence info. | — | AU155612 | — | Hs.269545 |
| 875. | Gene supported by sequence info. | — | AI089783 | — | Hs.123307 |
| 876. | Gene supported by sequence info. | — | AL359055 | — | Hs.390270 |
| 877. | Gene supported by sequence info. | — | BE645279 | — | Hs.29792 |
| 878. | Gene supported by sequence info. | — | AI939452 | — | Hs.445064 |
| 879. | Gene supported by sequence info. | — | AW974998 | — | Hs.222430 |
| 880. | Gene supported by sequence info. | — | AK096998 | — | Hs.29952 |
| 881. | Gene supported by sequence info. | — | AW025141 | — | Hs.432504 |
| 882. | Gene supported by sequence info. | — | AW452355 | — | Hs.445872 |
| 883. | Gene supported by sequence info. | — | AL137535 | — | Hs.15806 |
| 884. | Gene supported by sequence info. | — | AA516469 | — | Hs.433643 |
| 885. | Gene supported by sequence info. | — | AU147515 | — | Hs.406812 |
| 886. | Gene supported by sequence info. | — | AW974077 | — | Hs.283349 |

TABLE A-continued

Genes differentially expressed in metastatic melanoma. Expression
of the genes listed in this table is decreased relative to non-metastatic samples.

| | Gene description | Gene Symbol | GenBank ID | Entrez Gene ID | UniGene ID |
|---|---|---|---|---|---|
| 887. | Gene supported by sequence info. | — | AA890487 | — | Hs.24598 |
| 888. | Gene supported by sequence info. | — | N66591 | — | Hs.440646 |
| 889. | Gene supported by sequence info. | — | AU151465 | — | Hs.224012 |
| 890. | Gene supported by sequence info. | — | AW517412 | — | Hs.150757 |
| 891. | Gene supported by sequence info. | — | AU147518 | — | Hs.499320 |
| 892. | Gene supported by sequence info. | — | BF111088 | — | Hs.201446 |
| 893. | Gene supported by sequence info. | — | AI924046 | — | Hs.119567 |
| 894. | Gene supported by sequence info. | — | AI971251 | — | Hs.443740 |
| 895. | Gene supported by sequence info. | — | R48254 | — | Hs.344872 |
| 896. | Gene supported by sequence info. | — | AI096634 | — | Hs.371677 |
| 897. | Gene supported by sequence info. | — | BF056273 | — | Hs.188920 |
| 898. | Gene supported by sequence info. | — | AI457984 | — | Hs.165900 |
| 899. | Gene supported by sequence info. | — | BG429255 | — | Hs.42376 |
| 900. | Gene supported by sequence info. | — | AI090487 | — | Hs.168325 |
| 901. | Gene supported by sequence info. | — | AI659426 | — | Hs.443287 |
| 902. | Gene supported by sequence info. | — | T51136 | — | Hs.421262 |
| 903. | Gene supported by sequence info. | — | AW291545 | — | Hs.445978 |
| 904. | Gene supported by sequence info. | — | AA687916 | — | Hs.117295 |
| 905. | Gene supported by sequence info. | — | BF114646 | — | Hs.19339 |
| 906. | Gene supported by sequence info. | — | AW014647 | — | Hs.432924 |
| 907. | Gene supported by sequence info. | — | W96062 | — | Hs.373964 |
| 908. | Gene supported by sequence info. | — | AI373107 | — | Hs.110334 |
| 909. | Gene supported by sequence info. | — | AA758732 | — | Hs.473374 |
| 910. | Gene supported by sequence info. | — | H15900 | — | Hs.31395 |
| 911. | Gene supported by sequence info. | — | AL515437 | — | Hs.143718 |
| 912. | Gene supported by sequence info. | — | AI334358 | — | Hs.124597 |
| 913. | Gene supported by sequence info. | — | AI458439 | — | Hs.159115 |
| 914. | Gene supported by sequence info. | — | AL157448 | — | Hs.375671 |
| 915. | Gene supported by sequence info. | — | AK022350 | — | Hs.511707 |
| 916. | Gene supported by sequence info. | — | AI972146 | — | Hs.192756 |
| 917. | Gene supported by sequence info. | — | H22005 | — | Hs.120725 |
| 918. | Gene supported by sequence info. | — | BF245284 | — | Hs.354427 |
| 919. | Gene supported by sequence info. | — | AI093221 | — | Hs.155965 |
| 920. | Gene supported by sequence info. | — | BC019703 | — | Hs.145626 |
| 921. | Gene supported by sequence info. | — | AU146924 | — | Hs.188691 |
| 922. | Gene supported by sequence info. | — | AI829605 | — | Hs.436077 |
| 923. | Gene supported by sequence info. | — | AW301393 | — | Hs.493477 |
| 924. | Gene supported by sequence info. | — | H88112 | — | Hs.234478 |
| 925. | Gene supported by sequence info. | — | AW173504 | — | Hs.76704 |
| 926. | Gene supported by sequence info. | — | AA565852 | — | Hs.71947 |
| 927. | Gene supported by sequence info. | — | AI022066 | — | Hs.372209 |
| 928. | Gene supported by sequence info. | — | W68845 | — | Hs.324323 |
| 929. | Gene supported by sequence info. | — | BI598831 | — | Hs.434643 |
| 930. | Gene supported by sequence info. | — | AU159446 | — | Hs.498954 |
| 931. | Gene supported by sequence info. | — | BC040322 | — | Hs.44330 |
| 932. | Gene supported by sequence info. | — | AA826931 | — | Hs.491024 |
| 933. | Gene supported by sequence info. | — | BC029440 | — | Hs.374843 |
| 934. | Gene supported by sequence info. | — | AI950023 | — | Hs.270751 |
| 935. | Gene supported by sequence info. | — | AV739182 | — | Hs.113150 |
| 936. | Gene supported by sequence info. | — | AI829721 | — | Hs.482381 |
| 937. | Gene supported by sequence info. | — | AA876179 | — | Hs.134650 |
| 938. | Gene supported by sequence info. | — | AK024907 | — | Hs.306723 |
| 939. | Gene supported by sequence info. | — | AW451197 | — | Hs.113418 |
| 940. | Gene supported by sequence info. | — | BF224444 | — | Hs.127274 |
| 941. | Gene supported by sequence info. | — | AW130600 | — | Hs.99472 |
| 942. | Gene supported by sequence info. | — | AI042373 | — | Hs.132917 |
| 943. | Gene supported by sequence info. | — | AL038973 | — | Hs.144873 |
| 944. | Gene supported by sequence info. | — | BE672408 | — | Hs.107708 |
| 945. | Gene supported by sequence info. | — | AW139091 | — | Hs.161158 |
| 946. | Gene supported by sequence info. | — | AW025023 | — | Hs.234478 |
| 947. | Gene supported by sequence info. | — | BE500942 | — | Hs.170540 |
| 948. | Gene supported by sequence info. | — | AW242920 | — | Hs.129368 |
| 949. | Gene supported by sequence info. | — | AA603472 | — | Hs.28456 |
| 950. | Gene supported by sequence info. | — | AU144382 | — | Hs.501925 |
| 951. | Gene supported by sequence info. | — | AL833150 | — | Hs.327631 |
| 952. | Gene supported by sequence info. | — | BM992214 | — | Hs.314518 |
| 953. | Gene supported by sequence info. | — | AL359055 | — | Hs.390270 |
| 954. | Gene supported by sequence info. | — | AA167323 | — | Hs.188682 |
| 955. | Gene supported by sequence info. | — | AI970797 | — | Hs.133152 |
| 956. | Gene supported by sequence info. | — | AI733037 | — | Hs.129990 |
| 957. | Gene supported by sequence info. | — | H15396 | — | Hs.107510 |
| 958. | Gene supported by sequence info. | — | BF055060 | — | Hs.387100 |
| 959. | Gene supported by sequence info. | — | N30188 | — | Hs.93739 |

TABLE A-continued

Genes differentially expressed in metastatic melanoma. Expression of the genes listed in this table is decreased relative to non-metastatic samples.

| Gene description | Gene Symbol | GenBank ID | Entrez Gene ID | UniGene ID |
|---|---|---|---|---|
| 960. Gene supported by sequence info. | — | AK056784 | — | Hs.224056 |
| 961. Gene supported by sequence info. | — | AU147152 | — | Hs.118317 |
| 962. Gene supported by sequence info. | — | AI341837 | — | Hs.436105 |
| 963. Gene supported by sequence info. | — | AI051950 | — | Hs.99472 |
| 964. Gene supported by sequence info. | — | N91149 | — | Hs.279639 |
| 965. Gene supported by sequence info. | — | AI191905 | — | Hs.228982 |
| 966. Gene supported by sequence info. | — | BF508208 | — | Hs.240074 |
| 967. Gene supported by sequence info. | — | AU147861 | — | Hs.188082 |
| 968. Gene supported by sequence info. | — | AA779333 | — | Hs.20158 |
| 969. Gene supported by sequence info. | — | AW274846 | — | Hs.19339 |
| 970. Gene supported by sequence info. | — | AL137616 | — | Hs.30483 |
| 971. Gene supported by sequence info. | — | AK025151 | — | Hs.268597 |
| 972. Gene supported by sequence info. | — | BF961733 | — | Hs.445604 |
| 973. Gene supported by sequence info. | — | AI079329 | — | Hs.271876 |
| 974. Gene supported by sequence info. | — | AW292830 | — | Hs.435001 |
| 975. Gene supported by sequence info. | — | BC040965 | — | Hs.270114 |
| 976. Gene supported by sequence info. | — | AA933082 | — | Hs.126883 |
| 977. Gene supported by sequence info. | — | BC038784 | — | Hs.385767 |
| 978. Gene supported by sequence info. | — | AW302207 | — | Hs.228982 |
| 979. Gene supported by sequence info. | — | AK025378 | — | Hs.466700 |
| 980. Gene supported by sequence info. | — | R97781 | — | Hs.247150 |
| 981. Gene supported by sequence info. | — | AI655611 | — | Hs.124863 |
| 982. Gene supported by sequence info. | — | BF847120 | — | Hs.318887 |
| 983. Gene supported by sequence info. | — | AA461490 | — | Hs.66072 |
| 984. Gene supported by sequence info. | — | BC034636 | — | Hs.385523 |
| 985. Gene supported by sequence info. | — | N66393 | — | Hs.102754 |
| 986. Gene supported by sequence info. | — | AI637733 | — | Hs.220624 |
| 987. Gene supported by sequence info. | — | AA583038 | — | Hs.349207 |
| 988. Gene supported by sequence info. | — | AU156822 | — | Hs.287577 |
| 989. Gene supported by sequence info. | — | BE222843 | — | Hs.231852 |
| 990. Gene supported by sequence info. | — | BC040965 | — | Hs.270114 |
| 991. Gene supported by sequence info. | — | AI147310 | — | Hs.146730 |
| 992. Gene supported by sequence info. | — | AI417988 | — | Hs.37648 |
| 993. Gene supported by sequence info. | — | AA825510 | — | Hs.124304 |
| 994. Gene supported by sequence info. | — | BG260087 | — | Hs.7956 |
| 995. Gene supported by sequence info. | — | AI627679 | — | Hs.374420 |
| 996. Gene supported by sequence info. | — | AW070877 | — | Hs.432615 |
| 997. Gene supported by sequence info. | — | AA922936 | — | Hs.110039 |
| 998. Gene supported by sequence info. | — | AI935541 | — | Hs.127009 |
| 999. Gene supported by sequence info. | — | T68445 | — | Hs.76704 |
| 1000. Gene supported by sequence info. | — | AK097810 | — | Hs.146493 |
| 1001. Gene supported by sequence info. | — | AW081982 | — | Hs.59507 |
| 1002. Gene supported by sequence info. | — | AI399889 | — | Hs.381411 |
| 1003. Gene supported by sequence info. | — | BC039513 | — | Hs.407575 |
| 1004. Gene supported by sequence info. | — | AL512727 | — | Hs.232127 |
| 1005. Gene supported by sequence info. | — | AK021990 | — | Hs.287466 |
| 1006. Gene supported by sequence info. | — | AK000106 | — | Hs.272227 |
| 1007. Gene supported by sequence info. | — | AI819863 | — | Hs.106243 |
| 1008. Gene supported by sequence info. | — | AI743489 | — | Hs.322679 |
| 1009. Gene supported by sequence info. | — | AL050204 | — | Hs.28540 |
| 1010. Gene supported by sequence info. | — | AW006352 | — | Hs.159643 |
| 1011. Gene supported by sequence info. | — | BE843544 | — | Hs.444613 |
| 1012. Gene supported by sequence info. | — | AI796535 | — | Hs.504568 |
| 1013. Gene supported by sequence info. | — | AF086294 | — | Hs.125844 |
| 1014. Gene supported by sequence info. | — | BG290650 | — | Hs.134876 |
| 1015. Gene supported by sequence info. | — | AV741130 | — | Hs.173704 |
| 1016. Gene supported by sequence info. | — | AI928035 | — | Hs.282089 |
| 1017. Gene supported by sequence info. | — | AI674565 | — | Hs.8379 |
| 1018. Gene supported by sequence info. | — | AI085338 | — | Hs.375591 |
| 1019. Gene supported by sequence info. | — | AA034012 | — | Hs.37648 |
| 1020. Gene supported by sequence info. | — | AI288186 | — | Hs.58611 |
| 1021. Gene supported by sequence info. | — | AK024927 | — | Hs.152423 |
| 1022. Gene supported by sequence info. | — | BG149557 | — | Hs.37648 |

TABLE B

Genes differentially expressed in metastatic melanoma. Expression
of the genes listed in this table is increased relative to non-metastatic samples.

| Gene description | Gene Symbol | GenBank ID | Entrez Gene ID | UniGene ID |
|---|---|---|---|---|
| 1023. ATP-binding cassette, sub-family B (MDR/TAP), member 5 | ABCB5 | NM_178559.3 | 340273 | Hs.404102 |
| 1024. abhydrolase domain containing 10 | ABHD10 | NM_018394.1 | 55347 | Hs.477115 |
| 1025. acyl-CoA synthetase long-chain family member 3 | ACSL3 | NM_004457 | 2181 | Hs.268012 |
| 1026. alkylglycerone phosphate synthase | AGPS | NM_003659.2 | 8540 | Hs.516543 |
| 1027. v-akt murine thymoma viral oncogene homolog 3 (protein kinase B, gamma) | AKT3 | NM_005465.3 | 10000 | Hs.498292 |
| 1028. anillin, actin binding protein (scraps homolog, *Drosophila*) | ANLN | NM_018685.2 | 54443 | Hs.62180 |
| 1029. adaptor-related protein complex 1, sigma 2 subunit | AP1S2 | NM_003916 | 8905 | Hs.121592 |
| 1030. apolipoprotein C-II | APOC2 | NM_000483.3 | 344 | Hs.75615 |
| 1031. ATPase family, AAA domain containing 2 | ATAD2 | NM_014109.2 | 29028 | Hs.370834 |
| 1032. activating transcription factor 6 | ATF6 | NM_007348 | 22926 | Hs.492740 |
| 1033. ataxia telangiectasia mutated (includes complementation groups A, C and D) | ATM | NM_000051 | 472 | Hs.435561 |
| 1034. ATPase, H+ transporting, lysosomal 42 kDa, V1 subunit C, isoform 1 | ATP6V1C1 | NM_001007254.1 | 528 | Hs.86905 |
| 1035. ATPase, Class 1, type 8B, member 2 | ATP8B2 | NM_020452.2 | 57198 | Hs.435700 |
| 1036. antizyme inhibitor 1 | AZIN1 | NM_148174.2 | 51582 | Hs.459106 |
| 1037. UDP-GlcNAc:betaGal beta-1,3-N-acetylglucosaminyltransferase 1 | B3GNT1 | NM_006577.5 | 10678 | Hs.173203 |
| 1038. UDP-Gal:betaGlcNAc beta 1,4-galactosyltransferase, polypeptide 6 | B4GALT6 | NM_004775.2 | 9331 | Hs.464848 |
| 1039. bromodomain adjacent to zinc finger domain, 1B | BAZ1B | NM_023005.2 | 9031 | Hs.488671 |
| 1040. BRCA2 and CDKN1A interacting protein | BCCIP | NM_016567.2 | 56647 | Hs.370292 |
| 1041. BCL2-related protein A1 | BCL2A1 | NM_004049.2 | 597 | Hs.227817 |
| 1042. bifunctional apoptosis regulator | BFAR | NM_016561.1 | 51283 | Hs.435556 |
| 1043. bicaudal D homolog 1 (*Drosophila*) | BICD1 | NM_001714 | 636 | Hs.505202 |
| 1044. baculoviral IAP repeat-containing 5 (survivin) | BIRC5 | NM_001012270.1 | 332 | Hs.514527 |
| 1045. barren homolog 1 (*Drosophila*) | BRRN1 | NM_015341.3 | 23397 | Hs.308045 |
| 1046. butyrophilin, subfamily 2, member A1 | BTN2A1 | NM_007049.2 | 11120 | Hs.159028 |
| 1047. BUB1 budding uninhibited by benzimidazoles 1 homolog (yeast) | BUB1 | NM_004336.2 | 699 | Hs.469649 |
| 1048. chromosome 12 open reading frame 11 | C12orf11 | NM_018164.1 | 55726 | Hs.505077 |
| 1049. chromosome 12 open reading frame 24 | C12orf24 | NM_013300.1 | 29902 | Hs.436618 |
| 1050. core 1 synthase, glycoprotein-N-acetylgalactosamine 3-beta-galactosyltransferase, 1 | C1GALT1 | NM_020156.1 | 56913 | Hs.239666 |
| 1051. chromosome 1 open reading frame 103 | C1orf103 | NM_018372.3 | 55791 | Hs.25245 |
| 1052. chromosome 1 open reading frame 67 | C1orf67 | XM_290922.4 | 200095 | Hs.133977 |
| 1053. chromosome 1 open reading frame 90 | C1orf90 | BC004269.1 | 84734 | Hs.18449 |
| 1054. chromosome 20 open reading frame 104 | C20orf104 | NM_016436 | 51230 | Hs.301055 |
| 1055. chromosome 20 open reading frame 30 | C20orf30 | NM_001009924.1 | 29058 | Hs.472024 |
| 1056. chromosome 7 open reading frame 11 | C7orf11 | NM_138701.1 | 136647 | Hs.129159 |
| 1057. chromosome 9 open reading frame 100 | C9orf100 | NM_032818.2 | 84904 | Hs.277026 |
| 1058. calumenin | CALU | NM_001219.2 | 813 | Hs.7753 |
| 1059. cell cycle associated protein 1 | CAPRIN1 | NM_005898.4 | 4076 | Hs.471818 |
| 1060. cell division cycle 2, G1 to S and G2 to M | CDC2 | NM_001786 | 983 | Hs.334562 |
| 1061. CDC42 effector protein (Rho GTPase binding) 3 | CDC42EP3 | NM_006449.3 | 10602 | Hs.369574 |
| 1062. CDC45 cell division cycle 45-like (*S. cerevisiae*) | CDC45L | NM_003504.3 | 8318 | Hs.474217 |
| 1063. CDC6 cell division cycle 6 homolog (*S. cerevisiae*) | CDC6 | NM_001254.3 | 990 | Hs.405958 |
| 1064. cell division cycle associated 1 | CDCA1 | NM_031423.2 | 83540 | Hs.234545 |
| 1065. cell division cycle associated 3 | CDCA3 | NM_031299.3 | 83461 | Hs.524216 |
| 1066. cyclin-dependent kinase 2 | CDK2 | NM_001798.2 | 1017 | Hs.19192 |
| 1067. centromere protein A, 17 kDa | CENPA | NM_001809 | 1058 | Hs.1594 |
| 1068. centromere protein F, 350/400ka (mitosin) | CENPF | NM_0.16343 | 1063 | Hs.497741 |
| 1069. centromere protein N | CENPN | NM_018455.3 | 55839 | Hs.283532 |
| 1070. cofilin 2 (muscle) | CFL2 | NM_021914.5 | 1073 | Hs.180141 |
| 1071. chromodomain helicase DNA binding protein 7 | CHD7 | NM_017780.2 | 55636 | Hs.20395 |
| 1072. carbohydrate (chondroitin 4) sulfotransferase 11 | CHST11 | NM_018413.2 | 50515 | Hs.17569 |

TABLE B-continued

Genes differentially expressed in metastatic melanoma. Expression of the genes listed in this table is increased relative to non-metastatic samples.

| Gene description | Gene Symbol | GenBank ID | Entrez Gene ID | UniGene ID |
|---|---|---|---|---|
| 1073. cytoskeleton associated protein 2-like | CKAP2L | NM_152515.2 | 150468 | Hs.434250 |
| 1074. CDC28 protein kinase regulatory subunit 2 | CKS2 | NM_001827.1 | 1164 | Hs.83758 |
| 1075. claspin homolog (*Xenopus laevis*) | CLSPN | NM_022111.2 | 63967 | Hs.175613 |
| 1076. CSAG family, member 2 | CSAG2 | NM_004909.1 | 9598 | Hs.522810 |
| 1077. cancer/testis antigen 1A | CTAG1A | NM_139250.1 | 246100 | Hs.559536 |
| 1078. cancer/testis antigen 1B | CTAG1B | NM_001327.1 | 1485 | Hs.534310 |
| 1079. cancer/testis antigen 2 | CTAG2 | NM_020994.2 | 30848 | Hs.87225 |
| 1080. cystathionase (cystathionine gamma-lyase) | CTH | NM_001902.4 | 1491 | Hs.19904 |
| 1081. cathepsin L-like 3 | CTSLL3 | L25629.1 | 1518 | Hs.418123 |
| 1082. cortactin | CTTN | NM_005231 | 2017 | Hs.301348 |
| 1083. DBF4 homolog (*S. cerevisiae*) | DBF4 | NM_006716.3 | 10926 | Hs.208414 |
| 1084. development and differentiation enhancing factor 1 | DDEF1 | NM_018482.2 | 50807 | Hs.106015 |
| 1085. DEAD (Asp-Glu-Ala-Asp) box polypeptide 18 | DDX18 | NM_006773.3 | 8886 | Hs.363492 |
| 1086. DEP domain containing 1 | DEPDC1 | NM_017779.3 | 55635 | Hs.445098 |
| 1087. dihydrofolate reductase | DHFR | NM_000791.3 | 1719 | Hs.464813 |
| 1088. hypothetical protein DKFZp762E1312 | DKFZp762E1312 | NM_018410.3 | 55355 | Hs.532968 |
| 1089. DnaJ (Hsp40) homolog, subfamily C, member 10 | DNAJC10 | NM_018981.1 | 54431 | Hs.516632 |
| 1090. dpy-19-like 1 (*C. elegans*) | DPY19L1 | AJ011911.1 | 23333 | Hs.510645 |
| 1091. denticleless homolog (*Drosophila*) | DTL | NM_016448.1 | 51514 | Hs.126774 |
| 1092. deltex 3 homolog (*Drosophila*) | DTX3 | NM_178502.2 | 196403 | Hs.32374 |
| 1093. dual specificity phosphatase 4 | DUSP4 | NM_001394.5 | 1846 | Hs.417962 |
| 1094. dual specificity phosphatase 6 | DUSP6 | NM_001946.2 | 1848 | Hs.298654 |
| 1095. endothelin 3 | EDN3 | NM_207032.1 | 1908 | Hs.1408 |
| 1096. engrailed homolog 2 | EN2 | NM_001427.2 | 2020 | Hs.134989 |
| 1097. ets variant gene 1 | ETV1 | NM_004956.3 | 2115 | Hs.22634 |
| 1098. exonuclease 1 | EXO1 | NM_130398.2 | 9156 | Hs.498248 |
| 1099. exosome component 3 | EXOSC3 | NM_016042.2 | 51010 | Hs.493887 |
| 1100. eyes absent homolog 4 (*Drosophila*) | EYA4 | NM_004100 | 2070 | Hs.102408 |
| 1101. family with sequence similarity 126, member A | FAM126A | NM_032581.2 | 84668 | Hs.85603 |
| 1102. family with sequence similarity 29, member A | FAM29A | NM_017645.3 | 54801 | Hs.533468 |
| 1103. family with sequence similarity 62 (C2 domain containing) member B | FAM62B | NM_020728.1 | 57488 | Hs.490795 |
| 1104. F-box only protein 32 | FBXO32 | NM_058229 | 114907 | Hs.403933 |
| 1105. FK506 binding protein 10, 65 kDa | FKBP10 | NM_021939.2 | 60681 | Hs.463035 |
| 1106. hypothetical protein FLJ10781 | FLJ10781 | NM_018215.2 | 55228 | Hs.8395 |
| 1107. hypothetical protein FLJ11029 | FLJ11029 | NM_018304 | 55771 | Hs.274448 |
| 1108. hypothetical protein FLJ13236 | FLJ13236 | NM_024902 | 79962 | Hs.170298 |
| 1109. FLJ20105 protein | FLJ20105 | NM_001009954.1 | 54821 | Hs.47558 |
| 1110. hypothetical protein FLJ30655 | FLJ30655 | NM_144643 | 132320 | Hs.404000 |
| 1111. hypothetical protein FLJ30707 | FLJ30707 | NM_145019 | 220108 | Hs.292590 |
| 1112. FLJ36874 protein | FLJ36874 | NM_152716.1 | 219988 | Hs.523698 |
| 1113. fibronectin type III domain containing 3B | FNDC3B | NM_022763.2 | 64778 | Hs.159430 |
| 1114. FERM domain containing 5 | FRMD5 | NM_032892.3 | 84978 | Hs.368399 |
| 1115. FSH primary response (LRPR1 homolog, rat) 1 | FSHPRH1 | NM_006733 | 2491 | Hs.318398 |
| 1116. GA binding protein transcription factor, beta subunit 2 | GABPB2 | NM_005254.4 | 2553 | Hs.511316 |
| 1117. G antigen 4 | GAGE4 | NM_001474.1 | 2576 | Hs.460641 |
| 1118. G antigen 8 | GAGE8 | NM_012196.1 | 26749 | Hs.278606 |
| 1119. UDP-N-acetyl-alpha-D-galactosamine:polypeptide N-acetylgalactosaminyltransferase 7 (GalNAc-T7) | GALNT7 | NM_017423.1 | 51809 | Hs.127407 |
| 1120. ganglioside-induced differentiation-associated protein 1 | GDAP1 | NM_018972 | 54332 | Hs.168950 |
| 1121. growth differentiation factor 15 | GDF15 | NM_004864.1 | 9518 | Hs.515258 |
| 1122. glutaminase | GLS | NM_014905.2 | 2744 | Hs.116448 |
| 1123. glutamate dehydrogenase 2 | GLUD2 | BC005111.1 | 2747 | Hs.368538 |
| 1124. golgi transport 1 homolog B (*S. cerevisiae*) | GOLT1B | NM_016072.2 | 51026 | Hs.62275 |
| 1125. G patch domain containing 2 | GPATC2 | NM_018040.1 | 55105 | Hs.420757 |
| 1126. glycerol-3-phosphate dehydrogenase 2 (mitochondrial) | GPD2 | NM_000408.2 | 2820 | Hs.148266 |
| 1127. G protein-coupled receptor 107 | GPR107 | NM_020960.3 | 57720 | Hs.512461 |
| 1128. G protein-coupled receptor 19 | GPR19 | NM_006143.1 | 2842 | Hs.92458 |

TABLE B-continued

Genes differentially expressed in metastatic melanoma. Expression of the genes listed in this table is increased relative to non-metastatic samples.

| Gene description | Gene Symbol | GenBank ID | Entrez Gene ID | UniGene ID |
|---|---|---|---|---|
| 1129. general transcription factor IIH, polypeptide 2, 44 kDa | GTF2H2 | NM_001515.2 | 2966 | Hs.191356 |
| 1130. general transcription factor IIH, polypeptide 4, 52 kDa | GTF2H4 | NM_001517.4 | 2968 | Hs.485070 |
| 1131. G-2 and S-phase expressed 1 | GTSE1 | NM_016426.4 | 51512 | Hs.386189 |
| 1132. H2A histone family, member V | H2AFV | NM_201436.1 | 94239 | Hs.157379 |
| 1133. hairy/enhancer-of-split related with YRPW motif 1 | HEY1 | NM_012258 | 23462 | Hs.234434 |
| 1134. 3-hydroxyisobutyrate dehydrogenase | HIBADH | NM_152740.2 | 11112 | Hs.406758 |
| 1135. histone linker H1 domain, spermatid-specific 1 | HILS1 | NM_194072.1 | 373861 | Hs.25934 |
| 1136. histone 1, H2bh | HIST1H2BH | NM_003524.2 | 8345 | Hs.247815 |
| 1137. histone 1, H3d | HIST1H3D | NM_003530 | 8351 | Hs.532144 |
| 1138. hyaluronan-mediated motility receptor (RHAMM) | HMMR | NM_012484.1 | 3161 | Hs.72550 |
| 1139. HN1 like | HN1L | NM_144570 | 90861 | Hs.437433 |
| 1140. heterogeneous nuclear ribonucleoprotein C (C1/C2) | HNRPC | NM_004500 | 3183 | Hs.356139 |
| 1141. homeo box A10 | HOXA10 | NM_018951.3 | 3206 | Hs.110637 |
| 1142. homeo box B6 | HOXB6 | NM_018952 | 3216 | Hs.98428 |
| 1143. homeo box B7 | HOXB7 | NM_004502.3 | 3217 | Hs.436181 |
| 1144. homeo box B9 | HOXB9 | NM_024017 | 3219 | Hs.321142 |
| 1145. homeo box D13 | HOXD13 | NM_000523.2 | 3239 | Hs.152414 |
| 1146. heat shock 90 kDa protein 1, alpha-like 3 | HSPCAL3 | NM_001040141.1 | 3324 | Hs.523560 |
| 1147. heat shock 90 kDa protein 1, beta | HSPCB | NM_007355.2 | 3326 | Hs.509736 |
| 1148. heat shock 60 kDa protein 1 (chaperonin) | HSPD1 | NM_002156.4 | 3329 | Hs.113684 |
| 1149. heat shock 10 kDa protein 1 (chaperonin 10) | HSPE1 | NM_002157.1 | 3336 | Hs.558338 |
| 1150. heat shock 105 kDa/110 kDa protein 1 | HSPH1 | NM_006644.2 | 10808 | Hs.36927 |
| 1151. insulin-like growth factor 2 mRNA binding protein 3 | IGF2BP3 | NM_006547 | 10643 | Hs.432616 |
| 1152. interleukin 1 receptor accessory protein | IL1RAP | NM_002182.2 | 3556 | Hs.478673 |
| 1153. potassium voltage-gated channel, KQT-like subfamily, member 5 | KCNQ5 | NM_019842.2 | 56479 | Hs.98129 |
| 1154. KIAA0101 | KIAA0101 | NM_014736.4 | 9768 | Hs.81892 |
| 1155. KIAA0470 | KIAA0470 | AK001664.1 | 9859 | Hs.408293 |
| 1156. KIAA1618 | KIAA1618 | NM_020954.2 | 57714 | Hs.514554 |
| 1157. KIAA1917 protein | KIAA1917 | BF056204 | 114804 | Hs.434389 |
| 1158. kinesin family member 18A | KIF18A | NM_031217.2 | 81930 | Hs.301052 |
| 1159. kinesin family member 4A | KIF4A | NM_012310.2 | 24137 | Hs.279766 |
| 1160. kinesin family member C1 | KIFC1 | NM_002263.2 | 3833 | Hs.436912 |
| 1161. karyopherin alpha 2 (RAG cohort 1, importin alpha 1) | KPNA2 | NM_002266.2 | 3838 | Hs.159557 |
| 1162. lactamase, beta 2 | LACTB2 | NM_016027.1 | 51110 | Hs.118554 |
| 1163. hypothetical protein LOC144874 | LOC144874 | AL832853.1 | 144874 | Hs.439363 |
| 1164. hypothetical protein LOC150946 | LOC150946 | AV751887 | 150946 | Hs.187912 |
| 1165. hypothetical protein LOC152485 | LOC152485 | NM_178835.2 | 152485 | Hs.133916 |
| 1166. LOC346615 | LOC346615 | XM_934971.1 | 645591 | Hs.453810 |
| 1167. LOC346616 | LOC346616 | BC012751.2 | 645591 | Hs.285410 |
| 1168. LOC346658 | LOC346658 | AI143641 | 346658 | Hs.181400 |
| 1169. LOC346888 | LOC346888 | XM_294450.5 | 346887 | Hs.127286 |
| 1170. hypothetical gene LOC401431 | LOC401431 | NM_001008745.1 | 401431 | Hs.556097 |
| 1171. hypothetical gene supported by BC034933; BC068085 | LOC440995 | BC068085.1 | 440995 | Hs.552645 |
| 1172. PTD016 protein | LOC51136 | NM_016125 | 51136 | Hs.531701 |
| 1173. melanoma antigen | LOC51152 | XM_927576.1 | 644433 | Hs.132526 |
| 1174. hypothetical protein DKFZp434D2328 | LOC91526 | NM_153697 | 91526 | Hs.11571 |
| 1175. hypothetical protein LOC92249 | LOC92249 | AK001756.1 | 92249 | Hs.31532 |
| 1176. peroxisomal lon protease 2 | LONP2 | NM_031490.2 | 83752 | Hs.555994 |
| 1177. leucine zipper protein 5 | LUZP5 | AK092008.1 | 54892 | Hs.18616 |
| 1178. mannose-6-phosphate receptor (cation dependent) | M6PR | NM_002355.2 | 4074 | Hs.134084 |
| 1179. MAD2 mitotic arrest deficient-like 1 (yeast) | MAD2L1 | NM_002358.2 | 4085 | Hs.28312 |
| 1180. melanoma antigen family A, 1 (directs expression of antigen MZ2-E) | MAGEA1 | NM_004988.3 | 4100 | Hs.72879 |
| 1181. melanoma antigen family A, 12 | MAGEA12 | NM_005367.4 | 4111 | Hs.169246 |
| 1182. melanoma antigen family A, 2B | MAGEA2B | NM_153488.3 | 266740 | Hs.534597 |
| 1183. melanoma antigen family A, 3 | MAGEA3 | NM_005362.3 | 4102 | Hs.417816 |
| 1184. melanoma antigen family A, 5 | MAGEA5 | NM_021049.3 | 4104 | Hs.546265 |
| 1185. melanoma antigen family A, 6 | MAGEA6 | NM_005363.2 | 4105 | Hs.441113 |
| 1186. mannosidase, endo-alpha-like | MANEAL | NM_152496.1 | 149175 | Hs.534562 |

TABLE B-continued

Genes differentially expressed in metastatic melanoma. Expression of the genes listed in this table is increased relative to non-metastatic samples.

| Gene description | Gene Symbol | GenBank ID | Entrez Gene ID | UniGene ID |
|---|---|---|---|---|
| 1187. microtubule-associated protein 9 | MAP9 | NM_001039580.1 | 79884 | Hs.549331 |
| 1188. MARCKS-like 1 | MARCKSL1 | NM_023009.4 | 65108 | Hs.75061 |
| 1189. MCM10 minichromosome maintenance deficient 10 (*S. cerevisiae*) | MCM10 | NM_018518.3 | 55388 | Hs.198363 |
| 1190. MCM8 minichromosome maintenance deficient (*S. cerevisiae*) | MCM8 | NM_032485.4 | 84515 | Hs.437582 |
| 1191. mucolipin 2 | MCOLN2 | NM_153259.2 | 255231 | Hs.459526 |
| 1192. malic enzyme 2, NAD(+)-dependent, mitochondrial | ME2 | NM_002396.3 | 4200 | Hs.233119 |
| 1193. methyltransferase like 2 | METTL2 | NM_018396.2 | 55798 | Hs.433213 |
| 1194. milk fat globule-EGF factor 8 protein | MFGE8 | NM_005928.1 | 4240 | Hs.3745 |
| 1195. hypothetical protein MGC11082 | MGC11082 | NM_032691 | 84777 | Hs.326729 |
| 1196. hypothetical protein MGC5509 | MGC5509 | NM_024093 | 79074 | Hs.409606 |
| 1197. muskelin 1, intracellular mediator containing kelch motifs | MKLN1 | NM_013255 | 4289 | Hs.145599 |
| 1198. matrix metallopeptidase 12 (macrophage elastase) | MMP12 | NM_002426.2 | 4321 | Hs.1695 |
| 1199. matrix metallopeptidase 14 (membrane-inserted) | MMP14 | NM_004995.2 | 4323 | Hs.2399 |
| 1200. matrix metallopeptidase 8 (neutrophil collagenase) | MMP8 | NM_002424.1 | 4317 | Hs.161839 |
| 1201. meiotic nuclear divisions 1 homolog (*S. cerevisiae*) | MND1 | NM_032117.2 | 84057 | Hs.294088 |
| 1202. M-phase phosphoprotein 9 | MPHOSPH9 | NM_022782 | 10198 | Hs.445084 |
| 1203. metallophosphoesterase domain containing 2 | MPPED2 | NM_001584.1 | 744 | Hs.289795 |
| 1204. myosin regulatory light chain MRCL3 | MRCL3 | NM_006471 | 10627 | Hs.233936 |
| 1205. mitochondrial ribosomal protein L44 | MRPL44 | NM_022915.2 | 65080 | Hs.203559 |
| 1206. musashi homolog 2 (*Drosophila*) | MSI2 | NM_138962.2 | 124540 | Hs.134470 |
| 1207. methylene tetrahydrofolate dehydrogenase (NAD+ dependent), methenyltetrahydrofolate cyclohydrolase | MTHFD2 | NM_006636 | 10797 | Hs.154672 |
| 1208. mitochondrial translational release factor 1 | MTRF1 | NM_004294.2 | 9617 | Hs.382176 |
| 1209. multiple substrate lipid kinase | MULK | BC009775.1 | 55750 | Hs.521240 |
| 1210. nuclear cap binding protein subunit 1, 80 kDa | NCBP1 | NM_002486 | 4686 | Hs.439203 |
| 1211. nuclear cap binding protein subunit 2, 20 kDa | NCBP2 | NM_007362 | 22916 | Hs.240770 |
| 1212. neural precursor cell expressed, developmentally down-regulated 4-like | NEDD4L | NM_015277.2 | 23327 | Hs.185677 |
| 1213. NIMA (never in mitosis gene a)-related kinase 2 | NEK2 | NM_002497.2 | 4751 | Hs.153704 |
| 1214. nicotinamide nucleotide transhydrogenase | NNT | NM_012343.2 | 23530 | Hs.482043 |
| 1215. neuropilin 2 | NRP2 | NM_003872 | 8828 | Hs.471200 |
| 1216. 5',3'-nucleotidase, cytosolic | NT5C | NM_014595 | 30833 | Hs.67201 |
| 1217. NudC domain containing 1 | NUDCD1 | NM_032869.2 | 84955 | Hs.558577 |
| 1218. nudix (nucleoside diphosphate linked moiety X)-type motif 4 | NUDT4 | NM_019094 | 11163 | Hs.506325 |
| 1219. outer dense fiber of sperm tails 2 | ODF2 | NM_153437.1 | 4957 | Hs.129055 |
| 1220. procollagen-proline, 2-oxoglutarate 4-dioxygenase (proline 4-hydroxylase), alpha polypeptide I | P4HA1 | NM_000917.2 | 5033 | Hs.500047 |
| 1221. poly(A) binding protein, cytoplasmic 4 (inducible form) | PABPC4 | NM_003819.2 | 8761 | Hs.169900 |
| 1222. P antigen family, member 1 (prostate associated) | PAGE1 | NM_003785.3 | 8712 | Hs.128231 |
| 1223. PDZ binding kinase | PBK | NM_018492.2 | 55872 | Hs.104741 |
| 1224. PDGFA associated protein 1 | PDAP1 | NM_014891.5 | 11333 | Hs.278426 |
| 1225. phosphodiesterase 4B, cAMP-specific (phosphodiesterase E4 dunce homolog, *Drosophila*) | PDE4B | NM_001037339.1 | 5142 | Hs.198072 |
| 1226. protein disulfide isomerase family A, member 6 | PDIA6 | NM_005742.2 | 10130 | Hs.212102 |
| 1227. paternally expressed 10 | PEG10 | NM_015068.3 | 23089 | Hs.147492 |
| 1228. peroxisome biogenesis factor 13 | PEX13 | NM_002618.2 | 5194 | Hs.368348 |
| 1229. prefoldin 2 | PFDN2 | NM_012394.3 | 5202 | Hs.492516 |
| 1230. phosphofructokinase, muscle | PFKM | NM_000289.3 | 5213 | Hs.75160 |
| 1231. profilin 2 | PFN2 | NM_002628.4 | 5217 | Hs.91747 |
| 1232. prohibitin | PHB | NM_002634.2 | 5245 | Hs.514303 |

TABLE B-continued

Genes differentially expressed in metastatic melanoma. Expression
of the genes listed in this table is increased relative to non-metastatic samples.

| Gene description | Gene Symbol | GenBank ID | Entrez Gene ID | UniGene ID |
|---|---|---|---|---|
| 1233. pleckstrin homology-like domain, family A, member 1 | PHLDA1 | AK074510.1 | 652993 | Hs.82101 |
| 1234. proteolipid protein 1 (Pelizaeus-Merzbacher disease, spastic paraplegia 2, uncomplicated) | PLP1 | NM_000533.3 | 5354 | Hs.1787 |
| 1235. phospholipid scramblase 1 | PLSCR1 | NM_021105.1 | 5359 | Hs.130759 |
| 1236. plexin B3 | PLXNB3 | NM_005393.1 | 5365 | Hs.380742 |
| 1237. partner of NOB1 homolog (*S. cerevisiae*) | PNO1 | NM_020143.2 | 56902 | Hs.262858 |
| 1238. polymerase (RNA) I polypeptide B, 128 kDa | POLR1B | NM_019014.3 | 84172 | Hs.86337 |
| 1239. polymerase (RNA) III (DNA directed) polypeptide K, 12.3 kDa | POLR3K | NM_016310.2 | 51728 | Hs.437186 |
| 1240. popeye domain containing 3 | POPDC3 | NM_022361.3 | 64208 | Hs.458336 |
| 1241. POU domain, class 3, transcription factor 2 | POU3F2 | NM_005604.2 | 5454 | Hs.182505 |
| 1242. PTPRF interacting protein, binding protein 1 (liprin beta 1) | PPFIBP1 | NM_003622 | 8496 | Hs.172445 |
| 1243. PR domain containing 13 | PRDM13 | NM_021620.2 | 59336 | Hs.287386 |
| 1244. prolyl endopeptidase-like | PREPL | AB007896.1 | 9581 | Hs.112916 |
| 1245. protein kinase, cAMP-dependent, regulatory, type I, alpha (tissue specific extinguisher 1) | PRKAR1A | NM_002734.3 | 5573 | Hs.280342 |
| 1246. phosphoribosyl pyrophosphate synthetase 1 | PRPS1 | NM_002764.2 | 5631 | Hs.56 |
| 1247. proline/serine-rich coiled-coil 1 | PSRC1 | NM_001005290.2 | 84722 | Hs.405925 |
| 1248. PTK2 protein tyrosine kinase 2 | PTK2 | NM_005607 | 5747 | Hs.395482 |
| 1249. protein tyrosine phosphatase-like A domain containing 1 | PTPLAD1 | NM_016395.1 | 51495 | Hs.512973 |
| 1250. RAD54 homolog B (*S. cerevisiae*) | RAD54B | NM_012415.2 | 25788 | Hs.30561 |
| 1251. RAD54-like (*S. cerevisiae*) | RAD54L | NM_003579.2 | 8438 | Hs.523220 |
| 1252. Ras protein-specific guanine nucleotide-releasing factor 1 | RASGRF1 | NM_002891 | 5923 | Hs.459035 |
| 1253. regulator of G-protein signalling 1 | RGS1 | NM_002922.3 | 5996 | Hs.75256 |
| 1254. regulator of G-protein signalling 20 | RGS20 | NM_003702 | 8601 | Hs.368733 |
| 1255. Ras homolog enriched in brain | RHEB | NM_005614 | 6009 | Hs.283521 |
| 1256. Rho-related BTB domain containing 2 | RHOBTB2 | NM_015178.1 | 23221 | Hs.372688 |
| 1257. ras homolog gene family, member Q | RHOQ | NM_012249.2 | 23433 | Hs.549125 |
| 1258. ribulose-5-phosphate-3-epimerase | RPE | NM_199229.1 | 6120 | Hs.282260 |
| 1259. Ras-related GTP binding D | RRAGD | NM_021244.2 | 58528 | Hs.485938 |
| 1260. ribonucleotide reductase M2 polypeptide | RRM2 | NM_001034 | 6241 | Hs.226390 |
| 1261. RRN3 RNA polymerase I transcription factor homolog (yeast) | RRN3 | NM_018427.3 | 54700 | Hs.460078 |
| 1262. RNA terminal phosphate cyclase domain 1 | RTCD1 | NM_003729.1 | 8634 | Hs.484222 |
| 1263. sin3-associated polypeptide, 30 kDa | SAP30 | NM_003864 | 8819 | Hs.413835 |
| 1264. src family associated phosphoprotein 2 | SCAP2 | NM_003930.3 | 8935 | Hs.200770 |
| 1265. SEC22 vesicle trafficking protein-like 3 (*S. cerevisiae*) | SEC22L3 | NM_032970.2 | 9117 | Hs.445892 |
| 1266. SEC24 related gene family, member A (*S. cerevisiae*) | SEC24A | AJ131244 | 10802 | Hs.211612 |
| 1267. septin 2 | SEPT2 | NM_001008491.1 | 4735 | Hs.335057 |
| 1268. septin 9 | SEPT9 | NM_006640 | 10801 | Hs.288094 |
| 1269. stress-associated endoplasmic reticulum protein 1 | SERP1 | NM_014445 | 27230 | Hs.518326 |
| 1270. serine (or cysteine) proteinase inhibitor, clade E (nexin, plasminogen activator inhibitor type 1), member 2 | SERPINE2 | NM_006216 | 5270 | Hs.21858 |
| 1271. seizure related 6 homolog (mouse)-like 2 | SEZ6L2 | NM_012410.1 | 26470 | Hs.6314 |
| 1272. sarcoglycan, epsilon | SGCE | NM_003919.1 | 8910 | Hs.371199 |
| 1273. solute carrier family 16 (monocarboxylic acid transporters), member 4 | SLC16A4 (SL16AJ) | NM_004696.1 | 9122 | Hs.351306 |
| 1274. solute carrier family 2 (facilitated glucose transporter), member 3 | SLC2A3 | NM_006931.1 | 6515 | Hs.419240 |
| 1275. solute carrier family 43, member 3 | SLC43A3 | NM_014096.2 | 29015 | Hs.99962 |
| 1276. SMC4 structural maintenance of chromosomes 4-like 1 (yeast) | SMC4L1 | NM_001002799.1 | 10051 | Hs.58992 |
| 1277. sorting nexin 25 | SNX25 | NM_031953.2 | 83891 | Hs.369091 |
| 1278. SRY (sex determining region Y)-box 5 | SOX5 | NM_006940 | 6660 | Hs.434948 |
| 1279. secreted phosphoprotein 1 (osteopontin, bone sialoprotein I, early T-lymphocyte activation 1) | SPP1 | NM_000582 | 6696 | Hs.313 |

TABLE B-continued

Genes differentially expressed in metastatic melanoma. Expression of the genes listed in this table is increased relative to non-metastatic samples.

| Gene description | Gene Symbol | GenBank ID | Entrez Gene ID | UniGene ID |
|---|---|---|---|---|
| 1280. sprouty-related, EVH1 domain containing 1 | SPRED1 | NM_152594.1 | 161742 | Hs.525781 |
| 1281. sprouty-related, EVH1 domain containing 2 | SPRED2 | NM_181784.1 | 200734 | Hs.59332 |
| 1282. sprouty homolog 2 (*Drosophila*) | SPRY2 | NM_005842.2 | 10253 | Hs.18676 |
| 1283. signal sequence receptor, alpha (translocon-associated protein alpha) | SSR1 | NM_003144.2 | 6745 | Hs.114033 |
| 1284. ST6 (alpha-N-acetyl-neuraminyl-2,3-beta-galactosyl-1,3)-N-acetylgalactosaminide alpha-2,6-sialyltransferase 3 | ST6GALNAC3 | NM_152996.1 | 256435 | Hs.337040 |
| 1285. stress 70 protein chaperone, microsome-associated, 60 KDa | STCH | NM_006948.4 | 6782 | Hs.352341 |
| 1286. serine/threonine kinase 6 | STK6 | NM_198433.1 | 6790 | Hs.250822 |
| 1287. TATA box binding protein (TBP)-associated factor, RNA polymerase I, A, 48 kDa | TAF1A | NM_005681.2 | 9015 | Hs.153088 |
| 1288. transcription factor 20 (AR1) | TCF20 | NM_181492.1 | 6942 | Hs.475018 |
| 1289. transferrin receptor (p90, CD71) | TFRC | NM_003234.1 | 7037 | Hs.529618 |
| 1290. TGFB-induced factor (TALE family homeobox) | TGIF | NM_170695.2 | 7050 | Hs.373550 |
| 1291. transketolase-like 1 | TKTL1 | NM_012253.2 | 8277 | Hs.102866 |
| 1292. transmembrane protein 38B | TMEM38B | NM_018112.1 | 55151 | Hs.411925 |
| 1293. transmembrane protein 4 | TMEM4 | NM_014255 | 10330 | Hs.8752 |
| 1294. transmembrane protein 48 | TMEM48 | NM_018087.3 | 55706 | Hs.476525 |
| 1295. transmembrane protein 64 | TMEM64 | NM_001008495.1 | 169200 | Hs.556805 |
| 1296. TRAF2 and NCK interacting kinase | TNIK | NM_015028.1 | 23043 | Hs.34024 |
| 1297. trinucleotide repeat containing 15 | TNRC15 | NM_015575 | 26058 | Hs.334871 |
| 1298. torsin A interacting protein 1 | TOR1AIP1 | NM_015602.2 | 26092 | Hs.496459 |
| 1299. TP53TG3 protein | TP53TG3 | NM_016212.2 | 24150 | Hs.513537 |
| 1300. TPX2, microtubule-associated, homolog (*Xenopus laevis*) | TPX2 | NM_012112.4 | 22974 | Hs.244580 |
| 1301. translocation associated membrane protein 1 | TRAM1 | NM_014294.3 | 23471 | Hs.491988 |
| 1302. tribbles homolog 2 (*Drosophila*) | TRIB2 | NM_021643.1 | 28951 | Hs.467751 |
| 1303. tripartite motif-containing 51 | TRIM51 | NM_032681.1 | 84767 | Hs.326734 |
| 1304. trophinin associated protein (tastin) | TROAP | NM_005480.2 | 10024 | Hs.524399 |
| 1305. translin | TSN | NM_004622.2 | 7247 | Hs.75066 |
| 1306. tetratricopeptide repeat domain 26 | TTC26 | NM_024926.1 | 79989 | Hs.303930 |
| 1307. thymidylate synthetase | TYMS | NM_001071.1 | 7298 | Hs.369762 |
| 1308. ubiquitin-conjugating enzyme E2C | UBE2C | NM_181800.1 | 11065 | Hs.93002 |
| 1309. ubiquitin-conjugating enzyme E2I (UBC9 homolog, yeast) | UBE2I | NM_003345 | 7329 | Hs.302903 |
| 1310. ubiquitin-conjugating enzyme E2T (putative) | UBE2T | NM_014176.1 | 29089 | Hs.5199 |
| 1311. ubiquitin family domain containing 1 | UBFD1 | NM_019116 | 56061 | Hs.3459 |
| 1312. UDP glycosyltransferase 8 (UDP-galactose ceramide galactosyltransferase) | UGT8 | NM_003360.2 | 7368 | Hs.144197 |
| 1313. X antigen family, member 1 | XAGE1 | NM_020411.1 | 9503 | Hs.112208 |
| 1314. X antigen family, member 2 | XAGE2 | NM_130777.1 | 9502 | Hs.522654 |
| 1315. zinc finger protein 697 | ZNF697 | XM_371286.4 | 90874 | Hs.381105 |
| 1316. hypothetical protein LOC650446 | LOC650446 | XM_939537 | 650446 | Hs.380331 |
| 1317. musashi homolog 2 (*Drosophila*) | MSI2 | NM_138962 | 124540 | Hs.185084 |
| 1318. neuropilin 2 | NRP2 | NM_003872 | 8828 | Hs.471200 |
| 1319. hypothetical gene supported by AF086409 | — | BF516262 | 144705 | Hs.44817 |
| 1320. glutamate dehydrogenase 2 | GLUD2 | AA909218 | — | Hs.430334 |
| 1321. hypothetical protein LOC647291 | LOC647291 | NM_001039795.1 | 647291 | — |
| 1322. hypothetical gene supported by AL832403; BC019824 | — | AI631833 | 347884 | Hs.374451 |
| 1323. Gene supported by sequence info. | — | H38635 | — | Hs.391401 |
| 1324. Gene supported by sequence info. | — | BG285837 | — | Hs.444096 |
| 1325. Gene supported by sequence info. | — | AW270845 | — | — |
| 1326. Gene supported by sequence info. | — | AI810266 | — | Hs.130853 |
| 1327. Gene supported by sequence info. | — | AI911318 | — | Hs.224153 |
| 1328. Gene supported by sequence info. | — | AI003508 | — | Hs.117689 |
| 1329. Gene supported by sequence info. | — | AI554075 | — | Hs.120204 |
| 1330. Gene supported by sequence info. | — | CA424969 | — | Hs.146268 |
| 1331. Gene supported by sequence info. | — | AW665538 | — | Hs.479714 |
| 1332. Gene supported by sequence info. | — | BF224436 | — | Hs.123294 |
| 1333. Gene supported by sequence info. | — | AK024236 | — | Hs.476469 |
| 1334. Gene supported by sequence info. | — | BE891646 | — | Hs.281434 |

TABLE B-continued

Genes differentially expressed in metastatic melanoma. Expression of the genes listed in this table is increased relative to non-metastatic samples.

| Gene description | Gene Symbol | GenBank ID | Entrez Gene ID | UniGene ID |
|---|---|---|---|---|
| 1335. Gene supported by sequence info. | — | AI936197 | — | Hs.360386 |
| 1336. Gene supported by sequence info. | — | AI374756 | — | Hs.116453 |
| 1337. Gene supported by sequence info. | — | AI861893 | — | Hs.129967 |
| 1338. Gene supported by sequence info. | — | BC026261 | — | Hs.364642 |

TABLE C

Genes differentially expressed in metastatic melanoma. Expression of the genes listed in this table is decreased relative to non-metastatic samples.

| Gene description | Gene Symbol | GenBank ID | Entrez Gene ID |
|---|---|---|---|
| gap junction protein, beta 6 (connexin 30) | GJB6 | NM_006783.2 | 10804 |
| small proline-rich protein 1A | SPRR1A | NM_005987.2 | 6698 |
| serpin peptidase inhibitor, clade B (ovalbumin), member 5 | SERPINB5 | NM_002639.2 | 5268 |
| calmodulin-like 5 | CALML5 (CLSP) | NM_017422.3 | 51806 |
| desmocollin 1 | DSC1 | NM_024421.1 | 1823 |
| plakophilin 1 (ectodermal dysplasia/skin fragility syndrome) | PKP1 | NM_001005337.1 | 5317 |
| chloride channel, calcium activated, family member 2 | CLCA2 | NM_006536.4 | 9635 |
| desmoglein 1 | DSG1 | NM_001942.1 | 1828 |
| corneodesmosin | CDSN | L20815.1 | 1041 |
| lymphocyte antigen 6 complex, locus D | LY6D | NM_003695.2 | 8581 |
| late cornified envelope 2B | LCE2B | NM_014357.3 | 26239 |
| filaggrin | FLG | NM_002016.1 | 2312 |
| filaggrin 2 | RP1-14N1.3 | NM_001014342.1 | 388698 |
| keratin 16 (focal non-epidermolytic palmoplantar keratoderma) | KRT16 | NM_005557.2 | 3868 |
| suprabasin | SBSN | NM_198538.11 | 374897 |
| serpin peptidase inhibitor, clade B (ovalbumin), member 3 | SERPINB3 | NM_006919.1 | 6317 |
| serpin peptidase inhibitor, clade B (ovalbumin), member 7 | SERPINB7 | NM_001040147.1 | 8710 |
| keratin 17 | KRT17 | NM_000422.1 | 3872 |
| kallikrein 7 (chymotryptic, stratum corneum) | KLK7 | NM_005046.2 | 5650 |
| loricrin | LOR | BC108290.1 | 4014 |
| secreted LY6/PLAUR domain containing 1 | SLURP1 | NM_020427.2 | 57152 |
| hepatocellular carcinoma antigen gene 520 | LOC63928 | NM_022097.1 | 63928 |
| keratin 15 | KRT15 | NM_002275.2 | 3866 |
| lectin, galactoside-binding, soluble, 7 (galectin 7) | LGALS7 | NM_002307.1 | 3963 |
| cystatin E/M | CST6 | NM_001323.2 | 1474 |
| small proline-rich protein 1B (cornifin) | SPRR1B | NM_003125.2 | 6699 |
| cornifelin | CNFN | NM_032488.2 | 84518 |
| tripartite motif-containing 29 | TRIM29 | NM_058193.1 | 23650 |
| epiplakin 1 | EPPK1 | AL137725.1 | 83481 |
| stratifin | SFN | NM_006142.3 | 2810 |
| keratin 6B | KRT6B | NM_005555.2 | 3854 |
| desmoglein 3 (pemphigus vulgaris antigen) | DSG3 | BX538327.1 | 1830 |
| small proline-rich protein 2B | SPRR2B | NM_001017418.1 | 6701 |
| dermokine | DMKN | NM_033317.2 | 93099 |
| N-acylsphingosine amidohydrolase (alkaline ceramidase) 3 | ASAH3 | NM_133492 | 125981 |
| serpin peptidase inhibitor, clade B (ovalbumin), member 13 | SERPINB13 | NM_012397.2 | 5275 |
| kallikrein 11 | KLK11 | NM_006853.2 | 11012 |
| arylacetamide deacetylase-like 2 | AADACL2 | NM_207365.1 | 344752 |
| death associated protein-like 1 | DAPL1 | NM_001017920.1 | 92196 |
| ATP-binding cassette, sub-family A (ABC1), member 12 | ABCA12 | NM_173076.2 | 26154 |
| desmocollin 3 | DSC3 | NM_001941.2 | 1825 |
| premature ovarian failure, 1B | POF1B | NM_024921.2 | 79983 |
| GATA binding protein 3 | GATA3 | NM_001002295.1 | 2625 |
| LY6/PLAUR domain containing 3 | LYPD3 | NM_014400.2 | 27076 |
| keratin 6A | KRT6A | AL569511 | 140446 |

TABLE C-continued

Genes differentially expressed in metastatic melanoma. Expression
of the genes listed in this table is decreased relative to non-metastatic samples.

| Gene description | Gene Symbol | GenBank ID | Entrez Gene ID |
| --- | --- | --- | --- |
| Ets homologous factor | EHF | AI763378 | 26298 |
| protocadherin 21 | PCDH21 | NM_033100.1 | 92211 |
| Cas-Br-M (murine) ecotropic retroviral transforming sequence c | CBLC | NM_012116.2 | 23624 |
| fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | FGFR2 | NM_022969.1 | 2263 |
| sciellin | SCEL | NM_144777.1 | 8796 |
| fibroblast growth factor receptor 3 (achondroplasia, thanatophoric dwarfism) | FGFR3 | NM_000142.2 | 2261 |

TABLE D

Genes differentially expressed in metastatic melanoma. Expression
of the genes listed in this table is increased relative to non-metastatic samples.

| Gene description | Gene Symbol | GenBank reference ID | Entrez Gene ID |
| --- | --- | --- | --- |
| melanoma antigen family A, 3 | MAGEA3 | NM_005362.3 | 4102 |
| melanoma antigen family A, 6 | MAGEA6 | NM_005363.2 | 4105 |
| CSAG family, member 2 | CSAG2 (TRAG3) | NM_004909.1 | 9598 |
| melanoma antigen family A, 12 | MAGEA12 | NM_005367.4 | 4111 |
| melanoma antigen family A, 2 | MAGEA2 | NM_005361.2 | 4101 |
| tripartite motif-containing 51 | TRIM51 | NM_032681.1 | 84767 |
| neuropilin 2 | NRP2 | NM_003872.2 | 8828 |
| melanoma antigen family A, 1 (directs expression of antigen MZ2-E) | MAGEA1 | NM_004988.3 | 4100 |
| musashi homolog 2 (*Drosophila*) | MSI2 | BF029215 | 124540 |
| Glycophorin C (Gerbich blood group) | GYPC | H38635 | 2995 |
| secreted phosphoprotein 1 (osteopontin, bone sialoprotein I, early T-lymphocyte activation 1) | SPP1 | NM_001040060.1 | 6696 |
| SRY (sex determining region Y)-box 5 | SOX5 | NM_006940.4 | 6660 |
| kinesin family member C1 | KIFC1 | NM_002263.2 | 3833 |
| histone linker H1 domain, spermatid-specific 1 | HILS1 | NM_194072.1 | 373861 |
| regulator of G-protein signalling 20 | RGS20 | BC018618.1 | 8601 |
| BUB1 budding uninhibited by benzimidazoles 1 homolog (yeast) | BUB1 | NM_004336.2 | 699 |
| insulin-like growth factor 2 mRNA binding protein 3 | IGF2BP3 | NM_006547.2 | 10643 |
| FERM domain containing 5 | FRMD5 | NM_032892.3 | 84978 |
| chromosome 1 open reading frame 90 | C1orf90 | BC004269.1 | 84734 |
| eyes absent homolog 4 (*Drosophila*) | EYA4 | BE674583 | 2070 |
| BCL2-related protein A1 | BCL2A1 | NM_004049.2 | 597 |
| solute carrier family 16 (monocarboxylic acid transporters), member 4 | SLC16A4 | NM_004696.1 | 9122 |
| v-akt murine thymoma viral oncogene homolog 3 (protein kinase B, gamma) | AKT3 | NM_005465.3 | 10000 |
| CDC45 cell division cycle 45-like (*S. cerevisiae*) | CDC45L | NM_003504.3 | 8318 |
| SEC22 vesicle trafficking protein-like 3 (*S. cerevisiae*) | SEC22L3 | NM_032970.2 | 9117 |
| paternally expressed 10 | PEG10 | NM_015068.3 | 23089 |
| popeye domain containing 3 | POPDC3 | NM_022361.3 | 64208 |
| melanoma antigen family A, 5 | MAGEA5 | NM_021049.3 | 4104 |
| glutamate dehydrogenase 2 | GLUD2 | BC005111.1 | 2747 |
| ST6 (alpha-N-acetyl-neuraminyl-2,3-beta-galactosyl-1,3)-N-acetylgalactosaminide alpha-2,6-sialyltransferase 3 | ST6GALNAC3 | NM_152996.1 | 256435 |
| seizure related 6 homolog (mouse)-like 2 | SEZ6L2 | NM_201575.1 | 26470 |
| dual specificity phosphatase 4 | DUSP4 | BE222344 | 1846 |
| ATP-binding cassette, sub-family B (MDR/TAP), member 5 | ABCB5 | BC044248.1 | 340273 |
| Ras protein-specific guanine nucleotide-releasing factor 1 | RASGRF1 | NM_002891.3 | 5923 |
| dual specificity phosphatase 4 | DUSP4 | NM_001394.5 | 1846 |
| FLJ40142 protein | FLJ40142 | BF516262 | 400073 |
| barren homolog 1 (*Drosophila*) | BRRN1 | NM_015341.3 | 23397 |

TABLE D-continued

Genes differentially expressed in metastatic melanoma. Expression
of the genes listed in this table is increased relative to non-metastatic samples.

| Gene description | Gene Symbol | GenBank reference ID | Entrez Gene ID |
|---|---|---|---|
| pleckstrin homology-like domain, family A, member 1 | PHLDA1 | NM_007350.3 | 22822 |
| matrix metallopeptidase 14 (membrane-inserted) | MMP14 | NM_004995.2 | 4323 |
| dual specificity phosphatase 6 | DUSP6 | NM_001946.2 | 1848 |
| dpy-19-like 1 (C. elegans) | DPY19L1 | XM_371891.2 | 23333 |
| glutamate dehydrogenase 1 | GLUD1 | AA909218 | 2746 |
| LOC346615 | LOC346615 | XM_934971.1 | 645591 |
| calumenin | CALU | NM_001219.2 | 813 |
| ring finger protein 157 | RNF157 | BF056204 | 114804 |
| PR domain containing 13 | PRDM13 | NM_021620.2 | 59336 |
| PDZ binding kinase | PBK | NM_018492.2 | 55872 |
| KIAA1618 | KIAA1618 | NM_020954.2 | 57714 |
| neural precursor cell expressed, developmentally down-regulated 4-like | NEDD4L | NM_015277.2 | 23327 |
| bicaudal D homolog 1 (Drosophila) | BICD1 | BC010091.2 | 636 |
| ribonucleotide reductase M2 polypeptide | RRM2 | NM_001034.1 | 6241 |

Gene Expression Analysis

As discussed above, combinations of genes are provided herein, for analysis of gene expression in cutaneous tumors (e.g., primary melanoma samples) to determine whether the tumors exhibit a metastatic expression pattern. Methods for analyzing gene expression include methods based on hybridization analysis of polynucleotides, sequencing of polynucleotides, and analysis of protein expression (e.g., proteomics-based methods). Commonly used methods are for the quantification of mRNA expression in a sample include northern blotting and in situ hybridization (Parker & Barnes, Methods in Molecular Biology 106:247-283, 1999); RNAse protection assays (Hod, Biotechniques 13:852 854, 1992); and PCR-based methods, such as reverse transcription polymerase chain reaction (RT-PCR) (Weis et al., Trends in Genetics 8:263 264, 1992). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

PCR-Based Methods

Combinations of genes indicative of metastatic or non-metastatic melanoma can be analyzed by PCR. PCR is useful to amplify and detect transcripts from a melanoma sample. Various PCR methodologies are useful for gene expression analyses.

Reverse Transcriptase PCR (RT-PCR). RT-PCR is a sensitive quantitative method that can be used to compare mRNA levels in different samples (e.g., non-metastatic and metastatic melanoma samples, or benign cutaneous and melanoma samples) to examine gene expression signatures.

To perform RT-PCR, mRNA is isolated from a sample (e.g., total RNA isolated from a human melanoma sample). mRNA can be extracted, for example, from frozen or archived paraffin-embedded and fixed (e.g. formalin-fixed) tissue samples. Methods for mRNA extraction are known in the art. See, e.g., Ausubel et al., *Current Protocols in Molecular Biology*, John Wiley and Sons, 1997. Methods for RNA extraction from paraffin embedded tissues are disclosed, for example, in Rupp and Locker, Lab Invest. 56:A67, 1987, and De Andres et al., BioTechniques 18:42044, 1995. Purification kits for RNA isolation from commercial manufacturers, such as Qiagen, can be used. For example, total RNA from a sample can be isolated using Qiagen RNeasy mini-columns. Other commercially available RNA isolation kits include MasterPure™ Complete DNA and RNA Purification Kit (EPICENTRE™, Madison, Wis.), and, Paraffin Block RNA Isolation Kit (Ambion, Inc.). Total RNA from tissue samples can be also isolated using RNA Stat-60 (Tel-Test) or by cesium chloride density gradient centrifugation.

Next, RNA is reverse transcribed into cDNA. The cDNA is amplified in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the conditions and desired readout. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction. The PCR reaction typically employs the Taq DNA polymerase, which has a 5'-3' nuclease activity but lacks a 3'-5' proofreading endonuclease-activity. Two oligonucleotide primers are used to generate an amplicon in the PCR reaction.

Guidelines for PCR primer and probe design are described, e.g., in Dieffenbach et al., "General Concepts for PCR Primer Design" in: PCR Primer, A Laboratory Manual, Cold Spring Harbor Laboratory Press, New York, 133-155, 1995; Innis and Gelfand, "Optimization of PCRs" in: PCR Protocols, A Guide to Methods and Applications, CRC Press, London, 5-11, 1994; and Plasterer, T. N. Primerselect: Primer and probe design. Methods Mol. Biol. 70:520-527, 1997. Factors considered in PCR primer design include primer length, melting temperature (Tm), and G/C content, specificity, complementary primer sequences, and 3'-end sequence. PCR primers are generally 17-30 bases in length, and Tm's between 50-80° C., e.g. about 50 to 7° C. are typically preferred.

For quantitative PCR, a third oligonucleotide, or probe, is used to detect nucleotide sequence located between the two PCR primers. The probe is non-extendible by Taq DNA polymerase enzyme, and typically is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative analysis.

RT-PCR can be performed using commercially available equipment, such as an ABI PRISM 7700™ Sequence Detection System (Perkin-Elmer-Applied Biosystems, Foster City, Calif., USA), or Lightcycler® (Roche Molecular Biochemicals, Mannheim, Germany). Samples can be analyzed using a real-time quantitative PCR device such as the ABI PRISM 7700™ Sequence Detection System™.

To minimize errors and the effect of sample-to-sample variation, RT-PCR is usually performed using an internal standard. A suitable internal standard is expressed at a constant level among different tissues, and is unaffected by the experimental variable. RNAs frequently used to normalize patterns of gene expression are mRNAs for the housekeeping genes glyceraldehyde-3-phosphate-dehydrogenase (GAPDH) and β-actin.

A variation of the RT-PCR technique is real time quantitative PCR, which measures PCR product accumulation through a dual-labeled fluorigenic probe (i.e., TaqMan™ probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Res. 6:986-994, 1996.

Gene expression can be examined using fixed, paraffin-embedded tissues as the RNA source. Briefly, in one exemplary method, sections of paraffin-embedded tumor tissue samples are cut (~10 μm thick). RNA is extracted, and protein and DNA are removed. After analysis of the RNA concentration, RNA repair and/or amplification steps may be performed, if necessary, and RNA is reverse transcribed using gene specific promoters followed by RT-PCR. Methods of examining expression in fixed, paraffin-embedded tissues, are described, for example, in Godfrey et al., J; Molec. Diagn. 2: 84-91, 2000; and Specht et. al., Am. J. Pathol. 158: 419-29, 2001.

Another approach for gene expression analysis employs competitive PCR design and automated, high-throughput matrix-assisted laser desorption ionization time-of-flight (MALDI-TOF) MS detection and quantification of oligonucleotides. This method is described by Ding and Cantor, Proc. Natl. Acad. Sci. USA 100:3059-3064, 2003.

See also the MassARRAY-based gene expression profiling method, developed by Sequenom, Inc. (San Diego, Calif.).

Additional PCR-based techniques for gene expression analysis include, e.g., differential display (Liang and Pardee, Science 257:967-971, 1992); amplified fragment length polymorphism (iAFLP) (Kawamoto et al., Genome Res. 12:1305-1312, 1999); BeadArray™ technology (Illumina, San Diego, Calif.; Oliphant et al., Discovery of Markers for Disease (Supplement to Biotechniques), June 2002; Ferguson et al., Analytical Chemistry 72:5618, 2000); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888-1898, 2001); and high coverage expression profiling (HiCEP) analysis (Fukumura et al., Nucl. Acids. Res. 31(16) e94, 2003).

Microarrays

Evaluating gene expression of a melanoma sample can also be performed with microarrays. Microarrays permit simultaneous analysis of a large number of gene expression products. Typically, polynucleotides of interest are plated, or arrayed, on a microchip substrate. The arrayed sequences are then hybridized with nucleic acids (e.g., DNA or RNA) from cells or tissues of interest (e.g., cutaneous tissue samples). The source of mRNA typically is total RNA (e.g., total RNA isolated from human melanoma samples, and normal skin samples). If the source of mRNA is a primary tumor, mRNA can be extracted, for example, from frozen or archived paraffin-embedded and fixed (e.g. formalin-fixed) tissue samples.

In various embodiments of the microarray technique, probes to at least 10, 25, 50, 100, 200, 500, 1000, 1250, 1500, or 1600 genes (e.g., genes listed in a Table herein, which distinguish metastatic melanoma from other types of cutaneous tissues) are immobilized on an array substrate (e.g., a porous or nonporous solid support, such as a glass, plastic, or gel surface). The probes can include DNA, RNA, copolymer sequences of DNA and RNA, DNA and/or RNA analogues, or combinations thereof.

In some embodiments, a microarray includes a support with an ordered array of binding (e.g., hybridization) sites for each individual gene. The microarrays can be addressable arrays, and more preferably positionally addressable arrays, i.e., each probe of the array is located at a known, predetermined position on the solid support such that the identity (i.e., the sequence) of each probe can be determined from its position in the array.

Each probe on the microarray can be between 10-50,000 nucleotides, e.g., between 300-1,000 nucleotides in length. The probes of the microarray can consist of nucleotide sequences with lengths: less than 1,000 nucleotides, e.g., sequences 10-1,000, or 10-500, or 10-200 nucleotides in length. An array can include positive control probes, e.g., probes known to be complementary and hybridizable to sequences in the test sample, and negative control probes, e.g., probes known to not be complementary and hybridizable to sequences in the test sample.

Methods for attaching nucleic acids to a surface are known. Methods for immobilizing nucleic acids on glass are described, e.g., Schena et al, Science 270:467-470, 1995; DeRisi et al, Nature Genetics 14:457-460, 1996; Shalon et al., Genome Res. 6:639-645, 1996; and Schena et al., Proc. Natl. Acad. Sci. U.S.A. 93:10539-11286, 1995). Techniques are known for producing arrays with thousands of oligonucleotides at defined locations using photolithographic techniques are described by Fodor et al., 1991, Science 251:767-773, 1991; Pease et al., Proc. Natl. Acad. Sci. U.S.A. 91:5022-5026, 1994; Lockhart et al., Nature Biotechnology 14:1675, 1996; U.S. Pat. Nos. 5,578,832; 5,556,752; and 5,510,270). Other methods for making microarrays have been described. See, e.g., Maskos and Southern, Nuc. Acids. Res. 20:1679-1, 684, 1992. In principle, and as noted supra, any type of array, for example, dot blots on a nylon hybridization membrane (see Sambrook et al., Molecular Cloning, A Laboratory Manual, 2nd Ed., Vols. 1-3, Cold Spring Harbor Laboratory, Cold Spring Harbor, N.Y. (1989)) could be used.

The polynucleotide molecules to be analyzed may be from any clinically relevant source, and are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. For example, the test polynucleotide molecules include total cellular RNA, poly(A)+ messenger RNA (mRNA), or fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. No. 5,545,522, 5,891,636, or 5,716,785). Methods for preparing RNA are known and are described, e.g., in Sambrook et al., *Molecular Cloning, A Laboratory Manual* (2$^{nd}$ Ed.), Vols. 1-3, Cold Spring Harbor Laboratory, Cold Spring Harbor, N.Y., 1989. RNA can be fragmented by methods known in the art, e.g., by incubation with $ZnCl_2$, to generate fragments of RNA.

Test polynucleotide molecules that are poorly expressed in particular cells can be enriched using normalization techniques (Bonaldo et al., Genome Res. 6:791-806, 1996).

The test polynucleotides are detectably labeled at one or more nucleotides. Any method known in the art may be used to detectably label the polynucleotides.

Nucleic acid hybridization and wash conditions are chosen so that the test polynucleotide molecules specifically bind or specifically hybridize to the complementary polynucleotide sequences of the array, preferably to a specific array site, wherein its complementary nucleic acid is located. General parameters for specific (i.e., stringent) hybridization conditions for nucleic acids are described in Sambrook et al., supra, and in Ausubel et al., *Current Protocols in Molecular Biology*, vol. 2, Current Protocols Publishing, New York, 1994. Typically, stringent conditions for short probes (e.g., 10 to 50 nucleotide bases) will be those in which the salt concentration is at least about 0.01 to 1.0 M at pH 7.0 to 8.3 and the temperature is at least about 30° C. Stringent conditions can also be achieved with the addition of destabilizing agents such as formamide. When fluorescently labeled probes are used, the fluorescence emissions at each site of a microarray can be detected by scanning confocal laser microscopy or other methods (see Shalon et al., Genome Research 6:639-645, 1996; Schena et al., Genome Res. 6:639-645, 1996; and Ferguson et al., Nature Biotech. 14:1681-1684, 1996). Signals are recorded and typically analyzed by computer. Methods for evaluating microarray data and classifying samples are described in U.S. Pat. No. 7,171,311.

Serial Analysis of Gene Expression (SAGE)

Gene expression in melanoma samples can also be determined by serial analysis of gene expression (SAGE), which is a method that allows the simultaneous and quantitative analysis of a large number: of gene transcripts, without the need of providing an individual hybridization probe for each transcript (see, e.g. Velculescu et al., Science. 270:484-487, 1995; and Velculescu et al., Cell 88:243-51, 1997). Briefly, a short sequence tag (about 10-14 nucleotides) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of a population of transcripts can be quantitatively evaluated by determining the abundance of individual tags, and identifying the gene corresponding to each tag.

Protein Detection Methodologies

Immunohistochemical methods are also suitable for detecting the expression of the melanoma signature genes described herein. Antibodies, most preferably monoclonal antibodies, specific for a gene product are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomic methods can allow examination of global changes in protein expression in a sample. Proteomic analysis typically involves separation of individual proteins in a sample by 2-D gel electrophoresis (2-D PAGE), and identification of individual proteins recovered from the gel, e.g. my mass spectrometry or N-terminal sequencing, and analysis of the data using bioinformatics. Proteomics methods can be used alone or in combination with other methods for evaluating gene expression.

In various aspects, the expression of certain genes in a cutaneous sample is detected to provide clinical information (e.g., prognostic information, classification of the tumor from which the sample is derived as a metastatic melanoma or non-metastatic melanoma). Thus, gene expression assays include measures to correct for differences in RNA variability and quality. For example, an assay typically measures and incorporates the expression of certain normalizing genes, such known housekeeping genes, e.g., GAPDH, β-actin, and Cyp1. Alternatively, normalization can be based on the mean or median signal (Ct) of all of the assayed genes or a large subset thereof (global normalization approach). In some embodiments, a normalized test RNA (e.g., from a patient sample) is compared to the amount found in a metastatic melanoma, non-metastatic melanoma, and/or normal skin sample reference set. The level of expression measured in a particular test sample can be determined to fall at some percentile within a range observed in reference sets.

Kits

The technology herein includes kits for evaluating gene expression (e.g., RNA or protein) in melanoma samples. A "kit" refers to a combination of physical elements, e.g., probes, including without limitation specific primers, labeled nucleotic acid probes, antibodies, protein-capture agent(s), reagent(s), instruction sheet(s) and other elements useful to practice the technology described herein. These physical elements can be arranged in any way suitable for carrying out the invention.

A kit for analyzing protein expression can include specific binding agents, such as immunological reagents (e.g., an antibody, e.g., a labeled antibody) for detecting proteins expressed of one or more genes described herein (e.g., one or more genes from Table A, Table B, Table C, or Table D). For example, the kit can include an antibody that detects expression of GJB6, an antibody that detects expression of SPPRR1A, and an antibody that detects expression of SERPINB5, in a tissue section.

Kits for analyzing RNA expression include, for example, a set of oligonucleotide probes for detecting expression of a set of genes described herein (e.g., five or more genes from Table A, Table B, Table C, or Table D). The probes can be provided on a solid support, as in an array (e.g., a microarray), or in separate containers. The kits can include a set of oligonucleotide primers useful for amplifying a set of genes described herein, e.g., to perform PCR analysis. Kits can include further buffers, enzymes, labeling compounds, and the like.

EXAMPLES

To identify the genes involved in the metastatic process of melanoma, various non-metastatic primary skin cancers were compared to metastatic melanoma utilizing a gene microarray approach followed by functional validation of select genes. Distinct gene expression changes occurring along the spectrum of primary melanoma tumor thickness and metastatic melanoma were discovered.

Example 1

Gene Expression Differences Between Primary Cutaneous Cancer and Metastatic Melanoma Tumor samples were obtained from patients with primary cutaneous melanoma (PCM), squamous cell carcinoma (SCC), basal cell carcinoma (BCC) and metastatic melanoma (MM). Gene expression in the samples was examined by microarray analysis as described in the Materials and Methods, below. An initial training set of 23 tumors revealed 2,014 Affymetrix probe sets with a greater than 2-fold difference in the average gene expression level between the metastatic melanoma (MM) and primary cutaneous cancers. This preliminary list, consisting of 1,141 well characterized and 471 poorly characterized human genes, indicates that a substantial difference exists between the metastatic tumors and the non-metastatic tissue types. The expression differences allow for a relatively robust gene classification of tissue samples into groups of metastatic samples and non-metastatic primary tumors. All tumor samples were clustered utilizing the 2,014 probe sets and individually identified as metastatic or non-metastatic based upon the characteristics of tumor samples in the same cluster. The initial set of samples comprised a training set for which 22 of 23 samples were correctly partitioned into the cluster containing primary melanoma or the cluster containing MM samples. A single primary melanoma with a Breslow's tumor thickness of 90 mm was misclassified as a MM sample. Two independent test sets comprised of primary and MM samples were similarly classified, utilizing the 2,014 probe sets and hierarchical clustering. Co-clustering led to the correct identification of 56 of 60 melanoma samples. In general, the misidentified samples were thick primary melanomas classified as MM. Of note, several normal human skin samples were analyzed and found to classify as non-metastatic by their gene expression profiles.

A subset of melanoma samples were examined in order to generate a more comprehensive list of genes that were differentially expressed between MM and PCM using serial analysis of microarrays (SAM). This analysis identified 1,352 probe sets with higher expression in the metastatic samples and 2,991 probe sets with higher expression in non-metastatic samples. This list was further reduced by removing probe sets that did not appear to have an average difference greater than 2-fold between groups. The resultant complete gene list is shown above in Tables A and B, above. This final list consists of 1,667 Affymetrix probe sets that detect 247 poorly defined transcripts, 84 minimally defined genes, and 1007 well characterized human genes. From this list, 316 genes were highly expressed in MM compared to 1022 genes that were more highly expressed in the non-metastatic: cancers and normal skin.

A subset of the full gene list is shown below in Table 1 below. This table illustrates two main trends. There is a shift in the kind of genes expressed, perhaps related to the fundamental characteristics of the cells comprising the tumors. For example, there is higher expression levels in MM for several melanoma-associated tumor antigens. (MAGE, CSAG2), genes implicated in melanoma progression (GDF15, MMP14, SPP-1), cell cycle progression (CDK2, TYMS, BUB1), and the prevention of apoptosis (BIRC5, BCL2A1). These changes may reflect the higher growth capacity of the metastatic tumors. Conversely, among the 997 genes with reduced expression in MM samples, many are implicated in keratinocyte differentiation and epidermal development, such as loricrin (LOR), involucrin (IVL), and keratin-5 (KRT5), suggesting a loss of epidermal characteristics. These expression changes suggest important comparative differences between non-metastatic and metastatic tumors.

Analysis of the functional classes of genes changed using gene ontology revealed that 15 genes associated with keratinocyte differentiation and 32 genes involved in epidermis development were down-regulated in the metastatic samples (FIG. 1A). These losses were complemented by the increased expression of genes involved in several cellular processes, such as DNA repair, protein transport, melanocyte differentiation, muscle development, nervous: system development and carbohydrate metabolism. Table 1 further illustrates that the magnitude of change in those genes under-expressed was much greater on average than the level of change in over-expressed genes. Overall, the losses in gene expression are both greater in number and magnitude compared to the gains in gene expression in MM samples.

Another observation is that there are a larger number of genes with reduced expression in the metastatic tumors and the degree of decrease is much greater. In other words, the loss of gene expression is greater than the gain of new gene expression. This is consistent with the observation of dedifferentiation which is believed to occur with the development of cancer.

Figure 1B:
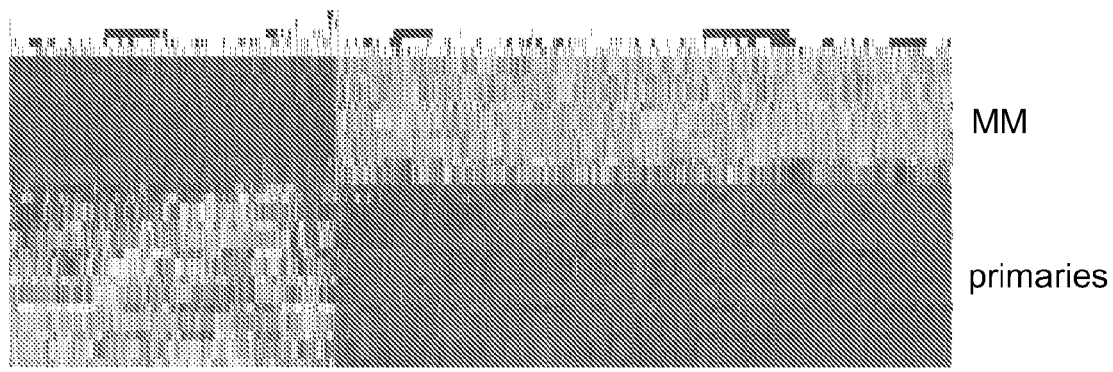
FIG. 1B is a heatmap depicting the relative gene expression of the full spectrum of genes described herein in the non-metastatic (primary) tumors relative to the metastatic tumors (MM). The dark grey shading (appearing primarily in the upper left and lower right quadrants) corresponds to higher than average gene expression, black depicts average gene expression, and the light shading (appearing primarily in lower left and upper right quadrants) depicts lower than average gene expression. Average is set as the average across all the samples used in the figure. Individual rows represent individual tumor samples and individual columns depict individual genes identified in the experiments described herein.

The initial statistical analysis of microarray samples of metastatic melanoma and non-metastatic cutaneous tumors leads to the conclusion that a fundamental difference exists between tumors containing metastatic potential and tumors without demonstrated metastatic potential. In the case of melanoma, it would appear the metastatic potential is associated with a large number of changes in gene expression and fundamental changes in the spectrum of genes expressed. Any measurement of this programmatic shift in gene expression would be useful for the identification of metastatic melanoma cells within a primary melanoma tumor. The data presented in Table 1 addressed the question of whether there were genes differentially expressed (increased or decreased) between primary (BCC/SCC/PCM) and metastatic cancers (metastatic melanoma). The full names of each gene (for named genes), gene symbol, accession number and gene identification for all genes>2-fold up- or down-regulated in metastatic melanoma are provided in Tables A and B above. FIG. 1B is a heatmap depicting the relative gene expression of the full spectrum of genes described herein in the non-metastatic tumors relative to the metastatic tumors. Darker gray shading corresponds to higher than average gene expression, black corresponds to average gene expression, and light gray correspond to lower than average gene expression. FIG. 1B demonstrates that the combination of genes discovered herein dramatically separates metastatic tumors from non-metastatic tumors.

TABLE 1

Differential gene expression between metastatic melanoma and non-metastatic cutaneous tumors

| Gene symbol | Increase in metastatic melanoma relative to | | Gene symbol | Decrease in metastatic melanoma relative to | |
|---|---|---|---|---|---|
| | MIS/Thin | BCC/SCC/MIS/Thin | | MIS/Thin | BCC/SCC/MIS/Thin |
| MAGEA3 | 125 | 27 | CALML5 | 193 | 228 |
| MAGEA1 | 24 | 13 | DSC1 | 186 | 198 |
| MAGEA6 | 119 | 25 | DSC3 | 64 | 71 |
| MAGEA2 | 57 | 31 | PKP1 | 166 | 240 |
| MAGEA12 | 57 | 29 | CLCA2 | 162 | 177 |
| MAGEA5 | 10 | 6 | DSG3 | 160 | 119 |
| CSAG2 | 76 | 36 | DSG1 | 160 | 178 |
| TRIM51 | 51 | 35 | LY6D | 143 | 147 |
| GDF15 | 30 | 47 | SERPINB3 | 111 | 184 |
| GYPC | 18 | 14 | SERPINB5 | 199 | 227 |
| SPP1 | 15 | 7 | SERPINB7 | 10 | 144 |
| KIFC1 | 15 | 3 | C19orf33 | 122 | 135 |
| RGS20 | 14 | 14 | FLG | 112 | 112 |
| C1orf90 | 13 | 15 | KRT5 | 49 | 62 |
| BCL2A1 | 12 | 12 | KRT17 | 111 | 196 |
| SOX5 | 15 | 8 | KRT16 | 105 | 274 |
| SLC16A4 | 12 | 29 | KLK7 | 99 | 112 |
| AKT3 | 11 | 9 | KLK8 | 23 | 32 |
| PEG10 | 11 | 10 | KLK10 | 27 | 81 |
| BUB1 | 14 | 3 | KLK11 | 6 | 83 |
| RASGRF1 | 8 | 12 | LOR | 95 | 98 |
| MMP14 | 8 | 6 | LGALS7 | 84 | 89 |
| SPRED1 | 6 | 4 | CST6 | 82 | 56 |
| GPR19 | 6 | 5 | TRIM29 | 79 | 119 |
| CDK2 | 6 | 7 | SFN | 77 | 125 |
| HOXA10 | 3 | 4 | ASAH3 | 69 | 56 |
| HOXB6 | 4 | 6 | GATA3 | 63 | 54 |
| HOXB7 | 5 | 7 | CBLC | 60 | 64 |
| HOXB9 | 3 | 3 | RAB25 | 59 | 78 |
| HEY1 | 7 | 16 | S100A14 | 27 | 44 |
| DUSP4 | 8 | 10 | S100A7 | 57 | 60 |
| DUSP6 | 8 | 6 | S100A7L1 | 21 | 82 |
| CDC45L | 7 | 8 | ICEBERG | 52 | 48 |
| CDC6 | 9 | 4 | IVL | 50 | 76 |
| RRM2 | 6 | 4 | ELOVL4 | 38 | 34 |
| TYMS | 4 | 3 | CXCL14 | 36 | 37 |
| BIRC5 | 4 | 2 | FOXN1 | 33 | 34 |

Abbreviations:
PCM, primary cutaneous melanoma,
MIS, melanoma-in-situ,
BCC, basal cell carcinoma,
SCC, squamous cell carcinoma,
Thin, thin melanomas <1.5 mm in Breslow's thickness.

Example 2

Figure 1C:
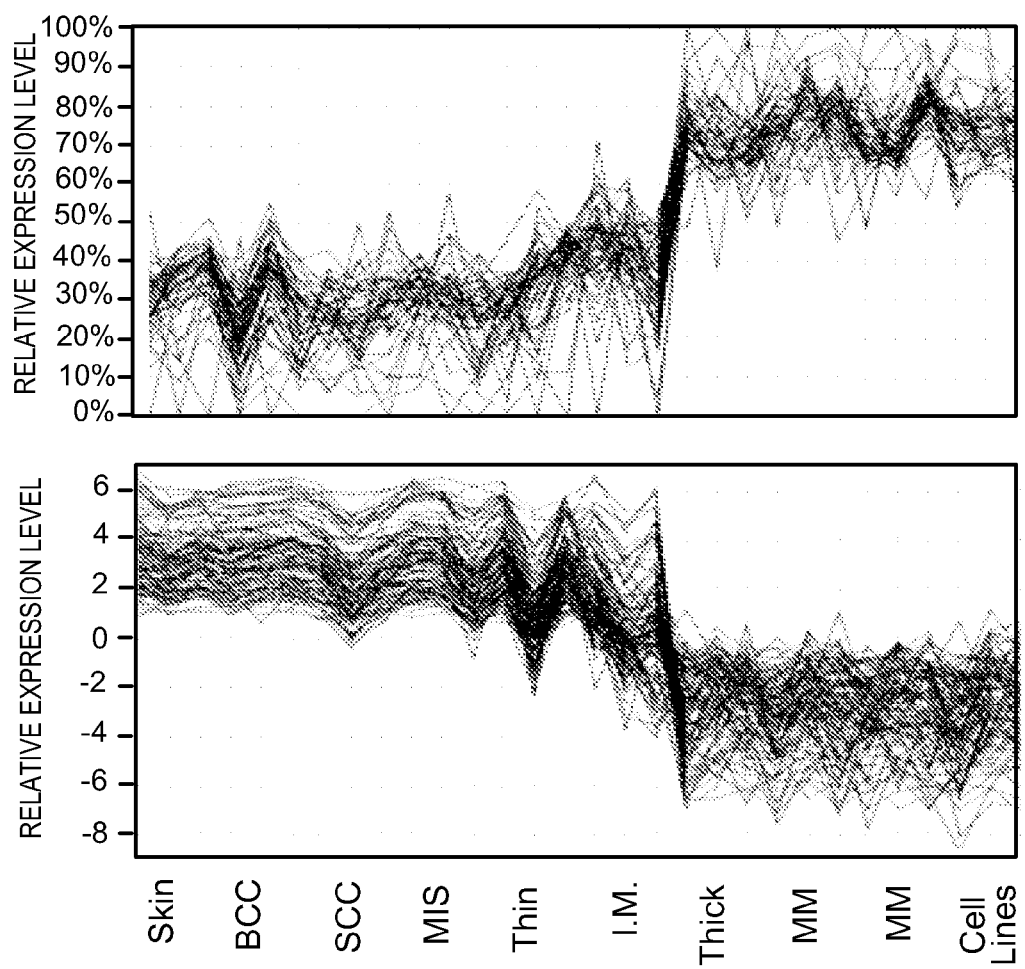
FIG. 1C is a set of graphs depicting relative expression levels of a subset of genes described herein in samples of normal skin, basal cell carcinoma (BCC), squamous cell carcinoma (SCC), melanoma in situ (MIS), thin melanoma, melanoma of intermediate thickness (I.M.), thick primary, metastatic melanoma (subcutaneous, lymph node and distant; MM), and melanoma cell lines derived from patients with stage IV melanoma. Genes more highly expressed in metastatic melanoma are depicted in the upper graph and genes whose expression is decreased in the metastatic melanoma cells are depicted in the lower graph. In both cases the transition from a non-metastatic tissue expression level to the metastatic tissue expression level occurs in the I.M. thickness sample set. This figure illustrates the distinct differences between the non-metastatic and metastatic melanoma tumors and also illustrates the transitional tumor class that would most benefit from assays to detect the metastatic cell type.

Identification of Gene Expression Differences Between Metastatic and Non-Metastatic Tumor Samples The relative gene expression levels of 177 genes across the spectrum of tissue samples examined is shown graphically in FIG. 1C. This analysis reveals a consistent level of expression through all of the presumed "non-metastatic" samples (normal skin, BCC, SCC, MIS, Thin). A marked change in the gene expression levels is seen, beginning with the I.M. thickness PCM (average Breslow's tumor thickness of 2.1 mm), progressively increasing or decreasing to the expression level representative of MM lesions. All of the thick PCM (average Breslow's thickness 19 mm) exhibited gene expression patterns similar to those of MM samples and daughter MM cell lines. FIG. 1C demonstrates the sharp contrast between metastatic tumors and non-metastatic tumors or normal skin illustrating how gene expression differences could distinguish between these two classes of tissues. The transition zone also illustrates the class of tumors for which a metastatic assessment is particularly useful. A transition appears to occur as primary melanoma tumors thicken. The thicker primary tumors appear to contain gene expression patterns identical to the metastatic melanoma tumors.

The apparent transition zone of gene expression change could represent a critical time period where many tumorigenic events occur or may simply reflect the outgrowth of an aggressive and/or metastatic cell phenotype. To address this issue, a comparative analysis of gene expression patterns in primary melanomas of different Breslow's thickness was performed. PCM and MM samples were compared to elucidate a possible relationship between relative gene expression patterns associated with PCM of increasing Breslow's thickness and that of MM samples. Table 2 (left columns) reveals the relative change in gene expression for a subset of genes throughout the spectrum of primary melanoma tumors to MM samples.

Several genes, such as the MAGE genes, exhibited a steady and consistent increase in gene expression over the entire range of tumor thicknesses. However, a single major shift in expression was observed for most genes when thinner primary tumors were directly compared to thicker ones. This was most apparent when comparing I.M. thickness to thick PCM, with the majority of genes showing the greatest increase in gene expression. Notable exceptions were genes such as SPP1, HOXA10 and MMP14, for which the greatest differential increase in expression was at the comparative interface between thin and I.M. thickness tumor samples. Other genes, such as MMP19, CTH, PDGFRL, C16 orf34 and GPR19, showed the greatest comparative increase in expression when comparing MIS to thin PCM lesions.

A similar phenomenon was observed for genes with decreased expression in primary tumors relative to more advanced lesions (Table 2, right columns). Here, however, the largest proportion of the gene expression change occurred between thick PCM and MM samples. Very little expression of keratins (6B, 16, 17) and SPRR1 (A, B) was observed in MM compared to all primary melanomas, including thick lesions. Several genes, such as TMPRSS4, STAR, ST7L, HAS3, FGFR3, CASZ1 and HR, were found to have gene expression changes at the very earliest stages of tumor thickening. Together, the gene expression patterns do not shift in a coordinated fashion as would be expected as the result of the outgrowth of a clonal aggressive or metastatic cell type. Rather a series of events may occur as PCM tumors thicken that may influence the expression of different groups of genes ultimately leading to the fully metastatic cell type. This data indicates that some gene expression changes may be indicative of earlier events in the progression to full metastasis. The indicated changes in gene expression may signal that cells in primary melanoma tumors are progressing to a fully metastatic-state or that have already acquired the metastatic state. In either case, the genes are useful markers for identifying aggressive tumors which warrant more aggressive treatment.

All annotated genes listed in Table 2 with a "<2" indicates that any difference between tumors for each comparative analysis was less than 2-fold. Underlined numbers indicate the greatest change in gene expression across varying PCM tumor thickness for each gene.

TABLE 2

Comparative analysis of gene expression changes in primary and metastatic melanoma.

| | Relative increase in gene expression | | | | | | Relative decrease in gene expression | | | | |
|---|---|---|---|---|---|---|---|---|---|---|---|
| Gene Symbol | MIS to Thin | Thin To IM | IM to Thick | Thick to Met | MIS to Met | Gene Symbol | MIS to Thin | Thin To IM | IM to Thick | Thick to Met | MIS to Met |
| MAGEA2 | <2 | 8.6 | 9.4 | 3.1 | 30.7 | SPRR1A | <2 | <2 | <2 | 129.4 | 239.3 |
| MAGEA3 | <2 | 8.1 | 10.7 | 3 | 83.8 | SPRR1B | <2 | <2 | <2 | 52.8 | 100.8 |
| MAGE A6 | <2 | 7.1 | 9.8 | 2.7 | 103 | KRT16 | <2 | <2 | <2 | 68.3 | 195.5 |
| MAGEA1, 2 | <2 | 2.5 | 8.9 | 2.6 | 81.5 | KRT17 | <2 | 2.6 | <2 | 27.4 | 57.6 |
| MAGE A1 | <2 | <2 | 11.1 | <2 | 25.4 | KRT6B | <2 | <2 | <2 | 39.7 | 100.9 |
| MAGE A5 | <2 | 2.2 | 3.9 | <2 | 11.7 | AQP3 | <2 | <2 | 3.2 | 6.1 | 43.2 |
| MMP19 | 5.4 | <2 | <2 | <2 | 7.4 | CD24 | <2 | <2 | 2 | 4.4 | 18.7 |
| PDGFRL | 22.3 | 3.6 | <2 | <2 | 6.3 | FLG | <2 | <2 | 3 | 24.1 | 140 |
| C16orf34 | 5.4 | <2 | <2 | <2 | 18.5 | IVL | <2 | 2.2 | <2 | 13.9 | 84.1 |
| CTH | 3.9 | <2 | <2 | <2 | 8.8 | KLK7 | <2 | <2 | 6.5 | 8.9 | 128 |
| GPR19 | 4.2 | <2 | 3 | <2 | 23.9 | LGALS7 | <2 | <2 | 3.4 | 17.3 | 109.3 |
| SPPI | <2 | 13.1 | <2 | <2 | 44.9 | LOR | <2 | <2 | 2.4 | 22.6 | 120.4 |
| HOXA10 | <2 | 3.3 | <2 | <2 | 3.8 | RAB25 | <2 | <2 | 3.3 | 10.3 | 88.4 |
| MMP14 | <2 | <2 | 3.6 | <2 | 2.1 | 9 | SFN | <2 | <2 | <2 | 10.6 | 24.2 |
| AKT3 | <2 | <2 | 7.5 | <2 | 14.3 | C19orf33 | 3.1 | <2 | 4.6 | 13.3 | 220.3 |
| BCL2A1 | <2 | 2.2 | 4.8 | <2 | 18.7 | ASAH3 | <2 | <2 | 25.9 | <2 | 60 |
| BIRC5 | <2 | <2 | 3.7 | <2 | 3.4 | KRT15 | <2 | <2 | 27.1 | 2.2 | 104.9 |
| BUB1 | <2 | <2 | 9.4 | <2 | 10.8 | ELOVL4 | <2 | 2.3 | 14.7 | <2 | 41.9 |
| CDC45L | <2 | <2 | 13 | <2 | 9.1 | GATA3 | 2.5 | <2 | 14.3 | <2 | 23.5 |
| CDK2 | <2 | <2 | 4.8 | <2 | 8.4 | MUC15 | <2 | 2.2 | 11.9 | <2 | 25 |
| CSAG2 | <2 | <2 | 19.6 | 2.6 | 54.5 | SCEL | <2 | <2 | 28.8 | <2 | 71.8 |
| DUSP4 | 2 | <2 | 5.7 | <2 | 12.5 | TP73L | <2 | <2 | 5.5 | 3.4 | 41.2 |
| DUSP6 | <2 | <2 | 3.7 | <2 | 10.5 | RORA | <2 | <2 | 6.2 | 2.2 | 26.6 |
| GYPC | <2 | <2 | 12.2 | <2 | 14.2 | POU2F3 | <2 | <2 | 13.9 | 2.2 | 73.9 |
| HEY1 | <2 | <2 | 5.7 | <2 | 9.3 | ICEBERG | <2 | 2.7 | 6.7 | 4.5 | 32.3 |
| KIFC1 | <2 | <2 | 10.4 | <2 | 16 | CASZ1 | <2 | 4.8 | 2.8 | <2 | 12.3 |
| PEG10 | <2 | 2.4 | 4.1 | <2 | 11.3 | HR | <2 | 3.7 | <2 | <2 | 7.7 |
| RASGRF1 | <2 | <2 | 5.1 | <2 | 9.9 | TMPRSS4 | 8.7 | <2 | <2 | 3.1 | 42 |
| RGS20 | 3.4 | <2 | 9.2 | <2 | 34.3 | STAR | 4.9 | <2 | <2 | <2 | 11.1 |
| SLC16A4 | <2 | <2 | 4.4 | <2 | 26.4 | ST7L | 4.3 | <2 | 3.6 | <2 | 8.4 |
| SOX5 | <2 | <2 | 12.3 | <2 | 19.8 | LTB4R | 4 | <2 | 2.3 | <2 | 9.9 |
| TRIM51 | <2 | 3.1 | 15.9 | <2 | 63.6 | HAS3 | 4.9 | <2 | <2 | 2.5 | 16.6 |
| TYMS | <2 | <2 | 3.6 | <2 | 4.7 | FGFR3 | 3.9 | <2 | 3.2 | <2 | 7.6 |

Abbreviations:
MIS, melanoma-in-situ,
Thin, thin melanomas <1.0 mm in Breslow's thickness,
I.M., intermediate thickness between 1-4 mm, with thick melanomas >4 mm.

Example 3

Comparative Genomic Analysis of Normal Human Epithelial Melanocytes to Primary and Metastatic Melanoma Samples Gene expression profiles of cultured NHEM were compared to PCM and MM samples (Table 3), acknowledging the inherent limitations associated with the comparisons of cultured cells and freshly procured tumor samples. Large differences in gene expression were observed between NHEM and early, non-metastatic PCM (MIS/thin lesions only) and MM samples. Concordant over-expression of genes were found for both comparisons, in particular for such genes as KRT14, GJA1, S100A7(A9) and EHF. Other genes, like the melanoma associated antigens, MAGE A2 and TRAG and PRAME were also found to be highly over-expressed in NHEM to early primary or MM samples. Similarly, a marked decrease in gene expression was observed for several genes, although of a lesser magnitude than seen for the over-expressed genes. Several unique genes including PAEP, HES6, ESDN, NR4A3, c6orf168 and BCL2A1, were under-expressed in NHEM compared to thin PCM. Other genes were also identified as under-expressed in both groups, such as CITED-1, GDF15, QPRT, OCA2, c-MET and MME.

TABLE 3

Comparative gene expression levels of normal human epithelial melanocytes to thin primary cutaneous and metastatic melanoma samples

| Comparative Increase in Gene Expression (Fold Change) | | | | Comparative Decrease in Gene Expression (Fold Change) | | | |
|---|---|---|---|---|---|---|---|
| Gene Symbol | NHEM c/t MIS/Thin | Gene Symbol | NHEM c/t Metastatic Melanoma | Gene Symbol | NHEM c/t MIS/Thin | Gene Symbol | NHEM c/t Metastatic Melanoma |
| KRT14 | 6787 | GJA1 | 759 | MME | 106 | MAP4 | 20 |
| GJA1 | 5929 | SEPP1 | 338 | CITED1 | 77 | OCA2 | 10 |
| EHF | 5487 | KRT14 | 306 | GDF15 | 64 | TRIM7 | 7 |

TABLE 3-continued

Comparative gene expression levels of normal human epithelial melanocytes to thin primary cutaneous and metastatic melanoma samples

| Comparative Increase in Gene Expression (Fold Change) | | | | Comparative Decrease in Gene Expression (Fold Change) | | | |
|---|---|---|---|---|---|---|---|
| Gene Symbol | NHEM c/t MIS/Thin | Gene Symbol | NHEM c/t Metastatic Melanoma | Gene Symbol | NHEM c/t MIS/Thin | Gene Symbol | NHEM c/t Metastatic Melanoma |
| SCEL | 3931 | MAGEA2 | 301 | PAEP | 47 | CITED1 | 6 |
| CLCA2 | 3689 | TRAG3 | 242 | RPEL1 | 45 | TRPM4 | 6 |
| S100A7 | 3609 | EHF | 193 | HES6 | 43 | MME | 5 |
| KRTDAP | 3416 | S100A9 | 160 | ESDN | 37 | TRAP150 | 5 |
| DSC1 | 2782 | S100A7 | 129 | QPRT | 35 | FER1L3 | 4 |
| GJB6 | 2576 | SCEL | 126 | OCA2 | 19 | QPRT | 4 |
| CXCL14 | 2484 | SLC22A3 | 125 | RENBP | 17 | KLF8 | 4 |
| LOR | 2308 | EPHA3 | 124 | NR4A3 | 16 | RPEL1 | 4 |
| KRT6A | 1989 | KRTDAP | 121 | Stat7c | 16 | PACE4 | 4 |
| PKP1 | 1835 | S100A8 | 120 | C6orf168 | 15 | HPCAL1 | 4 |
| SERPINB3 | 1778 | ZIC1 | 119 | BCL2A1 | 14 | ACTR1A | 4 |
| S100A9 | 1768 | CXCL14 | 118 | NTT73 | 14 | MET | 3 |
| KRT15 | 1545 | IL18 | 108 | PSCD3 | 14 | RAB32 | 3 |
| GATA3 | 1347 | PRAME | 102 | HPCAL1 | 13 | TYR | 3 |
| PPL | 1339 | MAGEA6 | 94.7 | MET | 12 | IRF6 | 3 |
| IMUP | 1250 | PLCB4 | 88 | ALS2CR3 | 12 | GDF15 | 3 |
| ICEBERG | 1123 | CLCA2 | 87 | PTPLA | 12 | HINT3 | 3 |
| KRT6B | 1114 | GJB6 | 85 | TBC1D7 | 11 | SLC30A1 | 3 |
| CSTA | 693 | MAGEA3 | 84 | OA1 | 11 | TRPV2 | 3 |
| CST6 | 687 | MMP19 | 59 | TYR | 11 | RSN | 3 |

Example 4

Identification of Putative Oncogenes and Tumor Suppressor Genes in Melanoma

A perusal of the gene expression differences between PCM and MM samples identifies numerous putative oncogenes and tumor suppressor genes (TSG). Table 4 lists several oncogenes and TSG previously implicated in tumor types. The gene with the largest increase in expression (13.2 fold) was SPP-1 or osteopontin. Although not previously identified as an oncogene, osteopontin expression has been shown to correlate with melanoma invasion and tumor progression (Zhou et al., J. Invest. Dermatol. 124:1044-1052, 2005). The lineage-specific oncogene, MITF, previously shown to act as a master regulator of melanocyte development and a critical survival oncogene amplified in melanoma showed a 3.7 fold increase (Garraway et al., Nature. 436:33-35, 2005; Levy et al., Trends Mol. Med. 12:406-14, 2006; McGill et al., J. Biol. Chem. 281:10365-10373, 2006). Of the other genes, GDF15, c-Met and the HOX loci have been shown to act as possible oncogenes in breast cancer, squamous cell lung cancer, prostate and pancreatic cancer. Several of the putative melanoma TSGs have also been previously shown to contribute to the development and progression of cancer in other tumor histologies.

The shifts in gene expression occur at different stages of the thickening process for each of the oncogenes and TSGs listed in Table 4. Some of the genes show a progressive and steady increase or decrease in gene expression as tumors of greater thickness are compared. But for others, such as the oncogenes SPP-1 and GDF15, and the TSGs PITX-1 and CST6, the major shifts in gene expression appear to occur at distinct but different times during the thickening of the primary melanoma tumors. This observation strongly suggests that these changes may occur spontaneously but eventually accumulate to contribute to the final metastatic phenotype.

Table 4 contains a partial list of identified tumor oncogenes and tumor suppressor genes (TSG's) in PCM and MM samples. The fold increase represents the greatest fold change noted throughout all comparisons of each PCM tumor thickness to MM. The activating/suppressive mechanism and affected tumor type are also identified.

TABLE 4

Differential expression of putative tumor oncogenes and suppressor genes in melanoma

| | | | Oncogenes | |
|---|---|---|---|---|
| Gene | Fold Increase | Interval of Increase | Activating Mechanisms in other Tumor Histologies | Affected Tumor Types |
| SPP-1 | 13.2 | Thin to IM | C-Met activation via $\alpha v\beta 3$ receptor, Inhibition of apoptosis | Breast, HCC, Prostate, CRC, Head & Neck |
| MITF | 3.7 | Progressive increase | Somatic alteration via gene amplification (Chr.#3p13-3p14) | None, Lineage Specific for Melanoma |
| CITED-1 (cbp/p300 transactivator) | 12.4 | IM to Thick | Activation of Stat-3, Ras/MAPK kinase signaling via Ets1, Ets2 | Thyroid |

TABLE 4-continued

Differential expression of putative tumor oncogenes and suppressor genes in melanoma

| Gene | | | | |
|---|---|---|---|---|
| GDF15 (PLAB) | 22.7 | IM to Thick | Lineage specific activation or repression of ERK1/2; Integrator of AKT pathway | Breast, CRC, Gastric, Prostate, Pancreatic |
| c-Met | 14.5 | Thick to Met | Ras-Associated Protein (Rap1)/ERK/MAPK, rac1, Grb2, P13K, src activation | CRC, Breast, Ovarian, Pancreatic, Liver |
| HOX Locus (A3, A10, B6, B7, B13) | 2.1-5.0 | Progressive increase | Downstream activation of WT-1, NFKB, NR4A3, BCl.2, p53 | AML, Breast, SCLC |

| Tumor Suppressor Genes | | | | |
|---|---|---|---|---|
| Gene | Fold Decrease | Interval of Decrease | Suppressor Mechanisms in other Tumors Histologies | Affected Tumor Types |
| PITX-1 | 13.9 | Thin to IM | Ras Pathway (RASAL1) | Barrett's [Esophagus] Prostate, Bladder |
| CST6 (CST E/M) | 66.7 | IM to Thick | Hypermethylation | Breast, Glioma |
| PDGFRL | 7.3 | IM to Thick | Gene Deletion from Chr.# 8p21.3-p22 | HCC, CRC, NSCLC |
| DSC3 | 42.8 | Progressive decrease | Hypermethylation | Breast |
| POU2F3 | 49 | Thin to IM | Hypermethylation | Cervical |
| CLCA2 | 162 | MIS/Thin to MM | Hypermethylation | Breast |

Abbreviations:
HCC, hepatocellular carcinoma,
CRC, colorectal carcinoma,
NSCLC, non-small cell lung cancer,
SCLC, squamous cell lung cancer,
AML, acute myelogenous leukemia.

Example 5

Validation of Select Candidate Genes by Semi- and Quantitative RT-PCR Analysis

Figure 2A:
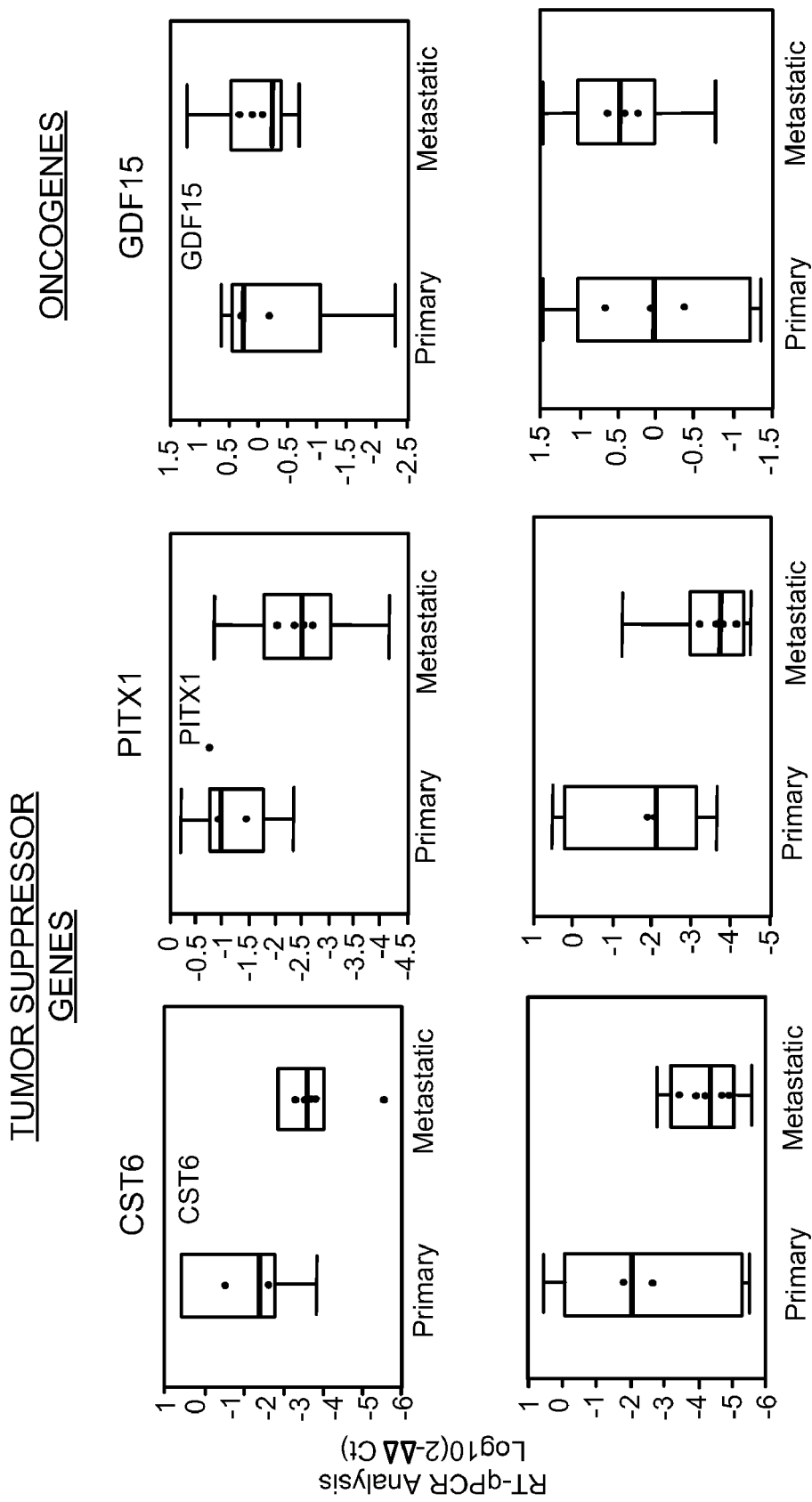
FIG. 2A is a graph depicting comparative quantitative PCR (qPCR) gene expression analysis data of putative tumor suppressor genes (CST6, DSC3, PITX1, POU2F3) and oncogenes (GDF15, SPP-1) in PCM (n=7) and MM (n=13) samples. Relative quantitation of target gene expression for each sample was, determined using the equation $2^{-\Delta\Delta Ct}$, where GAPDH was used as the internal reference and normal skin as the calibrator. Values were Log base 10 transformed (y-axis) so that all values below zero represent a down-regulation in gene expression and values above zero represent an up-regulation in gene expression, compared to normal skin.
Figure 2B:
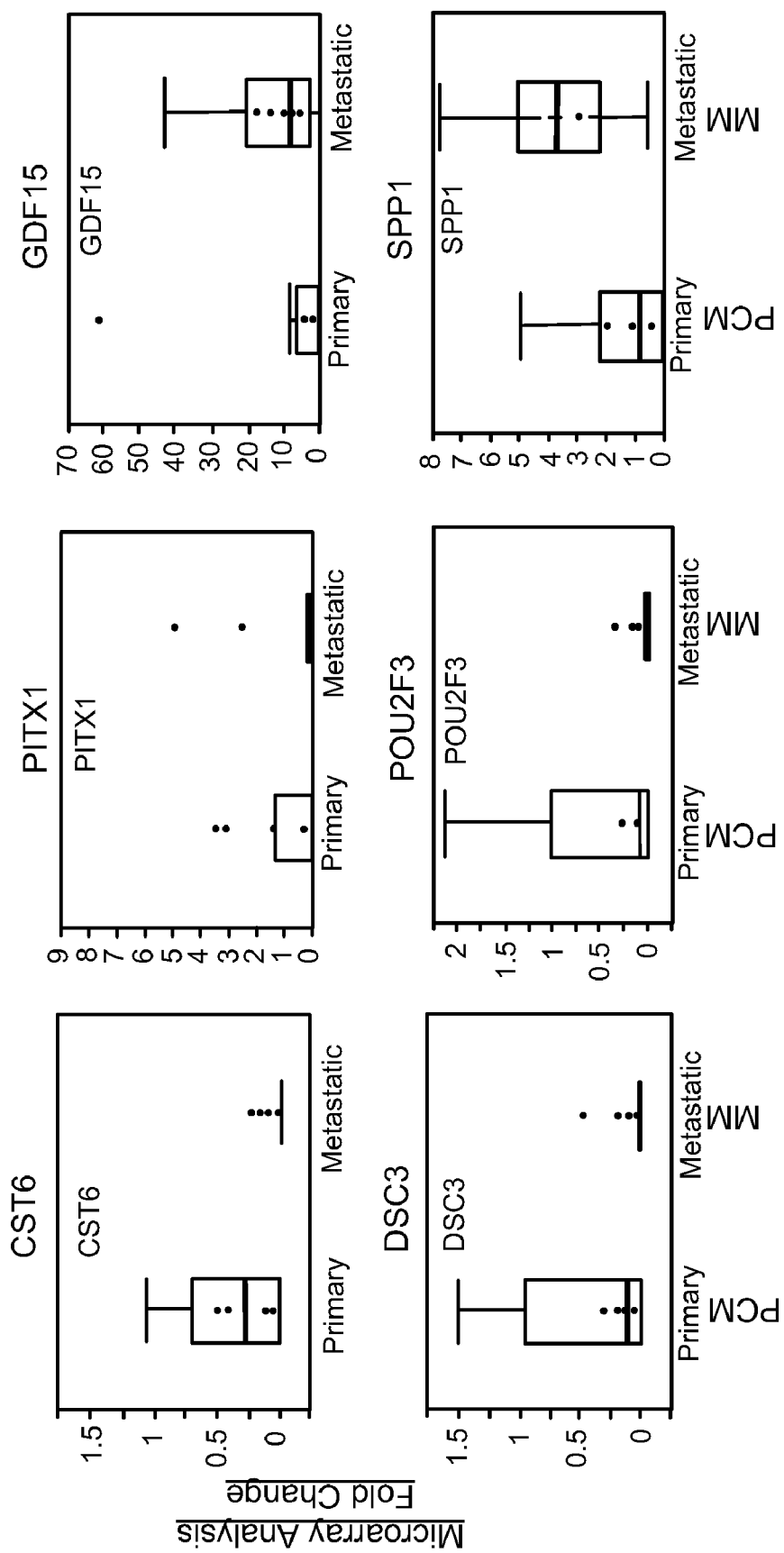
FIG. 2B is a graph depicting results of correlative microarray analysis of gene expression levels in primary and metastatic melanoma samples compared with normal skin. The statistical differences of gene expression between primary (PCM) and metastatic melanoma (MM) samples were analyzed by Wilcoxon's signed rank test; two-tailed significance level was set at $\alpha=0.05$. Compared to PCM samples (n=7), the expression levels of 4 putative tumor suppressor genes (CST6, p<0.0001; DSC3, p<0.0001; PITX1, p=0.0043, POU2F3, p<0.0001) were significantly decreased in MM samples (n=40), while the expression of putative oncogenes (GDF15, p=0.0027; SPP1, p<0.0001) were significantly increased in MM samples.
Figure 3A:
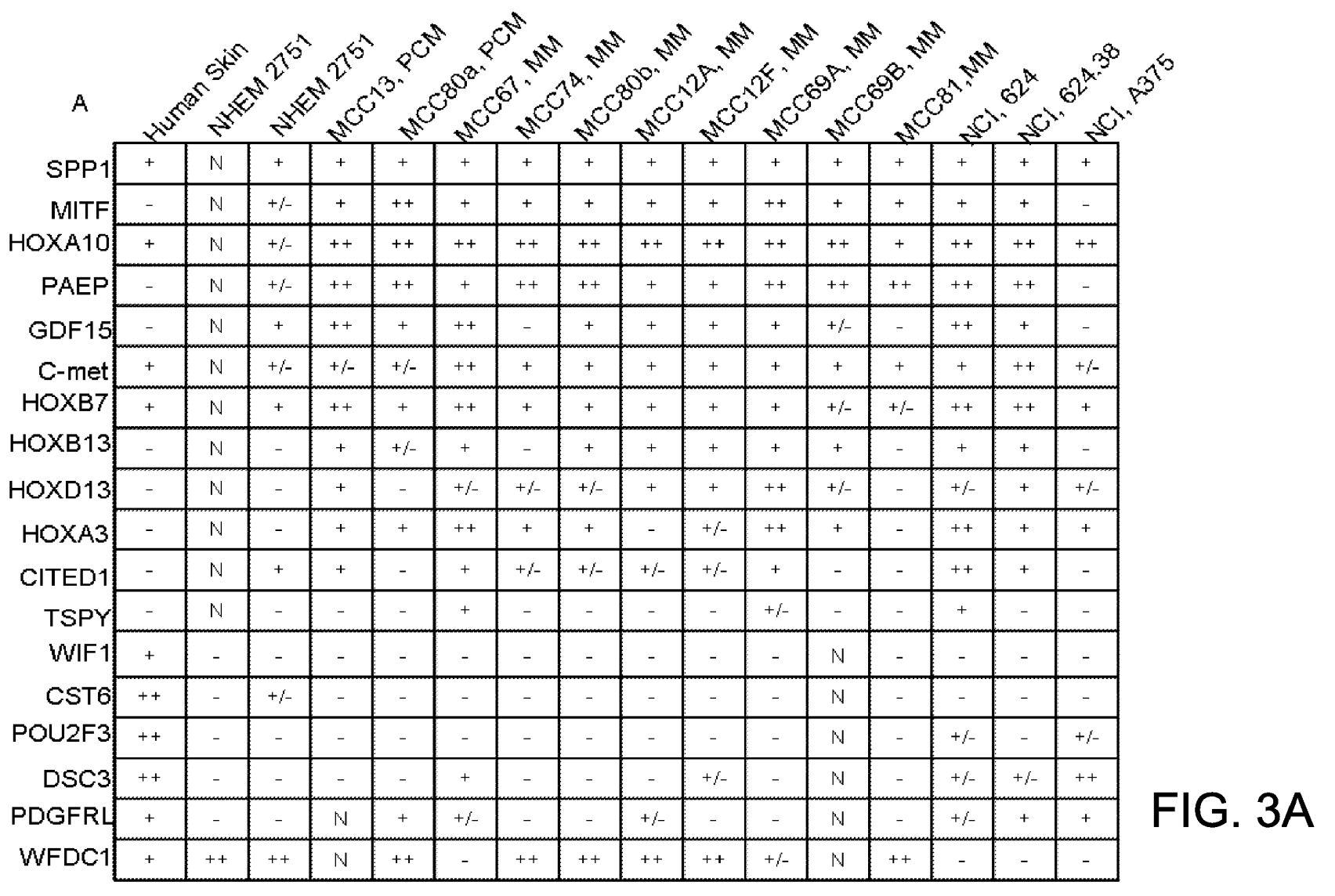

To further validate the expression of putative TSG and oncogenes in our melanoma panel, real-time quantitative polymerase chain reaction (RT-qPCR) assays were performed on 20 previously arrayed samples, comprised of 7 PCM and 13 mM samples. The results are depicted in FIG. 2A, which shows an overall decreased level of mRNA expression of TSG and increased mRNA expression of oncogenes compared to normal skin, which was used to calibrate the expression levels to a value of zero for graphing purposes. FIG. 2A also shows that the MM samples expressed decreased levels of TSGs and increased levels of oncogenes relative to the PCM samples. This was consistent for all PCM samples compared to MM, although not statistically significant for comparisons across different thicknesses of PCM. FIG. 2B shows the original microarray data normalized and graphed in a manner identical to the PCR data. A significant correlation for all TSG and oncogenes examined was found. Utilizing semi-quantitative PCR analysis, several primary and MM: daughter cell lines derived from the freshly procured melanoma samples, normal skin and NHEM, were examined for oncogene and TSG mRNA expression. The results are depicted in FIG. 3A. Several of the cell lines exhibited high levels of expression for several of the reported oncogenes while there was a much higher percentage of loss of TSG expression seen in most cell lines examined. Overall, a favorable correlation was observed between the microarray results and both quantitative and semi-quantitative PCR analysis for daughter and non-daughter primary and MM cell lines. A subset of the genes listed in FIG. 3A are useful for evaluating metastatic and non-metastatic phenotypes. Those genes are included in Tables A and B, above.

Figure 3B:
FIG. 3B is a set of western blots in which expression of SPP1 (FIG. 3B, panels a and b), DSC3, CLCA2, PDGFRL, and TUBULIN (FIG. 3B, panels c, d, e, and f, respectively) was examined in metastatic melanoma (MM) and primary cutaneous melanoma (PCM) daughter cell lines. The blot depicted in FIG. 3B, panels a and b, was probed with anti-SPP1 antibody. Panels c, d, e, and f, were probed with antibodies to DSC-3, CLCA2, PDGFRL, and α-tubulin (as an internal control), respectively. Lanes 1-3 of each blot contained PCM samples. Lanes 4-6 of each blot contained MM cell lines.

FIG. 3B depicts the expression level of several oncogenes an TSGs cell lines derived from normal human melanocytes, normal skin, and cell lines derived from tumor samples. In general, oncogenes are more highly expressed in the cell lines derived from tumors and TSGs are more highly expressed: in the normal skin and normal human melanocytes consistent with their role as possible markers of the metastatic state. These measurements were made with semi-quantitative PCR, demonstrating that alternative measures of gene expression can distinguish the metastatic signature.

Example 6

Functional Analysis of Select Candidate Genes by Western Blot Analysis and Immunohistochemistry To independently verify and validate the gene expression changes at the protein level, protein expression of several suspected oncogenes and TSG was examined using Western Blot analysis. Osteopontin (SPP-1) protein expression was examined, both from melanoma cell lysates and conditioned cell free media derived from 2 primary and 6 MM daughter cell lines (FIG. 3B, a, b). Interestingly, the protein expression level of 2 subcutaneous melanoma nodules (MCC 12A, 12F) procured from the same patient with MM differed. Similarly, two paired cell lines (MCC80a from a primary melanoma from a synchronous metastatic lymph node, MCC80b), noting a slight increase in SPP-1 protein expression in the latter. Several other melanoma cell lines exhibited minimal SPP-1 protein expression. (MCC12F, 66C, 80a and 89). Similar findings were noted between melanoma cell lysates and conditioned cell media.

Analysis of suspected TSG in 3 primary and 3 metastatic melanoma cell lines revealed a very low level of protein expression of DSC3 in 6/6 cell lines (FIG. 3B, panel c) with 4/6 (2/3 primary and 2/3 MM) cell lines expressing the protein for CLCA2 (FIG. 3B, panel d). Interestingly, PDGFRL protein expression was observed in a single primary cell line, with no evidence of expression in any of the metastatic cell lines (FIG. 3B, panel e). The cellular staining patterns of skin and melanoma samples are available for viewing at the Human Protein Atlas website (world wide web address at proteinatlas.org/). These observations demonstrate that analysis of protein expression (e.g., antibody-based assays) can be used as measures of gene expression for the identification of metastatic melanoma in primary cutaneous tumors.

The molecular analyses described herein clearly identifies distinct molecular profiles associated with MM which are different from PCM, SCC, and BCC as well as normal melanocytes and skin. Using the refined gene list (Tables A and B), the metastatic character of tumors (SCC/BCC/PCM/MM) can be classified correctly greater than 90% of the time. One major difficulty is classification of thick primary melanoma tumors, where occasionally, these tumors appeared to have the gene expression signature of MM. It was discovered that these tumors represent primary tumors which have already acquired the metastatic gene expression pattern. Detection methods that examine expression of the gene combinations described herein allow identification of such tumors and inform subsequent clinical decisions.

In conclusion, a clear pattern of gene expression change was observed in the non-metastatic and metastatic samples examined. There is a clear point of transition in gene expression when comparing I.M. to: thick PCM, revealing specific groupings of genes involved in this process. Several of these genes and combinations thereof have never before revealed as functional or relevant in melanoma. The specific genes involved in this dynamic and fluid change in gene expression provides the basis for the determination of whether a thin, I.M., or thick PCM has the genetic capability to metastasize and facilitate the development of an appropriate treatment strategy.

Example 7

Materials and Methods

Tumor specimens. Tumor samples were surgically procured from patients with primary cutaneous melanoma (PCM), squamous cell carcinoma (SCC), basal cell carcinoma (BCC) and metastatic melanoma (MM) over a 3 year period. All samples were obtained under an Investigational Review Board (IRB) approved tissue procurement protocol (MCC#13448, IRB#101751; PSM#990914-JM, 020318-JM). Upon surgical removal of the primary melanoma, a single surgical oncologist (A.I.R.) utilized a scalpel to macrodissect and procure a portion of the remaining primary tumor, with a similar technique utilized for grossly involved lymph nodes where the melanoma had completely replaced the lymph node. Samples were taken from non-necrotic areas of the tumor. The same process was performed for all distant metastases, with care taken to avoid surrounding tissues and stroma.

All samples were cryopreserved in liquid nitrogen and stored within the Tissue Procurement Laboratory of the Moffitt Cancer Center, securely de-identified through a centralized database. Forty MM samples were analyzed, composed of 22 bulky, macroscopic (replaced) lymph node metastases, 16 subcutaneous and 2 solid organ metastases (adrenal and brain). These MM samples were compared with 42 primary cutaneous cancers (16 PCM, 11 SCC, 15 BCC). PCM consisted of 2 melanoma in situ (MIS), 2 thin melanomas (<1 mm), 3 intermediate-thickness melanomas (1-4 mm), and 9 thick melanomas (>4 mm). Additionally, 4 samples of normal human skin and 1 sample of cultured NHEM were included. All MM samples were procured from patients that had failed multiple previous therapies, ranging from single agent Interferon, single or multi-agent chemotherapy, immunotherapy or other experimental treatment options. All primary cutaneous cancers were procured from previously untreated patients.

RNA isolation, purification and hybridization. A portion of each cryopreserved tissue sample was dissolved in TRIzol® (Invitrogen, Carlsbad, Calif.), purified according to manufacturer's recommendations, and further purified on RNeasy columns (Qiagen Inc., Valencia, Calif.). RNA integrity was verified by both gel electrophoresis and the Agilent 2100 Bioanalyzer (Agilent Technologies, Palo Alto, Calif.). A total of 5 μg of RNA was processed using established Affymetrix protocols for the generation of biotin-labeled cRNA and the hybridization, staining, and scanning of arrays as outlined in the Affymetrix technical manuals (Van Gelder et al., Proc. Natl. Acad. Sci. U.S.A. 87:1663-1667, 1990; Warrington et al., Physiol. Genomics. 2:143-147, 2000). The processed RNA was hybridized to Human Genome U133 Plus 2.0 arrays from Affymetrix, Inc. (Santa Clara, Calif.), and scanned on an Affymetrix GeneChip® scanner 3000 at 2.5 μm resolution. A more complete description of this process is available in Dobbin et al., Clin. Can. Res. 11:565-572, 2005. The tissue samples were processed in three independent groups.

Cell lines and tissue culture. Freshly excised melanoma samples were placed into culture media (RPMI 1640+5% FCS) and tissue procurement and expansion of daughter cell lines was established utilizing previously published techniques (Riker et al., Can Detect and Prev, 23(5):387-96, 1999; Riker A I. The isolation and culture of melanoma cell lines. In: Langdon S, editor. *Cancer cell culture: Methods and protocols*. Totowa: Humana Press; pp. 93-100, 2004). All cell lines were split and passaged<10 times and, characterized by flow cytometry and/or cytospin preparation for cellular confirmation of melanoma cell purity (data not shown). The cell lines, TC077 and TC80a were derived from primary melanoma samples with TC80b derived from a metastatic lymph node (from the same patient). The cell lines, TC12A and TC12F, were derived from 2 different subcutaneous melanoma nodules from: the same patient. There were 3 cell lines examined from metastatic samples, TC66C, TC72 and TC89. The NHEM were cultured according to the manufacturer directions. (Cambrex BioScience, Walkersville, Md.).

Semi and real-time quantitative RT-PCR. First-strand cDNA synthesis was performed using Superscript III RT (Invitrogen). Subsequently, the cDNA was used in semi-quantitative PCR. Each sample was normalized with β-Actin as an internal control, comparing each sample with AlphaEase®FC image analysis software (Alpha Innotech, San Leandro, Calif.), followed by densitometric analysis of the integrated values for each sample. The expression levels of putative oncogenes and tumor suppressor genes were analyzed by real-time quantitative RT-PCR (qPCR) using Assays-on-Demand. Gene Expression Assays (Applied Biosystems, Foster City, Calif.): SPP1 (osteoponin, assay ID Hs00167093_m1), GDF15 (growth differentiation factor 15, assay ID Hs00171132_ml), PITX1 paired-like homeodomain transcription factor1, assay ID Hs00267528 ml), DSC3 (desmocollin 3, assay ID Hs00170032_m1), CST6 (cystatin E/M, assay ID Hs00154599), POU2F3 (POU domain, class 2, transcription factor 3, assay ID Hs00205009) and GAPDH (assay IDHs99999905_m1) as the internal standard. Utilizing normal skin as the calibrator, the relative quantitation values of a target template for each sample were expressed as $2^{-\Delta\Delta Ct}$. Briefly, qPCR analysis was performed utilizing 40 ng of total cDNA in a 25 µl reaction volume (Applied Biosystems). QPCR was performed utilizing established techniques, with all samples performed in triplicate and run on an ABI/PRISM 7500 Sequence Detector System (Applied Biosystems).

Gene microarray analysis and bioinformatics. Affymetrix MAS 5.0 analysis software was used to generate signal values for all probe sets based upon a mean intensity of 500, subsequently exported and iteratively normalized as a whole group to create the final normalization based upon the most stable gene expression measurements across all samples (Li et al., Proc. Natl. Acad. Sci. U.S.A. 98:31-36, 2001). This process was performed for the initial group of tumor samples to generate the list of normalization probesets that were subsequently used to scale all samples processed for this study to an average intensity of 4000 for the normalization probesets. Following scaling, the calculated signal values were then used to calculate the average expression level for each gene in each tissue type using an initial group of 23 tumor samples. The average expression values derived from this initial set were directly compared to identify genes expressed at high levels in one tumor type but not in the other samples using a t-test and visual inspection to find highly differential expression patterns. Genes highly expressed in metastatic melanomas but not primary melanomas, basal cell carcinomas, or squamous cell carcinomas, were sought. Several genes were initially selected that exhibited the idealized gene expression profiles. Additional candidate genes were then identified by using Pearson's correlation between the idealized gene expression patterns and all other probe sets on the arrays. Positively correlated (r>0.7) and negatively correlated (r<0.7) genes were identified and trimmed to include only those with a 2-fold or greater difference in the average gene expression level between metastatic samples and non-metastatic tumors. This initial gene expression survey identified 2014 Affymetrix probe sets from the U133 Plus 2.0 arrays that showed differential expression between metastatic tumor samples and non-metastatic tumor samples.

The 2014 probe sets identified as correlating with the metastatic phenotype were used to cluster the samples. Following normalization, as described above, the signal values were log 2 transformed. Each probe set was then mean centered across all samples and the resulting values were input into Eisen's cluster. Hierarchical clustering was performed using absolute correlation and a complete linkage. Clustering was performed with various subgroups of the data or with all samples together and resulted in similar sample groupings. Individual samples were classified based on the class of the other samples in the closest cluster. The complete microarray data is available from the Gene Expression Omnibus (world wide web address: ncbi.nlm.nih.gov/geo/) under Accession number GSE7553.

Serial Analysis of Microarrays (SAM) was performed in order to identify a more extensive list of differentially expressed genes expressed between PCM and MM. Two comparisons were made to generate a comprehensive and yet confident list of genes that are differentially expressed between metastatic melanoma and non-metastatic melanomas. In the first comparison, the metastatic melanoma samples were opposed by all the non-metastatic samples including basal and squamous cell carcinoma and normal skin. The false discovery rate threshold used to limit the gene list was 0% for this comparison. Because of the number of samples, this provides good statistical confidence but does not focus on the differences between primary melanoma and metastatic melanoma. A second comparison was performed utilizing 6 thin primary melanoma samples in opposition to 6 randomly selected metastatic melanomas. The only non-random aspects of this sample selection were to avoid selecting samples in which the classifier disagreed with the pathologist's diagnosis and to avoid utilizing more than one sample from the same individual. For this comparison the median false discovery rate threshold was set at 5%. This latter analysis is the preferred grouping of samples, but because of the small sample size it is also more likely to generate false discoveries due to noise and outlier samples. Therefore the more confident gene list generated by combining the two analyses. The intersection of the two approaches yielded 1,352 probe sets with higher expression in the metastatic samples and 2,991 probe sets with higher expression in non-metastatic samples. This list was further reduced by removing probe sets that did not appear to have a difference greater than 2-fold on average between the two groups.

Following all microarray analyses, the identified probe sets were annotated based on the sequence of the probes used on the arrays (Harbig et al., Nucleic Acids Res. 33:e31, 2005).

Western blot analysis. Whole cell extracts from PCM and MM cell lines were prepared by directly lysing cells in SDS sample buffer. Expression of SPP-1 protein was assessed in cell lysate and serum-free conditioned medium. Briefly, $4\times10^6$ cells were plated in 5% FBS containing medium; 24 hours later, the growth medium was replaced with serum-free medium. The conditioned media and cell lysates were harvested 24 hours later and resolved using a 12.5% SDS-PAGE. Proteins were transferred to a PVDF membrane and probed with the anti-human SPP-1 mouse monoclonal antibody (Sigma, St. Louis, Mo.) (1:1000) followed by a secondary antibody conjugated to horseradish peroxidase (Amersham Biosciences, Piscataway, N.J.) and detected using chemiluminescence (Santacruz Biotechnology, Santa Cruz, Calif.). The osteopontin band (SPP-1) was visualized at ~55-65 kDa. Daughter melanoma cell lines derived from the freshly procured melanoma samples (with the exception of A375) were lysed by M-PER™ Mammalian Protein Extraction Reagent (Pierce, Rockford, Ill.) and processed according to manufacturer instructions. A total of 15 µg of protein from each experimental condition were electrophoresed on 10% SDS-PAGE and transferred to nitrocellulose membranes (Bio-Rad, Hercules, Calif.). Immunostaining was performed with the following primary antibodies: DSC3 (Santa Cruz) 1:200; CLCA2 (Novus Biologicals, Littleton, Colo.) 1:500; PDGFRL (Novus Biologicals) 1:500; α-tubulin (Cell signaling, Danvers, Mass.), 1:1000. Immunocomplexes were visualized using an enhanced chemiluminescence (ECL) Western Blotting Substrate (Pierce). The intensity of the bands were scanned with a Fujifilm intelligent dark box II and analyzed with Fujifilm Las-1000 Lite V1.3 software.

A number of embodiments of the technology have been described. Nevertheless, it will be understood that various modifications may be made without departing from the spirit and scope of the technology. Accordingly, other embodiments are within the scope of the following claims.

What is claimed is:

1. A method of evaluating a melanoma from a patient, the method comprising:

determining mRNA levels of five or more genes selected from the group consisting of: tripartite motif-containing 51 (TRIM51) (SEQ ID NO:1); Glycophorin C (Gerbich blood group) (GYPC) (SEQ ID NO:2); SRY (sex determining region Y)-box 5 (SOX5) (SEQ ID NO:3); kinesin family member C1 (KIFC1) (SEQ ID NO:4); SEC22 vesicle trafficking protein-like 3 (*S. cerevisiae*) (SEC22L3) (SEQ ID NO:5); and secreted phosphoprotein 1 (osteopontin, bone sialoprotein I, early T-lymphocyte activation 1) (SPP1) (SEQ ID NO:6) in a test sample comprising melanoma cells from the patient, and comparing said mRNA levels to a set of reference levels that represent levels of the mRNAs in a sample comprising cells from a non-metastatic melanoma, wherein an increase in expression of said five or more genes indicates an increased likelihood that the melanoma is a metastatic melanoma.

2. The method of claim 1, wherein miRNA levels of all six genes are determined.

3. The method of claim 1, wherein mRNA levels of the five or more genes is determined relative to mRNA levels of the five or more genes in a reference set of non-metastatic cutaneous tissue samples, and wherein an increase in expression of said five or more genes, relative to expression of the five or more genes in the reference set, indicates an increased likelihood that the melanoma is a metastatic melanoma.

4. The method of claim 1, wherein mRNA levels of the five or more genes is compared to: (a) mRNA levels in a first reference set of non-metastatic cutaneous tissue samples, and (b) mRNA levels in a second reference set of metastatic melanoma tissue samples; wherein a greater similarity in mRNA levels of the five or more genes in the test sample to the second reference set than to the first reference set indicates an increased likelihood that the melanoma is a metastatic melanoma.

5. The method of claim 1, wherein determining mRNA levels of five or more genes in the test sample comprises isolating RNA from the test sample, and detecting expression of the RNA.

6. The method of claim 5, wherein determining mRNA levels of five or more genes in the test sample comprises performing reverse transcriptase polymerase chain reaction.

7. The method of claim 5, wherein determining mRNA levels of five or more genes in the test sample comprises performing microarray analysis.

8. The method of claim 1, wherein the test sample is a test sample from a primary melanoma.

* * * * *

UNITED STATES PATENT AND TRADEMARK OFFICE
Certificate

Patent No. 7,615,349 B2

Patented: November 10, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Adam I. Riker, Mobile, AL (US); Steven Alan Enkemann, Lutz, FL (US); and Jaime Matta, Ponce (PR).

Signed and Sealed this Fourth Day of January 2011.

MISOOK YU
*Supervisory Patent Examiner*
Art Unit 1642
Technology Center 1600

SEQUENCE LISTING

<160> NUMBER OF SEQ ID NOS: 6

<210> SEQ ID NO 1
<211> LENGTH: 1288
<212> TYPE: DNA
<213> ORGANISM: Homo sapiens

<400> SEQUENCE: 1

| | | | | | |
|---|---|---|---|---|---:|
| agatttgaca | aacatgagga | gaaacaaagc | aaactctctt | ttctgtgggt | taatttgtct | 60 |
| ctcattttgg | gtccttcgta | tatcagagtg | tgaatgatac | tttattgtcc | tcacttgtgc | 120 |
| ttcaattcgt | ggctgttttg | caggaggagc | tcctaaaaaa | aatgcagtct | ttatgggaaa | 180 |
| aagcttgtga | aaatctcaga | aatctgaaca | tggaaccac | aagaaccaga | tgctggaagg | 240 |
| attatgtgag | tttaaggata | gaagcaatca | gagctgaata | tcagaagatg | cctgcatttc | 300 |
| tccatgaaga | gagcaacat | cacttggaaa | ggctgcgaaa | ggagggcgag | acatttttc | 360 |
| agcaactcaa | tgaaagcaaa | gccagaatgg | aacattccag | ggagctttta | agaggaatgt | 420 |
| atgaggatct | gaagcaaatg | tgccataaag | cagatgtgga | gctactccag | gcttttggag | 480 |
| acatattaca | caggtatgag | tctctgctgc | tgcaagtgtc | tgagcctgtg | aatccagagc | 540 |
| tcagtgcagg | gcccatcact | ggactgctgg | acagcctcag | tggattcaga | gttgatttta | 600 |
| ctctgcagcc | tgaaagagcc | aatagtcata | tcttcctgtg | tggagatttg | agaagcatga | 660 |
| atgttggatg | tgaccctcaa | gatgatcccg | atatcactgg | aaaatctgaa | tgttttcttg | 720 |
| tatgggggc | tcaggctttc | acatctggca | aatattattg | ggaggttcat | atgggggact | 780 |
| cttggaattg | ggcttttggt | gtctgtaaca | attattggaa | agagaagaga | cagaatgaca | 840 |
| agatagatgg | agaggaggga | ctctttcttc | ttggatgtgt | taaggaggac | actcactgca | 900 |
| gtctctttac | cacctcccca | cttgtggtgc | aatatgttcc | aagacctacc | agcacagtag | 960 |
| gattattcct | ggattgtgaa | ggtagaaccg | tgagctttgt | tgatgttgat | caaagttccc | 1020 |
| tgatatacac | catccccaat | tgctccttct | cacctcctct | caggcctatc | tttttgctgta | 1080 |
| gtcacttctg | accagagaaa | agtcagaaat | gtgcctgtat | gctctgggaa | cctgtttatc | 1140 |
| ccagaaagcc | ctctttttcg | cacctcatca | aacagaacaa | ataagttata | tttaatgtct | 1200 |
| ttagttgcat | tctaatgtca | tcaaaactca | tttatagtgt | ttctattaaa | tatggtgaaa | 1260 |
| acattaaaaa | aaaaaaaaaa | aaaaaaaa | | | | 1288 |

<210> SEQ ID NO 2
<211> LENGTH: 1075
<212> TYPE: DNA
<213> ORGANISM: Homo sapiens

<400> SEQUENCE: 2

| | | | | | |
|---|---|---|---|---|---:|
| gagcccctcc | cctcggcccg | cgcgggagga | gtgtgaccca | ggtgccgctt | cctctcgccg | 60 |
| ccgagggtca | ggagcccggg | agcgcgaccc | tccccggcc | cggcctggcc | cggcctggcc | 120 |
| agtcccgcg | gtctctgccc | gggctgacgc | ccaggaatgt | ggtcgacgag | aagcccaac | 180 |
| agcacggcgt | ggcctctcag | cctcgagcct | gatccgggga | tggcctctgc | ctccaccaca | 240 |
| atgcatacta | ccaccattgc | agagcctgat | ccagggatg | ctggatggcc | ggatggcaga | 300 |
| atggagacct | ccaccccac | cataatggac | attgtcgtca | ttgcaggtgt | gattgctgct | 360 |
| gtggccatcg | tcctagtctc | cctcctcttc | gtcatgctgc | gctacatgta | ccggcacaag | 420 |
| ggcacgtacc | acaccaatga | ggccaagggc | acggagtttg | ctgagagtgc | agatgcagcc | 480 |

| | |
|---|---|
| ctgcagggag accctgccct ccaagatgct ggtgatagca gcagaaagga gtactttatt | 540 |
| tgagggacaa cagacttcac ttccctgaat gcctccccca tctccatcag gaaaaataca | 600 |
| ccccatcgcc cagcacccct gctgatacca ccagacagag agagagagca cttgattctt | 660 |
| cccgagatag ccacctggaa cactaggtg cctgcccagg gaggaacgga ggaggactcg | 720 |
| cgctacaaga ggccactccc agggaccag ggaggcgatg ccacccccag aggccacctt | 780 |
| ttgctccacg gaggtgggag aaaatctggg cacatgggc cccctgggca gtgcaggaca | 840 |
| acatcagctc actggcagga aagtccttgt tgagggtgag ggggtgctgg ggtacccggg | 900 |
| ggctggggaa gcaaggaaat aagtcatctg tatgctgact ggggataatg gcatcaaatg | 960 |
| tcagtccttg acatttgggg ggaacagcag gtgccagagc taaaaggtac ctttgtctgc | 1020 |
| cattgatcca gctcagaacg attggaaata aatttgaaat gtaaccgagc aaaaa | 1075 |

<210> SEQ ID NO 3
<211> LENGTH: 4333
<212> TYPE: DNA
<213> ORGANISM: Homo sapiens

<400> SEQUENCE: 3

| | |
|---|---|
| gagaaaatca attggtttag aaggtttgga ctcacttgac aggttcagtt ggagacgatc | 60 |
| ataggtggct gctgtgacaa agggaaattg tgcttttcca gcatgcttac tgaccctgat | 120 |
| ttacctcagg agtttgaaag gatgtcttcc aagcgaccag cctctccgta tggggaagca | 180 |
| gatggagagg tagccatggt gacaagcaga cagaaagtgg aagaagagga gagtgacggg | 240 |
| ctcccagcct ttcaccttcc cttgcatgtg agttttccca acaagcctca ctctgaggaa | 300 |
| tttcagccag tttctctgct gacgcaagag acttgtggcc ataggactcc cacttctcag | 360 |
| cacaatacaa tggaagttga tggcaataaa gttatgtctt catttgcccc acacaactca | 420 |
| tctacctcac ctcagaaggc agaagaaggt gggcgacaga gtggcgagtc cttgtctagt | 480 |
| acagccctgg gaactcctga cggcgcaag gcagtttag ctgatgttgt tgacaccttg | 540 |
| aagcagagga aaatggaaga gctcatcaaa acgagccgg aagaaccccc cagtattgaa | 600 |
| aaactactct caaaggactg gaaagacaag cttcttgcaa tgggatcggg aactttggc | 660 |
| gaaataaaag ggactcccga gagcttagct gagaaagaaa ggcaactcat gggtatgatc | 720 |
| aaccagctga ccagcctccg agagcagctg ttggctgccc acgatgagca gagaaacta | 780 |
| gctgcctctc agattgagaa acagcgtcag caaatggagc tggccaagca gcaacaagaa | 840 |
| caaattgcaa gacagcagca gcagcttcta cagcaacaac acaaaatcaa tttgctccag | 900 |
| caacagatcc aggttcaagg tcagctgccg ccattaatga ttcccgtatt ccctcctgat | 960 |
| caacggacac tggctgcagc tgcccagcaa ggattcctcc tccctccagg cttcagctat | 1020 |
| aaggctggat gtagtgaccc ttaccctgtt cagctgatcc aactaccat ggcagctgct | 1080 |
| gccgcagcaa caccaggctt aggcccactc caactgcagc agttatatgc tgcccagcta | 1140 |
| gctgcaatgc aggtatctcc aggagggaag ctgccaggca tacccaagg caaccttggt | 1200 |
| gctgctgtat ctcctaccag cattcacaca gacaagagca caaacagccc accacccaaa | 1260 |
| agcaaggatg aagtggcaca gccactgaac ctatcagcta aacccaagac ctctgatggc | 1320 |
| aaatcaccca catcacccac ctctccccat atgccagctc tgagaataaa cagtggggca | 1380 |
| ggcccctca agcctctgt cccagcagcg ttagctagtc cttcagccag agttagcaca | 1440 |
| ataggttact taaatgacca tgatgctgtc accaaggcaa tccaagaagc tcggcaaatg | 1500 |

```
aaggagcaac tccgacggga acaacaggtg cttgatggga aggtggctgt tgtgaatagt   1560
ctgggtctca ataactgccg aacagaaaag gaaaaaacaa cactggagag tctgactcag   1620
caactggcag ttaaacagaa tgaagaagga aaatttagcc atgcaatgat ggatttcaat   1680
ctgagtggag attctgatgg aagtgctgga gtctcagagt caagaattta tagggaatcc   1740
cgagggcgtg gtagcaatga accccacata aagcgtccaa tgaatgcctt catggtgtgg   1800
gctaaagatg aacggagaaa gatccttcaa gcctttcctg acatgcacaa ctccaacatc   1860
agcaagatat tgggatctcg ctggaaagct atgacaaacc tagagaaaca gccatattat   1920
gaggagcaag cccgtctcag caagcagcac ctggagaagt accctgacta taagtacaag   1980
cccaggccaa agcgcacctg cctggtggat ggcaaaaagc tgcgcattgg tgaatacaag   2040
gcaatcatgc gcaacaggcg gcaggaaatg cggcagtact tcaatgttgg gcaacaagca   2100
cagatcccca ttgccactgc tggtgttgtg taccctggag ccatcgccat ggctgggatg   2160
ccctcccctc acctgccctc ggagcactca agcgtgtcta gcagcccaga gcctgggatg   2220
cctgttatcc agagcactta cggtgtgaaa ggagaggagc acatatcaa agaagagata    2280 caggccgagg acatcaatgg agaaatttat gatgagtacg acgaggaaga ggatgatcca   2340
gatgtagatt atgggagtga cagtgaaaac catattgcag acaagccaa ctgataaggg    2400 tcaaaagatt gttgtgacct taggacttaa agaagcccta actggttcat ccttaccagt   2460
ggccaagcac attaactttc tcatacactg actgttactt taactgttag tcttaaatag   2520
ttgggacatc agctgactaa tagacctcag cctcaaaagg cttggaaaga aaaacaaat    2580 acaacaagca aacaacaata tcaacaacaa gagattgaaa taagctatgg gtaaaataat   2640
gccagtaatt cagctgctac atccaagcac tgaagtctta cccgtcaact ttttttttt    2700 tttaaataaa ctttatggct gtttgttcta caatgttcta gaaattctca ctcaggtaca   2760
cagtgccaac aagtggcttg tgaatgtgtt ttgttgtttt gtgctacaat ttttaaaaag   2820
aaaaaagttt tgttttgttt tttggggttt ctgggttttt tccttttctt tttctttcct   2880
ttcatttttt ttctttgtaa tgcacctgac agaaaaaaaa gaaaaatgaa tttctcttta   2940
cttctctcca ccttctccat ctctctactt taaagatgga agtctgtgca tgaggggaaa   3000
gagggaaaaa gagcctgttt ttaacttcct tgctatccac cacaaaataa gcaattattt   3060
tctttagagg actttatcta ttgcacacca cactacatct ttgagcaagt gccaaatttg   3120
tactgaagtg ttgaccaagt tcattttttc tctttacttt ttcctttttcc ttcttaagtt   3180 aggacagtgt taaatcttag acaatccctt gaaaaacctg aaataccagc agctggtgag   3240
atttgacttt tttttttaat ggaaactgta ggtgctgttc tcaggtgaaa agagagagag   3300
agagagagac ataagaaatt tagagaaaaa tattttctga tcttggattt ttgtgtgtat   3360
gtatgtatgt gattatggta ctaataatag gaataacgtt ggaccattgt gagttaaacc   3420
cacatctggg gatgaaatcc cacatcctcc caagtgactg gtctagaaat aatcttgacc   3480
ttgactttgc acttcaaatg acaacttaac caagtatagg gctcagaaat tatattttta   3540
aatgtctgat tattattgga tggatcaggt ggccctgtgt aatagaggtg tgcatgtata   3600
acatggaagc tactagcaaa ctgctcccag atgtcctttc tccctggtca gttggttcca   3660
ttaacgtttg ctactagtg attttgtttt ttcctgttga tattttgagc aaaacaatca    3720
ttgttttcat tgaatatatt tggccatttt ttcagacaaa tagaattagc ttatttcttc   3780
aacattccat cctttcccga tcaggaaatg aaactgatga ttttataagg tatttttcac   3840
ccctccatga agtgaggtgg aggcctttag catttcagaa gtgtgggcca tatgtagttc   3900
```

```
atgccataaa aagtaggatt taattaaaag tcattgcagc ccaataaaat ggagcctggc    3960
tgcacccagg gatccttgcc actgctcttc ccttgctgtc agattaatcc actgaagtcc    4020
aactttggtt caagcagagt atttgcaaag agcaacaact gaatgtgatg ggactgctta    4080
tgtagatttt gccagccaaa tgccaaggca gttgtagggc ctgtacaaat aaatgcaaaa    4140
tcatttcaag tcaattgcca ttatttgtat tgaagtatca gatagatagt aaatactgca    4200
actagtagct tgatgtgcta tagttttcac tccagtcatc attttcctat ctcaccccc     4260 gaaacaccac cctaaagttg gattttttaca tataaataaa aaagaatcc cttttaaaaa    4320 aaaaaaaaaa aaa                                                       4333

<210> SEQ ID NO 4
<211> LENGTH: 2391
<212> TYPE: DNA
<213> ORGANISM: Homo sapiens

<400> SEQUENCE: 4
tcaaaagtgg cgggtgtggc gcggggctgg tagcggccgg agccgtgcga gttctctacc      60
ctgcttcgcg agcgggcgag agaacgcgag tcccaggatc cccggcaccc agttctcttc     120
cactgcattc ccccggcgcg tgtgggaccg aggtggacat ggatccgcag aggtcccccc     180
tattggaagt aaagggggaac atagaactga agagacctct gattaaggcc ccttcccagc    240
tgcctctctc aggaagcaga ctcaagagga ggcctgacca gatggaagat ggcctggagc     300
ctgagaagaa acgacaagaa ggcctgggtg caacgaccaa aattaccaca tcccacccaa     360
gagttccatc cctcactaca gtgccacaga cacaaggcca gaccacagct caaaaagttt     420
ccaagaagac aggaccccgg tgttccacag ctattgccac agggttgaag aaccagaagc     480
cagttcctgc tgttcctgtc cagaagtctg gcacatcagg tgttcctccc atggcaggag     540
ggaagaaacc cagcaaacgt ccagcctggg acttaaaggg tcagttatgt gacctaaatg     600
cagaactaaa acggtgccgt gagaggactc aaacgttgga ccaagagaac cagcagcttc     660
aggaccagct cagagatgcc cagcagcagg tcaaggccct ggggacagag cgcacaacac     720 tggagggca tttagccaag gtacaggccc aggctgagca gggccaacag gagctgaaga     780
acttgcgtgc ttgtgtcctg gagctggaag agcggctgag cacgcaggag ggcttggtgc     840
aagagcttca gaaaaaacag gtggaattgc aggaagaacg gaggggactg atgtcccaac     900
tagaggagaa ggagaggagg ctgcagacat cagaagcagc cctgtcaagc agccaagcag     960
aggtggcatc tctgcggcag gagactgtgg cccaggcagc cttactgact gagcgggaag    1020
aacgtcttca tgggctagaa atggagcgcc ggcgactgca caaccagctg caggaactca    1080
agggcaacat ccgtgtattc tgccgggtcc gccctgtcct gccgggggag cccactccac    1140
cccctggcct cctcctgttt ccctctggcc ctggtgggcc ctctgatcct caacccgcc     1200 ttagcctctc ccggtctgac gagcggcgtg ggaccctgag tggggcacca gctcccccac    1260
ctcgccatga ttttttcctttt gacccggtat tccaccagg aagtggacag gatgaagtgt    1320
ttgaagagat tgccatgctt gtccagtcag ccctggatgg ctatccagta tgcatctttg    1380
cctatggcca gacaggcagt ggcaagacct tcacaatgga gggtgggcct ggggagacc     1440 cccagttgga ggggctgatc cctcgggccc tgcggcacct cttctctgtg gctcaggagc    1500
tgagtggtca gggctggacc tacagctttg tagcaagcta cgtagagatc tacaatgaga    1560
ctgtccggga cctgctggcc actggaaccc ggaagggtca agggggcgag tgtgagattc    1620
```

```
gccgtgcagg gccagggagt gaggagctca ctgtcaccaa tgctcgatat gtccctgtct   1680
cctgtgagaa agaagtggac gccctgcttc atctggcccg ccagaatcgg gctgtggccc   1740
gcacagccca gaatgaacgg tcatcacgca gccacagtgt attccagcta cagatttctg   1800
gggagcactc cagccgaggc ctgcagtgtg gggcccccct cagtcttgtg gacctggccg   1860
ggagtgagcg acttgacccc ggcttagccc tcggccccgg ggagcgggaa cgccttcggg   1920
aaacacaggc cattaacagc agcctgtcca cgctggggct ggttatcatg ccctgagca   1980 acaaggagtc ccacgtgcct taccggaaca gcaaactgac ctacctgctg cagaactctc   2040
tgggtggtag tgctaagatg ctcatgtttg tgaacatttc tccactggaa gagaacgtct   2100
ccgagtccct caactctcta cgctttgcct ccaaggtgaa ccagtgtgtt attggtactg   2160
ctcaggccaa caggaagtga agacggatcc agatctgtgt gtgtgtgtgt gtgtgtgtgt   2220
gtgtgtgtgt gtgtgtgtgt gtgtgtgtcc ctatgtctat gtatcgggtg aggggtggga   2280
gggttgctgg agggtgcttt attgggtgga gggcaccatg tcccagggct atcaaataaa   2340
gaatagtttg gtttttttttt taaaaaaaaa aaaaaaaaa aaaaaaaaa a             2391

<210> SEQ ID NO 5
<211> LENGTH: 1396
<212> TYPE: DNA
<213> ORGANISM: Homo sapiens

<400> SEQUENCE: 5
ctgggccgag ccctcccggt cggctaagat tgctgaggag gcggcgggta gctggcaggc     60
gccgacttcc gaaggccgcc gtccgggcga ggtgtcctca tgacttctct tgtggaccat    120
gtccgtgatc ttttttgcct gcgtggtacg ggtaagggat ggactgcccc tctcagcctc    180
tactgatttt taccacaccc aagatttttt ggaatggagg agacggctca agagtttagc    240
cttgcgactg gcccagtatc caggtcgagg ttctgcagaa ggttgtgact ttagtataca    300
tttttcttct ttcggggacg tggcctgcat ggctatctgc tcctgccagt gtccagcagc    360
catggccttc tgcttcctgg agaccctgtg gtgggaattc acagcttcct atgacactac    420
ctgcattggc ctagcctcca ggccatacgc tttttcttgag tttgacagca tcattcagaa    480
agtgaagtgg cattttaact atgtaagttc ctctcagatg gagtgcagct tggaaaaaat    540
tcaggaggag ctcaagttgc agcctccagc ggttctcact ctggaggaca cagatgtggc    600
aaatggggtg atgaatggtc acacaccgat gcacttggag cctgctccta atttccgaat    660
ggaaccagtg acagccctgg gtatcctctc cctcattctc aacatcatgt gtgctgccct    720
gaatctcatt cgaggagttc accttgcaga acattcttta caggttgccc atgaggaaat    780
tggaaacatt ctggcttttc ttgttccttt cgtagcctgc attttccagt gttatttgta    840
cctgttctac agtccagcca ggactatgaa ggtggtgctt atgctgctct ttatttgcct    900
gggcaacatg tacctgcacg ggctgaggaa cctctggcaa atccttttcc acataggagt    960
ggcttttctg tcttcatatc agatactaac aaggcagctt caggagaagc agtctgactg   1020
tggagtatga ggatgacact gtgatgaatg gattctttga tttcttttg aggatcaatc   1080 tatgtttctc tttctgcttc tctactttac actccagttt ccatccttt cagccaactg   1140 gactgaaaaa ccaggaattg gggatgttaa acagttgcag tggaagtcat gaggttgctt   1200
gatacccagc cttggttctg tgccaagcat tactgcagga tctccagcca gttcagcacg   1260
tttacctagg acagctggat ctgggggctc atccagaaag agctttattg gaagagagaa   1320
aggaaatatt ttggtctttt aagttgaatg atacagtaaa ccacttgatt caataacaaa   1380
```

```
aaaaaaaaaa aaaaaa                                                  1396

<210> SEQ ID NO 6
<211> LENGTH: 1560
<212> TYPE: DNA
<213> ORGANISM: Homo sapiens

<400> SEQUENCE: 6
ctccctgtgt tggtggagga tgtctgcagc agcatttaaa ttctgggagg gcttggttgt    60
cagcagcagc aggaggaggc agagcacagc atcgtcggga ccagactcgt ctcaggccag   120
ttgcagcctt ctcagccaaa cgccgaccaa ggaaaactca ctaccatgag aattgcagtg   180
atttgctttt gcctcctagg catcacctgt gccataccag ttaaacaggc tgattctgga   240
agttctgagg aaaagcagaa tgctgtgtcc tctgaagaaa ccaatgactt taaacaagag   300
acccttccaa gtaagtccaa cgaaagccat gaccacatgg atgatatgga tgatgaagat   360
gatgatgacc atgtggacag ccaggactcc attgactcga acgactctga tgatgtagat   420
gacactgatg attctcacca gtctgatgag tctcaccatt ctgatgaatc tgatgaactg   480
gtcactgatt ttcccacgga cctgccagca accgaagttt tcactccagt tgtccccaca   540
gtagacacat atgatggccg aggtgatagt gtggtttatg gactgaggtc aaaatctaag   600
aagtttcgca gacctgacat ccagtaccct gatgctacag acgaggacat cacctcacac   660
atggaaagcg aggagttgaa tggtgcatac aaggccatcc ccgttgccca ggacctgaac   720
gcgccttctg attgggacag ccgtgggaag gacagttatg aaacgagtca gctggatgac   780
cagagtgctg aaacccacag ccacaagcag tccagattat ataagcggaa agccaatgat   840
gagagcaatg agcattccga tgtgattgat agtcaggaac tttccaaagt cagccgtgaa   900
ttccacagcc atgaatttca cagccatgaa gatatgctgg ttgtagaccc caaaagtaag   960
gaagaagata acacctgaa atttcgtatt tctcatgaat tagatagtgc atcttctgag    1020
gtcaattaaa aggagaaaaa atacaatttc tcactttgca tttagtcaaa agaaaaaatg   1080
ctttatagca aaatgaaaga gaacatgaaa tgcttctttc tcagtttatt ggttgaatgt   1140
gtatctattt gagtctggaa ataactaatg tgtttgataa ttagtttagt ttgtggcttc   1200
atggaaactc cctgtaaact aaaagcttca gggttatgtc tatgttcatt ctatagaaga   1260
aatgcaaact atcactgtat tttaatattt gttattctct catgaataga aatttatgta   1320
gaagcaaaca aaatactttt acccacttaa aaagagaata taacatttta tgtcactata   1380
atcttttgtt ttttaagtta gtgtatattt tgttgtgatt atcttttttgt ggtgtgaata   1440
aatcttttat cttgaatgta ataagaattt ggtggtgtca attgcttatt tgttttccca   1500
cggttgtcca gcaattaata aaacataacc tttttactg cctaaaaaaa aaaaaaaaa    1560
```